(12) United States Patent
Holenz et al.

(10) Patent No.: US 8,030,500 B2
(45) Date of Patent: Oct. 4, 2011

(54) SUBSTITUTED ISOINDOLES FOR THE TREATMENT AND/OR PREVENTION OF Aβ-RELATED PATHOLOGIES

(75) Inventors: Jörg Holenz, Södertälje (SE); Sofia Karlström, Södertälje (SE); Karin Kolmodin, Södertälje (SE); Johan Lindström, Södertälje (SE); Laszlo Rakos, Södertälje (SE); Didier Rotticci, Södertälje (SE); Peter Söderman, Södertälje (SE); Britt-Marie Swahn, Södertälje (SE); Stefan Von Berg, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/618,212

(22) Filed: Nov. 13, 2009

(65) Prior Publication Data
US 2010/0125082 A1    May 20, 2010

Related U.S. Application Data

(60) Provisional application No. 61/114,634, filed on Nov. 14, 2008, provisional application No. 61/139,767, filed on Dec. 22, 2008, provisional application No. 61/221,653, filed on Jun. 30, 2009.

(51) Int. Cl.
C07D 209/44     (2006.01)
(52) U.S. Cl. .................. 548/471; 544/333; 546/268.1
(58) Field of Classification Search .................. 544/333; 546/268.1; 548/471
See application file for complete search history.

(56) References Cited

U.S. PATENT DOCUMENTS

| | | | |
|---|---|---|---|
| 4,605,642 | A | 8/1986 | Rivier et al. |
| 5,063,245 | A | 11/1991 | Abreu et al. |
| 5,698,705 | A | 12/1997 | Alfter et al. |
| 5,716,446 | A | 2/1998 | Alfter et al. |
| 5,877,399 | A | 3/1999 | Hsiao et al. |
| 5,942,400 | A | 8/1999 | Anderson et al. |
| 6,211,235 | B1 | 4/2001 | Wu et al. |
| 6,221,667 | B1 | 4/2001 | Reiner et al. |
| 6,245,884 | B1 | 6/2001 | Hook |
| 6,245,964 | B1 | 6/2001 | McLonlogue et al. |
| 7,629,356 | B2 | 12/2009 | Chessari et al. |
| 7,855,213 | B2 | 12/2010 | Arnold et al. |
| 2005/0282825 | A1 | 12/2005 | Malamas et al. |
| 2005/0282826 | A1 | 12/2005 | Malamas et al. |
| 2006/0281729 | A1 | 12/2006 | Iserloh et al. |
| 2006/0287294 | A1 | 12/2006 | Zhu et al. |
| 2007/0004730 | A1 | 1/2007 | Zhou et al. |
| 2007/0004786 | A1 | 1/2007 | Malamas et al. |
| 2007/0049589 | A1 | 3/2007 | Thompson, III et al. |
| 2007/0099875 | A1 | 5/2007 | Zhu et al. |
| 2007/0099898 | A1 | 5/2007 | Zhu et al. |
| 2008/0171771 | A1 | 7/2008 | Arnold et al. |
| 2008/0287462 | A1 | 11/2008 | Chessari et al. |
| 2009/0082560 | A1 | 3/2009 | Kobayashi et al. |
| 2010/0125081 | A1 | 5/2010 | Holenz et al. |
| 2010/0125087 | A1 | 5/2010 | Holenz et al. |

FOREIGN PATENT DOCUMENTS

| | | |
|---|---|---|
| EP | 686673 A1 | 6/1995 |
| EP | 742217 A1 | 5/1996 |
| EP | 0855444 A2 | 7/1998 |
| WO | 9534563 A1 | 12/1995 |
| WO | 9911643 A1 | 3/1999 |
| WO | 0017369 A2 | 3/2000 |
| WO | 0047618 A2 | 8/2000 |
| WO | 0058479 A1 | 10/2000 |
| WO | 0077030 A1 | 12/2000 |
| WO | 0100663 A2 | 1/2001 |
| WO | 0100665 A2 | 1/2001 |
| WO | 0123533 A2 | 4/2001 |
| WO | 0129563 A1 | 4/2001 |
| WO | 0202505 A2 | 1/2002 |
| WO | 0202506 A2 | 1/2002 |
| WO | 0202512 A2 | 1/2002 |
| WO | 0202518 A2 | 1/2002 |
| WO | 0202520 A2 | 1/2002 |

(Continued)

OTHER PUBLICATIONS

Office action dated Mar. 19, 2009 in U.S. Appl. No. 12/120,736.

(Continued)

*Primary Examiner* — James O Wilson
*Assistant Examiner* — Douglas M Willis
(74) *Attorney, Agent, or Firm* — David M. Gryte

(57) ABSTRACT

The present invention relates to novel compounds of formula (I) and their pharmaceutical compositions. In addition, the present invention relates to therapeutic methods for the treatment and/or prevention of Aβ-related pathologies such as Downs syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

(I)

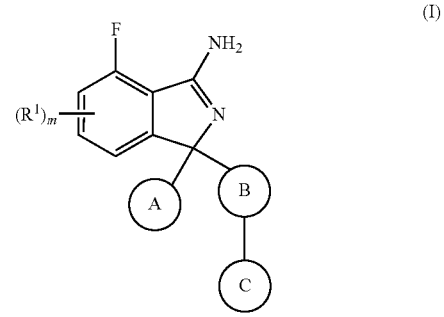

2 Claims, No Drawings

FOREIGN PATENT DOCUMENTS

| | | | |
|---|---|---|---|
| WO | 0214264 | A2 | 2/2002 |
| WO | 0225276 | A1 | 3/2002 |
| WO | 2005058311 | A1 | 6/2005 |
| WO | 2005097767 | A1 | 10/2005 |
| WO | 2005123672 | A2 | 12/2005 |
| WO | 2006009655 | A1 | 1/2006 |
| WO | 2006020879 | | 2/2006 |
| WO | 2006034419 | A2 | 3/2006 |
| WO | 2006041404 | A1 | 4/2006 |
| WO | 2006041405 | A1 | 4/2006 |
| WO | 2006065204 | A1 | 6/2006 |
| WO | 2006065277 | A2 | 6/2006 |
| WO | 2006076284 | A2 | 7/2006 |
| WO | 2006099379 | A2 | 9/2006 |
| WO | 2006138217 | A1 | 12/2006 |
| WO | 2006138230 | A2 | 12/2006 |
| WO | 2006138264 | A2 | 12/2006 |
| WO | 2006138265 | A2 | 12/2006 |
| WO | 2006138266 | A2 | 12/2006 |
| WO | 2007011810 | A1 | 1/2007 |
| WO | 2007011833 | A2 | 1/2007 |
| WO | 2007049532 | A1 | 5/2007 |
| WO | 2007058580 | A1 | 5/2007 |
| WO | 2007058581 | A1 | 5/2007 |
| WO | 2007058582 | A1 | 5/2007 |
| WO | 2007058583 | A2 | 5/2007 |
| WO | 2007058601 | A1 | 5/2007 |
| WO | 2007058602 | A2 | 5/2007 |
| WO | 2007073284 | A1 | 6/2007 |
| WO | 2007114771 | A1 | 10/2007 |
| WO | 2007120096 | A1 | 10/2007 |
| WO | 2007145568 | A1 | 12/2007 |
| WO | 2007145569 | A1 | 12/2007 |
| WO | 2007145570 | A1 | 12/2007 |
| WO | 2007145571 | A1 | 12/2007 |
| WO | 2007146225 | A1 | 12/2007 |
| WO | 2007149033 | A1 | 12/2007 |
| WO | 2008063114 | A1 | 5/2008 |
| WO | 2008076043 | A1 | 6/2008 |
| WO | 2008076044 | A1 | 6/2008 |
| WO | 2008076045 | A1 | 6/2008 |
| WO | 2008076046 | A1 | 6/2008 |
| WO | 2008150217 | A1 | 12/2008 |
| WO | 2009005470 | A1 | 1/2009 |
| WO | 2009005471 | A1 | 1/2009 |
| WO | 2010056194 | A1 | 5/2010 |
| WO | 2010056195 | A1 | 5/2010 |
| WO | 2011044181 | A1 | 4/2011 |
| WO | 2011044184 | A1 | 4/2011 |
| WO | 2011044185 | A2 | 4/2011 |
| WO | 2011044187 | A1 | 4/2011 |

OTHER PUBLICATIONS

Dorwald F. Z. Side Reactions in Organic Synthesis, A Guide to Successful Synthesis Design, Weinheim: Wiley-VCH Verlag GmBH & Co, KgaA, 2005, Preface.
Hussain et al., 1999, Mol Cell Neurosci. Dec 14(6), 419-427.
Jordan V. C., Nature Reviews, Mar. 2003, 2: 205-213.
Lin et. al, 2000, PNAS, 97(4), 1456-1460.
Owens M.J., Pharm Rev vol. 43, p. 425-473 (1991).
Oyama et al., 1994, J Neurochem, 62(3), 1062-1066.
Sinha et. al., 1999, Nature 402(6761), 537-540.
Vassar et. al., 1999, Science, 286(5440), 735-741.
Vippagunta et al. Crystalline Solids, 2001, Advanced Drug Delivery Reviews, 48, pp. 3 and 18.
Yan et. al, 1999, Nature 402(6761), 533-537.
Yankner, 1996, Nature Medicine, 2(8), 850-852.
Blanchard, Barbara; PNAS, Oct. 2004, 101(40), 14326-14332.
Barrett, P et al., J. Chem. Soc., 1939, 1809-20.
Bartlett, R et al., J. Chem. Soc. C, 1969, 1, 129-33.
Sawanishi et al., Chemical and Pharmaceutical Bulletin, 1985, 33(10), 4564-71.
Siling S. et al., Doklady Akademii Nauk SSSR, 1988, 299(3), 633-5.
De Strooper, Bart et al., A Firm Base for Drug Development, Dec. 1999, Nature 402, 1999, 471-472.
Von Angerer, S. "Product class 12: pyrimidines", Science of Synthesis, 2004, 16, 379-572.
English abstract of Siling S. et al., Doklady Akademii Nauk SSSR, 1988, 299(3), 633-5.
Office action dated Aug. 3, 2009, received in U.S. Appl. No. 11/762,487.
Karlström S et al., Poster entitled "BACE Inhibitor for the treatment of Alzheimer's disease", presented at 5th Anglo-Swedish Medicinal Chemistry Symposium 2011 in Åre, Sweden (Mar. 20-23, 2011).
Eketjäll S et al., Poster entitled "Reduction of Beta Amyloid Production In Vitro and In Vivo by Novel Small Molecule BACE1 Inhibitors", presented at the International Conference on Alzheimer's and Parkinson's Disease in Barcelona, Spain, (Mar. 9-13, 2011).
Eketjäll S et al., Poster entitled "Inhibitor of BACE1 Reduced Beta Amyloid Production in Guinea Pigs: Dose-Depentent Effects in Cerebrospinal Fluid and Brain", presented at the International Conference on Alzheimer's and Parkinson's Disease in Barcelona, Spain, (Mar. 9-13, 2011).
Fälting J et al., Poster entitled "BACE1 Inhibitors for the Treatment of Alzheimer's Disease", presented at the International Conference on Alzheimer's and Parkinson's Disease in Barcelona, Spain, (Mar. 9-13, 2011).

SUBSTITUTED ISOINDOLES FOR THE TREATMENT AND/OR PREVENTION OF Aβ-RELATED PATHOLOGIES

This patent claims the benefit of priority to U.S. Provisional Patent Application Nos. 61/114,634 (filed 14 Nov. 2008); 61/139,767 (filed 22 Dec. 2008); and 61/221,653 (filed 30 Jun. 2009). The entire text of each of the above-referenced patent applications is incorporated by reference into this patent.

TECHNICAL FIELD OF THE INVENTION

The present invention relates to novel compounds and their pharmaceutical compositions. In addition, the present invention relates to therapeutic methods for the treatment and/or prevention of Aβ-related pathologies such as Downs syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

BACKGROUND

Several groups have identified and isolated aspartate proteinases that have β-secretase activity (Hussain et al., 1999; Lin et. al, 2000; Yan et. al, 1999; Sinha et. al., 1999 and Vassar et. al., 1999). β-secretase is also known in the literature as Asp2 (Yan et. al, 1999), Beta site APP Cleaving Enzyme (BACE) (Vassar et. al., 1999) or memapsin-2 (Lin et al., 2000). BACE was identified using a number of experimental approaches such as EST database analysis (Hussain et al. 1999); expression cloning (Vassar et al. 1999); identification of human homologs from public databases of predicted *C. elegans* proteins (Yan et al. 1999) and finally utilizing an inhibitor to purify the protein from human brain (Sinha et al. 1999). Thus, five groups employing three different experimental approaches led to the identification of the same enzyme, making a strong case that BACE is a β-secretase. Mention is also made of the patent literature: WO96/40885, EP871720, U.S. Pat. Nos. 5,942,400 and 5,744,346, EP855444, U.S. Pat. No. 6,319,689, WO99/64587, WO99/31236, EP1037977, WO00/17369, WO01/23533, WO0047618, WO00/58479, WO00/69262, WO01/00663, WO01/00665 and U.S. Pat. No. 6,313,268.

BACE was found to be a pepsin-like aspartic proteinase, the mature enzyme consisting of the N-terminal catalytic domain, a transmembrane domain, and a small cytoplasmic domain. BACE has an optimum activity at pH 4.0-5.0 (Vassar et al, 1999) and is inhibited weakly by standard pepsin inhibitors such as pepstatin. It has been shown that the catalytic domain minus the transmembrane and cytoplasmic domain has activity against substrate peptides (Lin et al, 2000). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-protein (Aβ). It is thus of special interest in the pathology of Alzheimer's disease, and in the development of drugs as a treatment for Alzheimer's disease.

Aβ or amyloid-β-protein is the major constituent of the brain plaques which are characteristic of Alzheimer's disease (De Strooper et al, 1999). Aβ is a 39-42 residue peptide formed by the specific cleavage of a class 1 transmembrane protein called APP, or amyloid precursor protein. Cleavage of APP by BACE generates the extracellular soluble APPβ fragment and the membrane bound CTFβ (C99) fragment that is subsequently is cleaved by γ-secretase to generate Aβ peptide.

Alzheimer's disease (AD) is estimated to afflict more than 20 million people worldwide and is believed to be the most common form of dementia. Alzheimer's disease is a progressive dementia in which massive deposits of aggregated protein breakdown products—amyloid plaques and neurofibrillary tangles accumulate in the brain. The amyloid plaques are thought to be responsible for the mental decline seen in Alzheimer's patients.

The likelihood of developing Alzheimer's disease increases with age, and as the aging population of the developed world increases, this disease becomes a greater and greater problem. In addition to this, there is a familial link to Alzheimer's disease and consequently any individuals possessing the double mutation of APP known as the Swedish mutation (in which the mutated APP forms a considerably improved substrate for BACE) have a much higher risk of developing AD, and also of developing the disease at an early age (see also U.S. Pat. Nos. 6,245,964 and 5,877,399 pertaining to transgenic rodents comprising APP-Swedish). Consequently, there is also a strong need for developing a compound that can be used in a prophylactic fashion for these individuals.

The gene encoding APP is found on chromosome 21, which is also the chromosome found as an extra copy in Down's syndrome. Down's syndrome patients tend to develop Alzheimer's disease at an early age, with almost all those over 40 years of age showing Alzheimer's-type pathology (Oyama et al., 1994). This is thought to be due to the extra copy of the APP gene found in these patients, which leads to overexpression of APP and therefore to increased levels of Aβ causing the high prevalence of Alzheimer's disease seen in this population. Thus, inhibitors of BACE could be useful in reducing Alzheimer's-type pathology in Down's syndrome patients.

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof (Yankner, 1996; De Strooper and Konig, 1999). BACE is therefore an important candidate for the development of drugs as a treatment and/or prophylaxis of Aβ-related pathologies such as Downs syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors (see, e.g., WO01/23533 A2, EP0855444, WO00/17369, WO00/58479, WO00/47618, WO00/77030, WO01/00665, WO01/00663, WO01/29563, WO02/25276, U.S. Pat. Nos. 5,942,400, 6,245,884, 6,221,667, 6,211,235, WO02/02505, WO02/02506, WO02/02512, WO02/02518, WO02/02520, WO02/14264, WO05/058311, WO05/097767, WO06/041404, WO06/041405, WO06/0065204, WO06/0065277, US2006287294, WO06/138265, US20050282826, US20050282825, US20060281729, WO06/138217, WO06/138230, WO06/138264, WO06/138265, WO06/138266, WO06/099379, WO06/076284, US20070004786, US20070004730, WO07/011,833, WO07/011,810, US20070099875, US20070099898, WO07/058,601, WO07/058,581, WO07/058,580, WO07/058,583, WO07/058,582, WO07/058,602, WO07/073,284, WO07/049,532, WO07/038,271, WO07/016,012, WO07/005,366, WO07/005,404 and WO06/0009653.

OUTLINE OF THE INVENTION

The present invention relates to a compound according to formula (I):

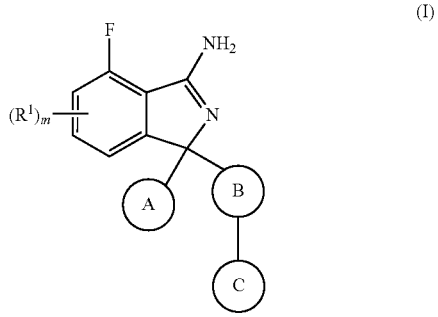

wherein
$R^1$ is selected from halogen, cyano, $NO_2$, $SO_2R^2$, $C_{1-6}$alkyl, $C_{2-6}$alkenyl, $C_{2-6}$alkynyl, $NR^3R^4$, $OR^2$, $C(O)R^2$, $C(O)NR^3R^4$ and $COOR^2$, wherein said $C_{1-6}$alkyl, $C_{2-6}$alkenyl or $C_{2-6}$alkynyl is optionally substituted with one or more $R^7$;
$R^2$ is $C_{1-6}$alkyl, $C_{2-6}$alkenyl or $C_{2-6}$alkynyl, wherein said $C_{1-6}$alkyl, $C_{2-6}$alkenyl or $C_{2-6}$alkynyl is optionally substituted with one or more $R^7$;
$R^3$ and $R^4$ are independently selected from hydrogen, $C_{1-6}$alkyl, $C_{2-6}$alkenyl, $C_{2-6}$alkynyl, aryl, heteroaryl, heterocyclyl and carbocyclyl, wherein said $C_{1-6}$alkyl, $C_{2-6}$alkenyl, $C_{2-6}$alkynyl, aryl, heteroaryl, heterocyclyl or carbocyclyl is optionally substituted with one or more $R^7$;
or $R^3$ and $R^4$ together with the atom they are attached to, form a 4 to 7 membered ring;
A is selected from aryl and heteroaryl, wherein said aryl or heteroaryl is optionally substituted with one or more $R^5$;
B is aryl or heteroaryl, wherein said aryl or heteroaryl is optionally substituted with one or more $R^6$;
C is selected from hydrogen, halogen, cyano, aryl, heteroaryl, heterocyclyl, $C_{3-6}$cycloalkyl, $C_{3-6}$cycloalkenyl, $C_{1-6}$alkyl, $C_{2-6}$alkenyl, $C_{2-6}$alkynyl, $C_{1-6}$alkyl$C_{3-6}$cycloalkyl, $C_{1-6}$alkyl$C_{3-6}$heterocyclyl, $C_{1-6}$alkylaryl, $C_{1-6}$alkylheteroaryl and $C_{2-6}$alkenyl$C_{3-6}$cycloalkyl, wherein said aryl, heteroaryl, heterocyclyl, $C_{3-6}$cycloalkyl, $C_{3-6}$cycloalkenyl, $C_{1-6}$alkyl, $C_{2-6}$alkenyl, $C_{2-6}$alkynyl, $C_{1-6}$alkyl$C_{3-6}$cycloalkyl, $C_{1-6}$alkyl$C_{3-6}$heterocyclyl, $C_{1-6}$alkylaryl, $C_{1-6}$alkylheteroaryl or $C_{2-6}$alkenyl$C_{3-6}$cycloalkyl is optionally substituted with one to three $R^7$;
$R^5$ is selected from halogen, cyano, $C_{1-6}$alkyl, $C_{1-6}$haloalkyl, $C_{3-6}$cycloalkyl, $OC_{1-6}$alkyl and $OC_{1-6}$alkylaryl, wherein said $C_{1-6}$alkyl, $C_{3-6}$cycloalkyl, $OC_{1-6}$alkyl or $OC_{1-6}$alkylaryl is optionally substituted with one to three $R^7$;
$R^6$ is halogen, hydroxy, methoxy, or cyano;
$R^7$ is selected from halogen, $C_{1-6}$alkyl, $SO_2C_{1-3}$alkyl, $OC_{1-3}$alkyl, $OC_{1-3}$haloalkyl, $C_{1-3}$alkylOH, $C_{1-3}$alkylNR$^8$R$^9$, OH, cyano, $C(O)OC_{1-3}$alkyl and $NR^8R^9$, wherein said $C_{1-6}$alkyl, $SO_2C_{1-3}$alkyl, $OC_{1-3}$alkyl, $OC_{1-3}$haloalkyl, $C_{1-3}$alkylOH, $C_{1-3}$alkylNR$^8$R$^9$ or $C(O)OC_{1-3}$alkyl is optionally substituted with one or more $R^{10}$;
$R^8$ and $R^9$ are independently selected from hydrogen, $C_{1-6}$alkyl, $C_{1-6}$haloalkyl, $C_{2-6}$alkenyl, $C_{2-6}$alkynyl, $C_{1-3}$alkylNR$^{11}$R$^{12}$, $C_{1-3}$alkylOaryl, heteroaryl, heterocyclyl and carbocyclyl, wherein said $C_{1-6}$alkyl, $C_{1-6}$haloalkyl, $C_{2-6}$alkenyl, $C_{2-6}$alkynyl, $C_{1-3}$alkylNR$^{11}$R$^{12}$, $C_{1-3}$alkylOaryl, heteroaryl, heterocyclyl or carbocyclyl is optionally substituted with one or more $R^{10}$;
or $R^8$ and $R^9$ together with the atom they are attached to form a 4 to 6 membered ring;
$R^{10}$ is selected from halo, $C_{1-3}$alkyl, $OC_{1-3}$alkyl and $OC_{1-3}$haloalkyl;
$R^{11}$ and $R^{12}$ are independently selected from hydrogen $C_{1-3}$alkyl and $C_{1-3}$haloalkyl;
m is 0, 1 or 2;
with the provisio that when C is $C_{1-6}$alkyl then $R^7$ is not $OC_{1-3}$alkyl or $OC_{1-3}$haloalkyl;
as a free base or a pharmaceutically acceptable salt thereof.
According to one embodiment of the present invention,
$R^1$ is selected from halogen, cyano, $NO_2$, $SO_2R^2$, $C_{1-6}$alkyl, $NR^3R^4$, $OR^2$, $C(O)R^2$, $C(O)NR^3R^4$ and $COOR^2$, wherein said $C_{1-6}$alkyl is optionally substituted with one or more $R^7$;
$R^2$ is $C_{1-6}$alkyl, $C_{2-6}$alkenyl or $C_{2-6}$alkynyl, wherein said $C_{1-6}$alkyl, $C_{2-6}$alkenyl or $C_{2-6}$alkynyl is optionally substituted with one or more $R^7$;
$R^3$ and $R^4$ are independently selected from hydrogen, $C_{1-6}$alkyl, aryl, heteroaryl, heterocyclyl and carbocyclyl, wherein said $C_{1-6}$alkyl, $C_{2-6}$alkenyl, $C_{2-6}$alkynyl, aryl, heteroaryl, heterocyclyl or carbocyclyl is optionally substituted with one or more $R^7$;
or $R^3$ and $R^4$ together with the atom they are attached to, form a 4 to 7 membered ring;
A is selected from aryl and heteroaryl, wherein said aryl or heteroaryl is optionally substituted with one or more $R^5$;
B is aryl or heteroaryl, wherein said aryl or heteroaryl is optionally substituted with one or more $R^6$;
C is selected from halogen, cyano, aryl, heteroaryl, heterocyclyl, $C_{3-6}$cycloalkyl, $C_{3-6}$cycloalkenyl, $C_{1-6}$alkyl, $C_{2-6}$alkenyl, $C_{2-6}$alkynyl, $C_{1-6}$alkyl$C_{3-6}$cycloalkyl, $C_{1-6}$alkyl$C_{3-6}$heterocyclyl, $C_{1-6}$alkylaryl, $C_{1-6}$alkylheteroaryl and $C_{2-6}$alkenyl$C_{3-6}$cycloalkyl, wherein said aryl, heteroaryl, heterocyclyl, $C_{3-6}$cycloalkyl, $C_{3-6}$cycloalkenyl, $C_{1-6}$alkyl, $C_{2-6}$alkenyl, $C_{2-6}$alkynyl, $C_{1-6}$alkyl$C_{3-6}$cycloalkyl, $C_{1-6}$alkyl$C_{3-6}$heterocyclyl, $C_{1-6}$alkylaryl, $C_{1-6}$alkylheteroaryl or $C_{2-6}$alkenyl$C_{3-6}$cycloalkyl is optionally substituted with one to three $R^7$;
$R^5$ is selected from halogen, cyano, $C_{1-6}$alkyl, $C_{1-6}$haloalkyl, $C_{3-6}$cycloalkyl, $OC_{1-6}$alkyl and $OC_{1-6}$alkylaryl, wherein said $C_{1-6}$alkyl, $C_{3-6}$cycloalkyl, $OC_{1-6}$alkyl or $OC_{1-6}$alkylaryl is optionally substituted with one to three $R^7$;
$R^6$ is halogen, hydroxy, methoxy or cyano;
$R^7$ is selected from halogen, $C_{1-6}$alkyl, $SO_2C_{1-3}$alkyl, $OC_{1-3}$alkyl, $OC_{1-3}$haloalkyl, $C_{1-3}$alkylOH, $C_{1-3}$alkylNR$^8$R$^9$, OH, cyano, $C(O)OC_{1-3}$alkyl and $NR^8R^9$, wherein said $C_{1-6}$alkyl, $SO_2C_{1-3}$alkyl, $OC_{1-3}$alkyl, $OC_{1-3}$haloalkyl, $C_{1-3}$alkylOH, $C_{1-3}$alkylNR$^8$R$^9$ or $C(O)OC_{1-3}$alkyl is optionally substituted with one or more R$^{10}$;

R$^8$ and R$^9$ are independently selected from hydrogen, $C_{1-6}$alkyl, $C_{1-6}$haloalkyl, $C_{1-3}$alkylNR$^{11}$R$^{12}$, $C_{1-3}$alkylO aryl, heteroaryl, heterocyclyl and carbocyclyl, wherein said $C_{1-6}$alkyl, $C_{1-6}$haloalkyl, $C_{1-3}$alkylNR$^{11}$R$^{12}$, $C_{1-3}$alkylOaryl, heteroaryl, heterocyclyl or carbocyclyl is optionally substituted with one or more R$^{10}$;

or R$^8$ and R$^9$ together with the atom they are attached to form a 4 to 6 membered ring;

R$^{10}$ is selected from halo, $C_{1-3}$alkyl, $OC_{1-3}$alkyl and $OC_{1-3}$haloalkyl;

R$^{11}$ and R$^{12}$ are independently selected from hydrogen $C_{1-3}$alkyl and $C_{1-3}$haloalkyl;

m is 0, 1 or 2.

According to one embodiment of the present invention,

R$^1$ is selected from halogen, cyano, NO$_2$, SO$_2$R$^2$, $C_{1-6}$alkyl, NR$^3$R$^4$, OR$^2$, C(O)R$^2$ and COOR$^2$, wherein said $C_{1-6}$alkyl is optionally substituted with one or more R$^7$;

R$^2$ is $C_{1-6}$alkyl, wherein said $C_{1-6}$alkyl is optionally substituted with one or more R$^7$;

R$^3$ and R$^4$ are independently selected from hydrogen, $C_{1-6}$alkyl, aryl, heteroaryl, heterocyclyl and carbocyclyl, wherein said $C_{1-6}$alkyl, $C_{2-6}$alkenyl, $C_{2-6}$alkynyl, aryl, heteroaryl, heterocyclyl or carbocyclyl is optionally substituted with one or more R$^7$;

A is selected from aryl and heteroaryl, wherein said aryl or heteroaryl is optionally substituted with one or more R$^5$;

B is aryl or heteroaryl, wherein said aryl or heteroaryl is optionally substituted with one or more R$^6$;

C is selected from halogen, cyano, aryl, heteroaryl, heterocyclyl, $C_{3-6}$cycloalkyl, $C_{3-6}$cycloalkenyl, $C_{1-6}$alkyl, $C_{1-6}$alkylC$_{3-6}$cycloalkyl, $C_{1-6}$alkylC$_{3-6}$heterocyclyl, $C_{1-6}$alkylaryl and $C_{1-6}$alkylheteroaryl, wherein said aryl, heteroaryl, heterocyclyl, $C_{3-6}$cycloalkyl, $C_{3-6}$cycloalkenyl, $C_{1-6}$alkyl, $C_{1-6}$alkylC$_{3-6}$cycloalkyl, $C_{1-6}$alkylC$_{3-6}$heterocyclyl, $C_{1-6}$alkylaryl or $C_{1-6}$alkylheteroaryl is optionally substituted with one to three R$^7$;

R$^5$ is selected from halogen, cyano, $C_{1-6}$alkyl, $C_{1-6}$haloalkyl, $C_{3-6}$cycloalkyl, $OC_{1-6}$alkyl and $OC_{1-6}$alkylaryl, wherein said $C_{1-6}$alkyl, $C_{3-6}$cycloalkyl, $OC_{1-6}$alkyl or $OC_{1-6}$alkylaryl is optionally substituted with one to three R$^7$;

R$^6$ is halogen or hydroxy;

R$^7$ is selected from halogen, $C_{1-6}$alkyl, $SO_2C_{1-3}$alkyl, $OC_{1-3}$alkyl, $OC_{1-3}$haloalkyl, $C_{1-3}$alkylOH, cyano, $C(O)OC_{1-3}$alkyl and NR$^8$R$^9$, wherein said $C_{1-6}$alkyl, $SO_2C_{1-3}$alkyl, $OC_{1-3}$alkyl, $OC_{1-3}$haloalkyl, $C_{1-3}$alkylOH or $C(O)OC_{1-3}$alkyl is optionally substituted with one or more R$^{10}$;

R$^8$ and R$^9$ are independently selected from hydrogen, $C_{1-6}$alkyl, $C_{1-6}$haloalkyl, $C_{1-3}$alkylNR$^{11}$R$^{12}$, $C_{1-3}$alkylO aryl, heteroaryl, heterocyclyl and carbocyclyl, wherein said $C_{1-6}$alkyl, $C_{1-6}$haloalkyl, $C_{1-3}$alkylNR$^{11}$R$^{12}$, $C_{1-3}$alkylOaryl, heteroaryl, heterocyclyl or carbocyclyl is optionally substituted with one or more R$^{10}$;

R$^{10}$ is selected from halo, $C_{1-3}$alkyl, $OC_{1-3}$alkyl and $OC_{1-3}$haloalkyl;

R$^{11}$ and R$^{12}$ are independently selected from hydrogen $C_{1-3}$alkyl and $C_{1-3}$haloalkyl;

m is 0 or 1.

According to one embodiment of the present invention, A is heteroaryl

According to another embodiment of the present invention, said heteroaryl is pyridyl or pyrimidyl.

According to one embodiment of the present invention, A is aryl.

According to another embodiment of the present invention, said aryl is phenyl.

According to one embodiment of the present invention, A is not substituted.

According to one embodiment of the present invention, A is substituted with one or more R$^5$.

According to another embodiment of the present invention, R$^5$ is cyano, $C_{1-6}$alkyl, $C_{1-6}$haloalkyl, $C_{3-6}$cycloalkyl or $OC_{1-6}$ alkyl, wherein said $C_{1-6}$alkyl is optionally substituted with one to three R$^7$.

According to one embodiment of the present invention, B is aryl.

According to another embodiment of the present invention, said aryl is phenyl.

According to one embodiment of the present invention, B is heteroaryl.

According to another embodiment of the present invention, said heteroaryl is pyridyl.

According to one embodiment of the present invention, B is not substituted.

According to one embodiment of the present invention, B is substituted with one R$^6$.

According to another embodiment of the present invention, R$^6$ is fluoro.

According to another embodiment of the present invention, R$^6$ is hydroxy.

According to one embodiment of the present invention, C is selected from halogen, cyano, aryl, heteroaryl, $C_{3-6}$cycloalkyl, $C_{1-6}$alkyl, $C_{1-6}$alkylC$_{3-6}$cycloalkyl, $C_{1-6}$alkylC$_{3-6}$heterocyclyl, $C_{1-6}$alkylaryl and $C_{1-6}$alkylheteroaryl, wherein said aryl, heteroaryl, $C_{3-6}$cycloalkyl, $C_{1-6}$alkyl, $C_{1-6}$alkylC$_{3-6}$cycloalkyl, $C_{1-6}$alkylC$_{3-6}$heterocyclyl, $C_{1-6}$alkylaryl or $C_{1-6}$alkylheteroaryl is optionally substituted with one to three R$^7$;

According to one embodiment of the present invention, C is aryl or heteroaryl.

According to another embodiment of the present invention, said aryl is phenyl.

According to another embodiment of the present invention, said heteroaryl is selected from pyrimidyl and pyridyl.

According to one embodiment of the present invention, C is not substituted.

According to one embodiment of the present invention, C is substituted with one to three R$^7$.

According to another embodiment of the present invention, R$^7$ is selected from halogen, $C_{1-6}$alkyl, $SO_2C_{1-3}$alkyl, $OC_{1-3}$alkyl, $OC_{1-3}$haloalkyl and cyano.

According to one embodiment of the present invention, m is 0.

According to one embodiment of the present invention,
m is 0;
A is not pyridyl substituted with CH$_3$;
B is not phenyl substituted with fluoro;
C is not pyridyl substituted with SO$_2$CH$_3$.

According to one embodiment of the present invention,
A is selected from aryl and heteroaryl, wherein said aryl or heteroaryl is optionally substituted with one or more R$^5$;
B is aryl or heteroaryl, wherein said aryl or heteroaryl is optionally substituted with one more R$^6$;
C is selected from aryl and heteroaryl, wherein said aryl or heteroaryl is optionally substituted with one to three R$^7$;
R$^5$ is selected from halogen, cyano, $C_{1-6}$alkyl, $C_{1-6}$haloalkyl, $C_{3-6}$cycloalkyl and $OC_{1-6}$alkyl and wherein said $C_{1-6}$alkyl is optionally substituted with one R$^7$;
R$^6$ is halogen or hydroxy;

$R^7$ is selected from halogen, $C_{1-6}$alkyl, $SO_2C_{1-3}$alkyl, $OC_{1-3}$alkyl, $OC_{1-3}$haloalkyl, cyano;

m is 0.

According to another embodiment of the present invention, A is pyridyl, pyrimidyl or phenyl.

According to another embodiment of the present invention, B is pyridyl or phenyl.

According to another embodiment of the present invention, C is phenyl, pyridyl or pyrimidyl.

According to another embodiment of the present invention,

A is heteroaryl substituted with one $R^5$;

B is aryl;

C is heteroaryl.

The present invention also relates to a compound according to formula (Ia)

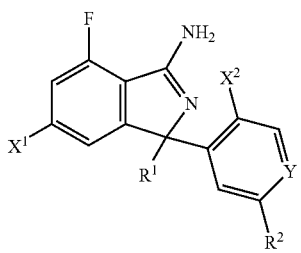

Ia wherein $R^1$ is selected from phenyl, pyridyl, pyrimidinyl, (phenyl)phenyl, (pyridyl)phenyl, (pyrazin)phenyl, (pyrimidinyl)phenyl, wherein all groups are optionally and independently substituted with one to three R' groups;

$R^2$ is selected from hydrogen, $C_{3-6}$cycloalkyl, $C_{1-6}$alkyl, halogenated $C_{1-6}$alkyl, $C_{1-6}$alkoxy, halogenated $C_{1-6}$alkoxy, pyridyl, pyrimidinyl, phenyl, wherein the phenyl, pyridyl, and pyrimidinyl groups are optionally and independently substituted with one to three R' groups or hydroxy, $SO_2C_{1-6}$alkyl, and $C_{3-6}$cycloalkyl;

R' is selected from halogen, $C_{1-6}$alkyl, halogenated $C_{1-6}$alkyl, $C_{1-6}$alkoxy, halogenated $C_{1-6}$alkoxy, cyano, and cyanomethyl;

Y is selected from N, CH and CF; and $X^1$ and $X^2$ are independently selected from hydrogen, chloro and fluoro, or a pharmaceutically acceptable salt thereof.

Further, one embodiment of the present invention is a compound of formula Ia wherein $R^1$ is selected from phenyl, 4-pyridyl, 3-pyridyl, 2-pyridyl, pyrimidin-5-yl, pyrimidin-4-yl, 3-(phenyl)phenyl, 3-(2-pyridyl)phenyl, 3-(3-pyridyl)phenyl, 3-pyrazin-2-ylphenyl, 3-pyrimidin-5-yl-phenyl, 3-pyrazin-2-yl-phenyl, wherein all rings are optionally and independently substituted with one to three R' groups, hydroxy, $SO_2C_{1-6}$alkyl, or $C_{3-6}$cycloalkyl;

$R^2$ is selected from hydrogen, $C_{3-6}$cycloalkyl, $C_{1-6}$alkyl, halogenated $C_{1-6}$alkyl, $C_{1-6}$alkoxy, halogenated $C_{1-6}$alkoxy, 3-pyridyl, pyrimidin-5-yl, phenyl, and 2-pyridyl, wherein the phenyl, pyridyl, and pyrimidinyl groups are optionally and independently substituted with one to three R' groups;

R' is selected from halogen, $C_{1-6}$alkyl, halogenated $C_{1-6}$alkyl, $C_{1-6}$alkoxy, halogenated $C_{1-6}$alkoxy, cyano, and cyanomethyl;

Y is selected from N, CH and CF; and $X^1$ and $X^2$ are independently selected from hydrogen, chloro and fluoro, or a pharmaceutically acceptable salt thereof.

Further, one embodiment of the present invention is a compound of formula Ia wherein $R^1$ is selected from 4-methoxyphenyl, 2,6-dimethyl-4-pyridyl, 2-(difluoromethyl)-6-methyl-4-pyridyl, 3-cyano-4-methoxy-phenyl, 3-(cyanomethyl)-4-methoxy-5-methyl-phenyl, 6-methoxy-5-(trifluoromethyl)-3-pyridyl, 3-cyano-4-methoxy-5-methyl-phenyl, 2-(trifluoromethyl)-4-pyridyl, 4-pyridyl, pyrimidin-5-yl, 2-methoxy-4-pyridyl, 2-methyl-4-pyridyl, 2-(difluoromethyl)-4-pyridyl, 2-cyclopropyl-4-pyridyl, 3-(2-fluoro-3-methoxy-phenyl)phenyl, 3-(3-chlorophenyl)phenyl, 3-(4-cyano-2-pyridyl)phenyl, 3-(4-methoxy-2-pyridyl)phenyl, 3-(5-cyano-3-pyridyl)phenyl, 3-(5-fluoro-3-pyridyl)phenyl, 3-fluoro-4-methoxy-5-methyl-phenyl, 3-pyrazin-2-ylphenyl, 3-pyrimidin-5-ylphenyl, 4-hydroxy-3-pyrazin-2-yl-phenyl, 4-methoxy-3,5-dimethyl-phenyl, 4-methoxy-3-pyrimidin-5-yl-phenyl, 5-(difluoromethoxy)-4,6-dimethyl-2-pyridyl, 3,4-difluoro-5-methoxyphenyl 2,6-dimethylpyrimidin-4-yl and 5-methoxy-4,6-dimethyl-2-pyridyl;

$R^2$ is selected from hydrogen, cyclopropyl, difluoromethyl, methoxy, trifluoromethyl, 5-cyano-3-pyridyl, pyrimidin-5-yl, 2-fluoro-3-methoxy-phenyl, 4-methoxy-2-pyridyl, 5-methylsulfonyl-3-pyridyl, 5-fluoro-3-pyridyl, and 3-pyridyl;

Y is selected from N, CH and CF; and $X^1$ and $X^2$ are independently selected from hydrogen, chloro and fluoro, or a pharmaceutically acceptable salt thereof.

The present invention also relates to a compound according to formula (Ib)

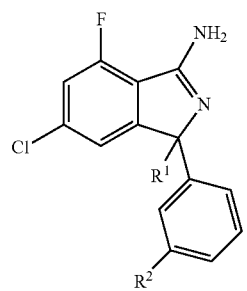

Ib wherein $R^1$ is selected from 4-pyridyl optionally substituted with one R' group;

$R^2$ is selected from pyrimidin-5-yl, optionally substituted with one R' group; and R' is selected from halogen, $C_{1-6}$alkyl, halogenated $C_{1-6}$alkyl, $C_{1-6}$alkoxy, halogenated $C_{1-6}$alkoxy, cyano, and cyanomethyl, or a pharmaceutically acceptable salt thereof.

Further, one embodiment of the present invention is a compound of formula Ib wherein $R^1$ is selected from 2-(trifluoromethyl)-4-pyridyl and 2-methyl-4-pyridyl; and $R^2$ is selected from pyrimidin-5-yl, or a pharmaceutically acceptable salt thereof.

The present invention also relates to a compound according to formula (Ic)

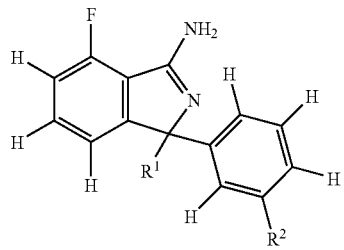

Ic wherein R¹ is selected from phenyl, pyridyl, and pyrimidinyl, wherein all groups are optionally and independently substituted with one to three R' groups or SO₂C₁₋₆alkyl;

R² is selected from pyridyl and pyrimidinyl, wherein both groups are optionally and independently substituted with one to three R' groups; and R' is selected from halogen, $C_{1-6}$alkyl, halogenated $C_{1-6}$alkyl, $C_{1-6}$alkoxy, halogenated $C_{1-6}$alkoxy, cyano, and cyanomethyl, or a pharmaceutically acceptable salt thereof.

Further, one embodiment of the present invention is a compound of formula Ic wherein R¹ is selected from phenyl, 4-pyridyl, 2-pyridyl, pyrimidin-4-yl, 3-pyridyl, wherein all groups are optionally and independently substituted with one to three R' groups or SO₂C₁₋₆alkyl;

R² is selected from 3-pyridyl and pyrimidin-5-yl, wherein both groups are optionally and independently substituted with one to three R' groups; and R' is selected from halogen, $C_{1-6}$alkyl, halogenated $C_{1-6}$alkyl, $C_{1-6}$alkoxy, halogenated $C_{1-6}$alkoxy, cyano, and cyanomethyl, or a pharmaceutically acceptable salt thereof.

Further, one embodiment of the present invention is a compound of formula Ic wherein R¹ is selected from 4-methoxyphenyl, 2,6-dimethyl-4-pyridyl, 2-(difluoromethyl)-6-methyl-4-pyridyl, 3-cyano-4-methoxy-phenyl, 5-methoxy-4,6-dimethyl-2-pyridyl, 2,6-dimethylpyrimidin-4-yl, 3-(cyanomethyl)-4-methoxy-5-methyl-phenyl, 6-methoxy-5-(trifluoromethyl)-3-pyridyl, and 3-cyano-4-methoxy-5-methyl-phenyl; and R² is selected from 5-cyano-3-pyridyl and pyrimidin-5-yl, or a pharmaceutically acceptable salt thereof.

The present invention also relates to a compound according to formula (Id)

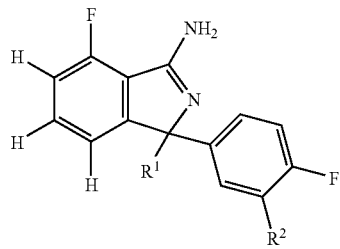

Id wherein R¹ is selected from pyridyl, pyrimidinyl, and (pyrimidin)phenyl, and all groups are optionally and independently substituted with one to three R' groups;

R² is selected from pyrimidinyl, phenyl, pyridyl, and methoxy, wherein the pyrimidinyl, phenyl, and pyridyl groups are optionally and independently substituted with one to three R' groups; and R' is selected from halogen, $C_{1-6}$alkyl, halogenated $C_{1-6}$alkyl, $C_{1-6}$alkoxy, halogenated $C_{1-6}$alkoxy, cyano, and cyanomethyl, or a pharmaceutically acceptable salt thereof.

Further, one embodiment of the present invention is a compound of formula Id wherein R¹ is selected from 4-pyridyl, pyrimidin-5-yl, and 3-pyrimidin-5-ylphenyl, and all groups are optionally and independently substituted with one to three R' groups;

R² is selected from pyrimidin-5-yl, phenyl, 2-pyridyl, 3-pyridyl, and methoxy, wherein the pyrimidin-5-yl, phenyl, 2-pyridyl, 3-pyridyl groups are optionally and independently substituted with one to three R' groups; and R' is selected from halogen, $C_{1-6}$alkyl, halogenated $C_{1-6}$alkyl, $C_{1-6}$alkoxy, halogenated $C_{1-6}$alkoxy, cyano, and cyanomethyl, or a pharmaceutically acceptable salt thereof.

Further, one embodiment of the present invention is a compound of formula Id wherein R¹ is selected from 2-(trifluoromethyl)-4-pyridyl, 4-pyridyl, pyrimidin-5-yl, 2-methoxy-4-pyridyl, and 3-pyrimidin-5-ylphenyl; and R² is selected from pyrimidin-5-yl, 2-fluoro-3-methoxy-phenyl, 4-methoxy-2-pyridyl, 5-cyano-3-pyridyl, and methoxy, or pharmaceutically acceptable salt thereof.

The present invention also relates to a compound according to formula (Ie)

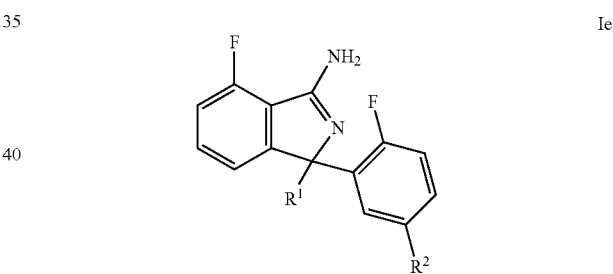

Ie wherein R¹ is pyridyl, optionally substituted with one to three R' groups;

R² is selected from pyrimidinyl and pyridyl, wherein both groups are optionally substituted with one to three R' groups; and R' is selected from halogen, $C_{1-6}$alkyl, halogenated $C_{1-6}$alkyl, $C_{1-6}$alkoxy, halogenated $C_{1-6}$alkoxy, cyano, and cyanomethyl, or a pharmaceutically acceptable salt thereof.

Further, one embodiment of the present invention is a compound of formula Ie wherein R¹ is 4-pyridyl, optionally substituted with one to three R' groups;

R² is selected from pyrimidin-5-yl and 3-pyridyl, wherein both groups are optionally substituted with one to three R' groups; and R' is selected from halogen, $C_{1-6}$alkyl, halogenated $C_{1-6}$alkyl, $C_{1-6}$alkoxy, halogenated $C_{1-6}$alkoxy, cyano, and cyanomethyl, or a pharmaceutically acceptable salt thereof.

Further, one embodiment of the present invention is a compound of formula Ie wherein
$R^1$ is selected from 2-methyl-4-pyridyl and 2-(trifluoromethyl)-4-pyridyl; and
$R^2$ is selected from pyrimidin-5-yl, 5-methylsulfonyl-3-pyridyl, 5-cyano-3-pyridyl, 5-fluoro-3-pyridyl, and 3-pyridyl,
or a pharmaceutically acceptable salt thereof.

The present invention also relates to a compound according to formula (If)

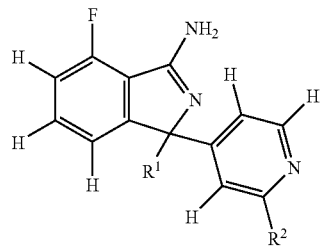

If wherein $R^1$ is selected from pyridyl, (phenyl)phenyl, (pyridyl)phenyl, phenyl, pyrazinylphenyl, pyrimidinylphenyl, wherein all groups are optionally and independently substituted by one to three R' groups;
$R^2$ is selected from hydrogen, pyridyl, $C_{3-6}$cycloalkyl, $C_{1-6}$alkyl, halogenated $C_{1-6}$alkyl, $C_{1-6}$alkoxy, halogenated $C_{1-6}$alkoxy, difluoromethyl, methoxy, pyrimidinyl, and trifluoromethyl, wherein the pyridyl and pyrimidinyl groups are optionally and independently substituted by one to three R' groups; and
R' is selected from halogen, $C_{1-6}$alkyl, halogenated $C_{1-6}$alkyl, $C_{1-6}$alkoxy, halogenated $C_{1-6}$alkoxy, cyano, and cyanomethyl,
or pharmaceutically acceptable salt thereof.

Further, one embodiment of the present invention is a compound of formula If wherein
$R^1$ is selected from pyridyl, (phenyl)phenyl, (pyridyl)phenyl, phenyl, pyrazinylphenyl, pyrimidinylphenyl, wherein all groups are optionally and independently substituted by one to three R' groups;
$R^2$ is selected from hydrogen, pyridyl, cyclopropyl, difluoromethyl, methoxy, pyrimidinyl, and trifluoromethyl, wherein the pyridyl and pyrimidinyl are optionally and independently substituted by one to three R' groups; and
R' is selected from halogen, $C_{1-6}$alkyl, halogenated $C_{1-6}$alkyl, $C_{1-6}$alkoxy, halogenated $C_{1-6}$alkoxy, cyano, and cyanomethyl,
or a pharmaceutically acceptable salt thereof.

Further, one embodiment of the present invention is a compound of formula If wherein
$R^1$ is selected from 4-pyridyl, 3-(phenyl)phenyl, 3-(2-pyridyl)phenyl, 3-(3-pyridyl)phenyl, phenyl, 3-pyrazin-2-ylphenyl, 3-pyrimidin-5-ylphenyl, 2-pyridyl, wherein all rings are optionally and independently substituted by one to three R' groups;
$R^2$ is selected from hydrogen, 3-pyridyl, cyclopropyl, difluoromethyl, methoxy, pyrimidin-5-yl, and trifluoromethyl, wherein the 3-pyridyl and pyrimidin-5-yl are optionally and independently substituted by one to three R' groups; and
R' is selected from halogen, $C_{1-6}$alkyl, halogenated $C_{1-6}$alkyl, $C_{1-6}$alkoxy, halogenated $C_{1-6}$alkoxy, cyano, and cyanomethyl,
or a pharmaceutically acceptable salt thereof.

Further, one embodiment of the present invention is a compound of formula If wherein
$R^1$ is selected from 2-(difluoromethyl)-4-pyridyl, 2-(difluoromethyl)-6-methyl-4-pyridyl, 2-cyclopropyl-4-pyridyl, 3-(2-fluoro-3-methoxy-phenyl)phenyl, 3-(3-chlorophenyl)phenyl, 3-(4-cyano-2-pyridyl)phenyl, 3-(4-methoxy-2-pyridyl)phenyl, 3-(5-cyano-3-pyridyl)-phenyl, 3-(5-fluoro-3-pyridyl)phenyl, 3-fluoro-4-methoxy-5-methyl-phenyl, 3-pyrazin-2-ylphenyl, 3-pyrimidin-5-ylphenyl, 4-hydroxy-3-pyrazin-2-yl-phenyl, 4-methoxy-3,5-dimethyl-phenyl, 4-methoxy-3-pyrimidin-5-yl-phenyl, 5-(difluoromethoxy)-4,6-dimethyl-2-pyridyl, and 5-methoxy-4,6-dimethyl-2-pyridyl;
$R^2$ is selected from hydrogen, 5-fluoro-3-pyridyl, cyclopropyl, difluoromethyl, methoxy, pyrimidin-5-yl, and trifluoromethyl,
or a pharmaceutically acceptable salt thereof.

The present invention also relates to a compound selected from
4-Fluoro-1-(2-fluoro-5-(pyrimidin-5-yl)phenyl)-1-(2-methylpyridin-4-yl)-1H-isoindol-3-amine;
5-(3-(3-Amino-4-fluoro-1-(2-methylpyridin-4-yl)-1H-isoindol-1-yl)-4-fluorophenyl)nicotinonitrile;
4-Fluoro-1-(2-fluoro-5-(5-fluoropyridin-3-yl)phenyl)-1-(2-methylpyridin-4-yl)-1H-isoindol-3-amine;
4-Fluoro-1-(2-fluoro-5-(pyridin-3-yl)phenyl)-1-(2-methylpyridin-4-yl)-1H-isoindol-3-amine;
4-Fluoro-1-(2-fluoro-5-(pyrimidin-5-yl)phenyl)-1-(2-(trifluoromethyl)pyridin-4-yl)-1H-isoindol-3-amine;
5-(3-(3-Amino-4-fluoro-1-(2-(trifluoromethyl)pyridin-4-yl)-1H-isoindol-1-yl)-4-fluorophenyl)nicotinonitrile;
4-Fluoro-1-(2-fluoro-5-(5-(methylsulfonyl)pyridin-3-yl)phenyl)-1-(2-(trifluoromethyl)pyridin-4-yl)-1H-isoindol-3-amine;
1-(3'-Chlorobiphenyl-3-yl)-4-fluoro-1-(pyridin-4-yl)-1H-isoindol-3-amine;
4-Fluoro-1-(pyridin-4-yl)-1-(3-(pyrimidin-5-yl)phenyl)-1H-isoindol-3-amine;
(R) and (S) 4-Fluoro-1-(pyridin-4-yl)-1-(3-(pyrimidin-5-yl)phenyl)-1H-isoindol-3-amine,
4-Fluoro-1-(4-fluoro-3-(pyrimidin-5-yl)phenyl)-1-(2-(trifluoromethyl)pyridin-4-yl)-1H-isoindol-3-amine;
(R) and (S) 4-Fluoro-1-(4-fluoro-3-(pyrimidin-5-yl)phenyl)-1-(2-(trifluoromethyl)pyridin-4-yl)-1H-isoindol-3-amine;
4-Fluoro-1-(2'-fluoro-3'-methoxybiphenyl-3-yl)-1-(pyridin-4-yl)-1H-isoindol-3-amine;
4-Fluoro-1-(3-(5-fluoropyridin-3-yl)phenyl)-1-(pyridin-4-yl)-1H-isoindol-3-amine;
4-Fluoro-1-(4-fluoro-3-(pyrimidin-5-yl)phenyl)-1-(pyridin-4-yl)-1H-isoindol-3-amine;
4-Fluoro-1-(4-methoxyphenyl)-1-(3-(pyrimidin-5-yl)phenyl)-1H-isoindol-3-amine;
1-(2',6-Difluoro-3'-methoxybiphenyl-3-yl)-4-fluoro-1-(pyrimidin-5-yl)-1H-isoindol-3-amine;
4-Fluoro-1-(4-fluoro-3-(4-methoxypyridin-2-yl)phenyl)-1-(pyrimidin-5-yl)-1H-isoindol-3-amine;
4-Fluoro-1-(3-(pyrimidin-5-yl)phenyl)-1-(2-(trifluoromethyl)pyridin-4-yl)-1H-isoindol-3-amine;
1-(2',6-Difluoro-3'-methoxybiphenyl-3-yl)-4-fluoro-1-(pyrimidin-5-yl)-1H-isoindol-3-amine;
5-(3-(3-Amino-1-(2,6-dimethylpyridin-4-yl)-4-fluoro-1H-isoindol-1 yl)phenyl)nicotinonitrile;
5-(3-(3-Amino-4-fluoro-1-(2-(trifluoromethyl)pyridin-4-yl)-1H-isoindol-1-yl)phenyl)nicotinonitrile;
4-Fluoro-1-(4-fluoro-3-(pyrimidin-5-yl)phenyl)-1-(2-methoxypyridin-4-yl)-1H-isoindol-3-amine;

5-(5-(3-Amino-4-fluoro-1-(2-(trifluoromethyl)pyridin-4-yl)-1H-isoindol-1-yl)-2-fluorophenyl)nicotinonitrile;

5-(5-(3-Amino-4-fluoro-1-(pyridin-4-yl)-1H-isoindol-1-yl)-2-fluorophenyl)nicotinonitrile;

4-Fluoro-1-(2-methoxypyridin-4-yl)-1-(3-(pyrimidin-5-yl)phenyl)-1H-isoindol-3-amine;

5-(3-(3-amino-4-fluoro-1-(2-methoxypyridin-4-yl)-1H-isoindol-1-yl)phenyl)nicotinonitrile;

4-Fluoro-1-(2-methoxypyridin-4-yl)-1-(3-(pyrazin-2-yl)phenyl)-1H-isoindol-3-amine; and 4-Fluoro-1-(3-(pyrazin-2-yl)phenyl)-1-(2-(trifluoromethyl)pyridin-4-yl)-1H-isoindol-3-amine;

1-(2-Cyclopropylpyridin-4-yl)-4-fluoro-1-(3-(pyrimidin-5-yl)phenyl)-1H-isoindol-3-amine;

1-(2-(Difluoromethyl)-6-methylpyridin-4-yl)-4-fluoro-1-(3-(pyrimidin-5-yl)phenyl)-1H-isoindol-3-amine;

1-(2-(Difluoromethyl)-6-methylpyridin-4-yl)-4-fluoro-1-(2-(pyrimidin-5-yl)pyridin-4-yl)-1H-isoindol-3-amine;

4-Fluoro-1-(3-fluoro-4-methoxy-5-methylphenyl)-1-(2-(pyrimidin-5-yl)pyridin-4-yl)-1H-isoindol-3-amine;

4-Fluoro-1-(4-methoxy-3,5-dimethylphenyl)-1-(2-(pyrimidin-5-yl)pyridin-4-yl)-1H-isoindol-3-amine;

4-Fluoro-1-(5-methoxy-4,6-dimethylpyridin-2-yl)-1-(2-(pyrimidin-5-yl)pyridin-4-yl)-1H-isoindol-3-amine;

1-(2-Cyclopropylpyridin-4-yl)-4-fluoro-1-(3-(pyrazin-2-yl)phenyl)-1H-isoindol-3-amine trifluoroacetate;

4-Fluoro-1-(3-(4-methoxypyridin-2-yl)phenyl)-1-(2-methoxypyridin-4-yl)-1H-isoindol-3-amine;

2-(3-(3-Amino-4-fluoro-1-(2-methoxypyridin-4-yl)-1H-isoindol-1-yl)phenyl)isonicotinonitrile;

1-(2-(Difluoromethyl)pyridin-4-yl)-4-fluoro-1-(3-(pyrimidin-5-yl)phenyl)-1H-isoindol-3-amine;

(R) and (S) 1-(2-(Difluoromethyl)pyridin-4-yl)-4-fluoro-1-(3-(pyrimidin-5-yl)phenyl)-1H-isoindol-3-amine;

1-(2-(Difluoromethyl)pyridin-4-yl)-4-fluoro-1-(2-(pyrimidin-5-yl)pyridin-4-yl)-1H-isoindol-3-amine;

5-(3-Amino-4-fluoro-1-(3-(pyrimidin-5-yl)phenyl)-1H-isoindol-1-yl)-2-methoxybenzonitrile;

4-Fluoro-1-(5-methoxy-4,6-dimethylpyridin-2-yl)-1-(3-(pyrimidin-5-yl)phenyl)-1H-isoindol-3-amine;

1-(2,6-Dimethylpyrimidin-4-yl)-4-fluoro-1-(3-(pyrimidin-5-yl)phenyl)-1H-isoindol-3-amine;

1-(3,4-Difluoro-5-methoxyphenyl)-4-fluoro-1-(3-(pyrimidin-5-yl)phenyl)-1H-isoindol-3-amine;

2-(5-(3-Amino-4-fluoro-1-(3-(pyrimidin-5-yl)phenyl)-1H-isoindol-1-yl)-2-methoxy-3-methylphenyl)acetonitrile;

4-Fluoro-1-(4-fluoro-3-methoxyphenyl)-1-(3-(pyrimidin-5-yl)phenyl)-1H-isoindol-3-amine;

4-Fluoro-1-(6-methoxy-5-(trifluoromethyl)pyridin-3-yl)-1-(3-(pyrimidin-5-yl)phenyl)-1H-isoindol-3-amine;

4-(3-Amino-4-fluoro-1-(2-(trifluoromethyl)pyridin-4-yl)-1H-isoindol-1-yl)-2-(pyrazin-2-yl)phenol;

4-Fluoro-1-(4-methoxy-3-(pyrimidin-5-yl)phenyl)-1-(2-(trifluoromethyl)pyridin-4-yl)-1H-isoindol-3-amine;

1-(2-Cyclopropylpyridin-4-yl)-4-fluoro-1-(2-(pyrimidin-5-yl)pyridin-4-yl)-1H-isoindol-3-amine;

3-(5-Difluoromethoxy-4,6-dimethyl-pyridin-2-yl)-7-fluoro-3-(5'-fluoro-[2,3]bipyridinyl-4-yl)-3H-isoindol-1-ylamine;

5-(3-Amino-4-fluoro-1-(3-(pyrimidin-5-yl)phenyl)-1H-isoindol-1-yl)-2-methoxy-3-methylbenzonitrile;

6-Chloro-4-fluoro-1-(3-(pyrimidin-5-yl)phenyl)-1-(2-(trifluoromethyl)pyridin-4-yl)-1H-isoindol-3-amine; and 6-Chloro-4-fluoro-1-(2-methylpyridin-4-yl)-1-(3-(pyrimidin-5-yl)phenyl)-1H-isoindol-3-amine, as a free base or a pharmaceutically acceptable salt thereof.

In another aspect of the invention, there is provided a pharmaceutical composition comprising as active ingredient a therapeutically effective amount of a compound according formula (I) in association with pharmaceutically acceptable excipients, carriers or diluents.

In another aspect of the invention, there is provided a compound according to formula (I), or a pharmaceutically acceptable salt thereof, for use as a medicament.

In another aspect of the invention, there is provided use of a compound according to formula (I), as a medicament for treating or preventing an Aβ-related pathology.

In another aspect of the invention, there is provided use of a compound according to formula (I), as a medicament for treating or preventing an Aβ-related pathology, wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer Disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided use of a compound according to formula (I), as a medicament for treating or preventing Alzheimer Disease.

In another aspect of the invention, there is provided use of a compound according to formula (I), in the manufacture of a medicament for treating or preventing an Aβ-related pathology.

In another aspect of the invention, there is provided use of a compound according to formula (I), in the manufacture of a medicament for treating or preventing an Aβ-related pathology, wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided use of a compound according to formula (I), in the manufacture of a medicament for treating or preventing Alzheimer's Disease.

In another aspect of the invention, there is provided a method of inhibiting activity of BACE comprising contacting said BACE with a compound according to formula (I).

In another aspect of the invention, there is provided a method of treating or preventing an Aβ-related pathology in a mammal, comprising administering to said patient a therapeutically effective amount of a compound according to formula (I).

In another aspect of the invention, there is provided a method of treating or preventing an Aβ-related pathology in a mammal, comprising administering to said patient a therapeutically effective amount of a compound according to formula (I), wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided a method of treating or preventing Alzheimer's Disease, comprising administering to said patient a therapeutically effective amount of a compound according to formula (I).

In another aspect of the invention, there is provided a method of treating or preventing Alzheimer's Disease, comprising administering to said patient a therapeutically effective amount of a compound according to formula (I), wherein said mammal is a human.

In another aspect of the invention, there is provided a method of treating or preventing an Aβ-related pathology in a mammal, comprising administering to said patient a therapeutically effective amount of a compound according to formula (I), and at least one cognitive enhancing agent, memory enhancing agent, or choline esterase inhibitor.

In another aspect of the invention, there is provided a method of treating or preventing an Aβ-related pathology in a mammal, comprising administering to said patient a therapeutically effective amount of a compound according to formula (I), and at least one cognitive enhancing agent, memory enhancing agent, or choline esterase inhibitor, wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided a method of treating or preventing an Aβ-related pathology in a mammal, comprising administering to said patient a therapeutically effective amount of a compound according to formula (I), and at least one cognitive enhancing agent, memory enhancing agent, or choline esterase inhibitor, wherein said Aβ-related pathology is Alzheimer Disease.

In another aspect of the invention, there is provided a method of treating or preventing an Aβ-related pathology in a mammal, comprising administering to said patient a therapeutically effective amount of a compound according to formula (I), and at least one cognitive enhancing agent, memory enhancing agent, or choline esterase inhibitor, wherein said mammal is a human.

The present invention relates to the use of compounds of formula (I) as hereinbefore defined as well as to the salts thereof. Salts for use in pharmaceutical compositions will be pharmaceutically acceptable salts, but other salts maybe useful in the production of the compounds of formula (I)

Compounds of the invention can be used as medicaments. In some embodiments, the present invention provides compounds of formula (I), or pharmaceutically acceptable salts, tautomers or in vivo-hydrolysable precursors thereof, for use as medicaments. In some embodiments, the present invention provides compounds described here in for use as medicaments for treating or preventing an Aβ-related pathology. In some further embodiments, the Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In some embodiments, the present invention provides use of compounds of formula (I) or pharmaceutically acceptable salts, tautomers or in vivo-hydrolysable precursors thereof, in the manufacture of a medicament for the treatment or prophylaxis of Aβ-related pathologies. In some further embodiments, the Aβ-related pathologies include such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

In some embodiments, the present invention provides a method of inhibiting activity of BACE comprising contacting the BACE with a compound of the present invention. BACE is thought to represent the major β-secretase activity, and is considered to be the rate-limiting step in the production of amyloid-β-protein (Aβ). Thus, inhibiting BACE through inhibitors such as the compounds provided herein would be useful to inhibit the deposition of Aβ and portions thereof. Because the deposition of Aβ and portions thereof is linked to diseases such Alzheimer Disease, BACE is an important candidate for the development of drugs as a treatment and/or prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

In some embodiments, the present invention provides a method for the treatment of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration, comprising administering to a mammal (including human) a therapeutically effective amount of a compound of formula (I), or a pharmaceutically acceptable salt, tautomer or in vivo-hydrolysable precursor thereof.

In some embodiments, the present invention provides a method for the prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration comprising administering to a mammal (including human) a therapeutically effective amount of a compound of formula (I) or a pharmaceutically acceptable salt, tautomer or in vivo-hydrolysable precursors.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration by administering to a mammal (including human) a compound of formula (I) or a pharmaceutically acceptable salt, tautomer or in vivo-hydrolysable precursors and a cognitive and/or memory enhancing agent.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration by administering to a mammal (including human) a compound of formula (I) or a pharmaceutically acceptable salt, tautomer or in vivo-hydrolysable precursors thereof wherein constituent members are provided herein, and a choline esterase inhibitor or anti-inflammatory agent.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration, or any other disease, disorder, or condition described herein, by administering to a mammal (including human) a compound of the present invention and an atypical antipsychotic agent. Atypical antipsychotic agents includes, but not limited to, Olanzapine (marketed as Zyprexa), Aripiprazole (marketed as Abilify), Risperidone (marketed as Risperdal), Quetiapine (marketed as Seroquel), Clozapine (marketed as Clozaril), Ziprasidone (marketed as Geodon) and Olanzapine/Fluoxetine (marketed as Symbyax).

In some embodiments, the mammal or human being treated with a compound of the invention has been diagnosed with a particular disease or disorder, such as those described herein. In these cases, the mammal or human being treated is in need of such treatment. Diagnosis, however, need not be previously performed.

The present invention also includes pharmaceutical compositions, which contain, as the active ingredient, one or more of the compounds of the invention herein together with at least one pharmaceutically acceptable carrier, diluent or excipient.

The definitions set forth in this application are intended to clarify terms used throughout this application. The term "herein" means the entire application.

All compounds in the present invention may exist in particular geometric or stereo isomeric forms. The present invention takes into account all such compounds, including cis- and trans isomers, R- and S-enantiomers, diastereomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used in this application, the term "optionally substituted," means that substitution is optional and therefore it is possible for the designated atom or moiety to be unsubstituted.

As used herein, "alkyl", used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{0-6}$ alkyl" denotes alkyl having 0, 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. In the case where a subscript is the integer 0 (zero) the group to which the subscript refers to indicates that the group is may be absent, i.e. there is a direct bond between the groups.

As used herein, "alkenyl" used alone or as a suffix or prefix is intended to include both branched and straight-chain alkene or olefin containing aliphatic hydrocarbon groups having from 2 to 12 carbon atoms or if a specified number of carbon atoms is provided then that specific number would be intended. For example "$C_{2-6}$alkenyl" denotes alkenyl having 2, 3, 4, 5 or 6 carbon atoms. Examples of alkenyl include, but are not limited to, vinyl, allyl, 1-propenyl, 1-butenyl, 2-butenyl, 3-butenyl, 2-methylbut-2-enyl, 3-methylbut-1-enyl, 1-pentenyl, 3-pentenyl and 4-hexenyl.

As used herein, "alkynyl" used also or as a suffix or prefix is intended to include to include both branched and straight-chain alkynyl or olefin containing aliphatic hydrocarbon groups having from 2 to 12 carbon atoms or if a specified number of carbon atoms is provided then that specific number would be intended. Examples include, but are not limited to, ethynyl, 1-propynyl, 2-propynyl, 3-butynyl, pentynyl, hexynyl and 1-methylpent-2-ynyl.

As used herein, "aromatic" refers to hydrocarbonyl groups having one or more unsaturated carbon ring(s) having aromatic characters, (e.g. 4n+2 delocalized electrons) and comprising up to 14 carbon atoms. In addition "heteroaromatic" refers to groups having one or more unsaturated rings containing carbon and one or more heteroatoms such as nitrogen, oxygen or sulphur having aromatic character (e.g. 4n+2 delocalized electrons).

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. Examples of polycyclic rings include, but are not limited to, 2,3-dihydro-1,4-benzodioxine and 2,3-dihydro-1-benzofuran.

As used herein, the terms "cycloalkyl" or "carbocyclyl" are intended to include saturated ring groups, having the specified number of carbon atoms. These may include fused or bridged polycyclic systems. Preferred cycloalkyls have from 3 to 10 carbon atoms in their ring structure, and more preferably have 3, 4, 5, and 6 carbons in the ring structure. For example, "$C_{3-6}$ cycloalkyl" denotes such groups as cyclopropyl, cyclobutyl, cyclopentyl, or cyclohexyl.

As used herein, the term "cycloalkenyl" is intended to include unsaturated ring groups, having the specified number of carbon atoms. These may include fused or bridged polycyclic systems. Preferred cycloalkenyls have from 3 to 10 carbon atoms in their ring structure, and more preferably have 3, 4, 5, and 6 carbons in the ring structure. For example, "$C_{3-6}$ cycloalkenyl" denotes such groups as cyclopropenyl, cyclobutenyl, cyclopentenyl, or cyclohexenyl.

As used herein, "halo" or "halogen" refers to fluoro, chloro, bromo, and iodo. "Counterion" is used to represent a small, negatively or positively charged species such as chloride, bromide, hydroxide, acetate, sulfate, tosylate, benezensulfonate, ammonium, lithium ion and sodium ion and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —$CH_2$— group is optionally replaced by a —C(O)—; and where unless stated to the contrary a ring nitrogen or sulphur atom is optionally oxidised to form the N-oxide or S-oxide(s) or a ring nitrogen is optionally quarternized; wherein a ring —NH is optionally substituted with acetyl, formyl, methyl or mesyl; and a ring is optionally substituted with one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-aromatic heterocycle. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl and 2,5-dioxoimidazolidinyl.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, benzoxazolyl, aza-benzoxazolyl indolinyl, imidazothiazolyl and the like. In some embodiments, the heteroaryl group has from 1 to 20 carbon atoms, and in further embodiments from 3 to 20 carbon atoms. In some embodiments, the heteroaryl group contains 3 to 14, 4 to 14, 3 to 7, or 5 to 6 ring-forming atoms. In some embodiments, the heteroaryl group has 1 to 4, 1 to 3, or 1 to 2 heteroatoms. In some embodiments, the heteroaryl group has 1 heteroatom.

As used herein, "haloalkyl", used alone or as a suffix or prefix, is intended to include both branched and straight chain saturated aliphatic hydrocarbon groups, having at least one halogen substituent and having from 1 to 12 carbon atoms or if a specified number of carbon atoms is provided then that specific number would be intended. For example "$C_{0-6}$haloalkyl" denotes alkyl having 0, 1, 2, 3, 4, 5 or 6 carbon atoms. Examples of haloalkyl include, but are not limited to, fluoromethyl, difluoromethyl, trifluoromethyl, chlorofluoromethyl, 1-fluoroethyl, 3-fluoropropyl, 2-chloropropyl, 3,4-difluorobutyl.

As used herein, the phrase "protecting group" means temporary substituents which protect a potentially reactive functional group from undesired chemical transformations. Examples of such protecting groups include esters of carboxylic acids, say' ethers of alcohols, and acetals and ketals of aldehydes and ketones respectively. The field of protecting group chemistry has been reviewed (Greene, T. W.; Wuts, P. G. M. *Protective Groups in Organic Synthesis*, 3$^{rd}$ ed.; Wiley: New York, 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by chemical methods. Generally, such salts can be prepared by reacting the free acid or base forms of these compounds with a stoichiometric amount of the appropriate base or acid in water or in an organic solvent, or in a mixture of the two; generally, nonaqueous media like diethyl ether, ethyl acetate, ethanol, isopropanol, or acetonitrile are used.

As used herein, "tautomer" means other structural isomers that exist in equilibrium resulting from the migration of a hydrogen atom. For example, keto-enol tautomerism where the resulting compound has the properties of both a ketone and an unsaturated alcohol.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labelled compounds of the invention. An "isotopically" or "radio-labelled" compound is a compound of the invention where one or more atoms are replaced or substituted with an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labelled compounds will depend on the specific application of that radio-labelled compound. For example, for in vitro receptor labelling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labelled compound" is a compound that has incorporated at least one radionuclide. In some embodiments the radionuclide is selected from the group consisting of $^3H$, $^{14}C$, $^{125}I$, $^{35}S$ and $^{82}Br$.

For the avoidance of doubt the present invention relates to any one of compounds falling within the scope of formula (I) as defined above.

It will be appreciated that throughout the specification, the number and nature of substituents on rings in the compounds of the invention will be selected so as to avoid sterically undesirable combinations.

The anti-dementia treatment defined herein maybe applied as a sole therapy or may involve, in addition to the compound of the invention, conventional chemotherapy. Such chemotherapy may include one or more of the following categories of agents: acetyl cholinesterase inhibitors, anti-inflammatory agents, cognitive and/or memory enhancing agents or atypical antipsychotic agents.

Such conjoint treatment maybe achieved by way of the simultaneous, sequential or separate dosing of the individual components of the treatment. Such combination products employ the compounds of this invention.

Additional conventional chemotherapy may include one or more of the following categories of agents:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof (ii) atypical antipsychotics including for example quetiapine and pharmaceutically active isomer(s) and metabolite(s) thereof (iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof (iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof (v) anticonvulsants including for example carbamazepine, valproate, lamotrigine, gabapentin and equivalents and pharmaceutically active isomer(s) and metabolite(s) thereof (vi) Alzheimer's therapies including for example donepezil, memantine, tacrine and equivalents and pharmaceutically active isomer(s) and metabolite(s) thereof (vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof (viii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof (ix) stroke therapies including for example abciximab, activase, NXY-059, citicoline, crobenetine, desmoteplase, repinotan, traxoprodil and equivalents and pharmaceutically active isomer(s) and metabolite(s) thereof (x) urinary incontinence therapies including for example darafenacin, falvoxate, oxybutynin, propiverine, robalzotan, solifenacin, tolterodine and equivalents and pharmaceutically active isomer(s) and metabolite(s) thereof (xi) neuropathic pain therapies including for example gabapentin, lidoderm, pregablin and equivalents and pharmaceutically active isomer(s) and metabolite(s) thereof (xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof (xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof (xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof Such combination products employ the compounds of this invention within the dosage range described herein and the other pharmaceutically active compound or compounds within approved dosage ranges and/or the dosage described in the publication reference.

Compounds of the present invention maybe administered orally, parenteral, buccal, iii vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and is weight of the patient and other factors normally considered by the attending physician, when determining the individual regimen and dosage level as the most appropriate for a particular patient.

An effective amount of a compound of the present invention for use in therapy of dementia is an amount sufficient to symptomatically relieve in a warm-blooded animal, particularly a human the symptoms of dementia, to slow the progression of dementia, or to reduce in patients with symptoms of dementia the risk of getting worse.

In addition to the compounds of the present invention, the pharmaceutical composition of this invention may also contain, or be co-administered (simultaneously or sequentially) with, one or more pharmacological agents of value in treating one or more disease conditions referred to herein.

Salts of the compounds of the invention are preferably physiologically well tolerated and non toxic. Many examples of salts are known to those skilled in the art. All such salts are within the scope of this invention, and references to compounds include the salt forms of the compounds.

Where the compounds contain an amine function, these may form quaternary ammonium salts, for example by reaction with an alkylating agent according to methods well known to the skilled person. Such quaternary ammonium compounds are within the scope of the invention.

Compounds containing an amine function may also form N-oxides. A reference herein to a compound that contains an amine function also includes the N-oxide.

Where a compound contains several amine functions, one or more than one nitrogen atom maybe oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent is such as hydrogen peroxide or a per-acid (e.g. a peroxycarboxylic acid), see for example *Advanced Organic Chemistry*, by Jerry March, $4^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Where the compounds contain chiral centres, all individual optical forms such as enantiomers, epimers and diastereoisomers, as well as racemic mixtures of the compounds are within the scope of the invention.

The quantity of the compound to be administered will vary for the patient being treated and will vary from about 100 ng/kg of body weight to 100 mg/kg of body weight per day and preferably will be from 10 pg/kg to 10 mg/kg per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In another aspect of the invention, there is provided that the compounds of the invention, or a pharmaceutically acceptable salt thereof, can be used as medicaments, e.g. to treat or prevent Aβ-related pathologies.

In another aspect of the invention, there is provided that the compounds of the invention, or a pharmaceutically acceptable salt thereof, can be used for the manufacture of a medicament to treat or prevent Aβ-related pathologies.

In another aspect of the invention, there is provided a method for the treatment of Aβ-related pathologies, comprising administering a therapeutically effective amount of a compound of Formula (I), or a pharmaceutically acceptable salt thereof, to a subject, such as a mammal or a human being, in need thereof.

The compounds of the invention and their pharmaceutically acceptable salts thereby is provides methods of treatment of Aβ-related pathologies, such as, but not limited to, Alzheimer's disease, Downs syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, presenile dementia, senile dementia, dementia associated with Parkinson's disease, progressive supranuclear palsy, traumatic brain injury and cortical basal degeneration.

In another aspect of the invention, there is provided a pharmaceutical composition comprising as active ingredient a therapeutically effective amount of a compound according formula I in association with pharmaceutically acceptable excipients, carriers or diluents.

In another aspect of the invention, there is provided a method of treating or preventing an Aβ-related pathology in a mammal, such as human being, comprising administering to said patient a therapeutically effective amount of a compound according to formula I, and at least one cognitive enhancing agent, memory enhancing agent, or choline esterase inhibitor, wherein said Aβ-related pathology is Alzheimer Disease.

The treatment of Aβ-related pathology defined herein may be applied as a mono therapy or may involve, in addition to the compound of the invention, conjoint treatment with therapy of value in treating one or more disease conditions referred to herein. Such therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (Aricept), galantamine (Reminyl or Razadyne), rivastigmine (Exelon), tacrine (Cognex) and memantine (Namenda, Axura or Ebixa). Atypical antipsychotic agents includes, but not limited to, olanzapine (marketed as Zyprexa), aripiprazole (marketed as Abilify), risperidone (marketed as Risperdal), quetiapine (marketed as Seroquel), clozapine (marketed as Clozaril), ziprasidone (marketed as Geodon) and olanzapine/fluoxetine (marketed as Symbyax).

Such conjoint treatment may be achieved by way of the simultaneous, sequential or separate dosing of the individual components of the treatment. Such combination products employ the compounds of the invention.

Additional conventional therapy may include one or more of the following categories of agents:
(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, rameltcon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof
(ii) atypical antipsychotics including for example quetiapine and pharmaceutically active isomer(s) and metabolite(s) thereof
(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof
(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof
(v) anticonvulsants including for example carbamazepine, valproate, lamotrogine, gabapentin and equivalents and pharmaceutically active isomer(s) and metabolite(s) thereof
(vi) Alzheimer's therapies including for example donepezil, memantine, tacrine and equivalents and pharmaceutically active isomer(s) and metabolite(s) thereof
(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof
(viii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof
(ix) stroke therapies including for example abciximab, activase, NXY-059, citicoline, crobenetine, desmoteplase, repinotan, traxoprodil and equivalents and pharmaceutically active isomer(s) and metabolite(s) thereof
(x) urinary incontinence therapies including for example darafenacin, falvoxate, oxybutynin, propiverine, robalzotan, solifenacin, tolterodine and equivalents and pharmaceutically active isomer(s) and metabolite(s) thereof
(xi) neuropathic pain therapies including for example gabapentin, lidoderm, pregablin and is equivalents and pharmaceutically active isomer(s) and metabolite(s) thereof
(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof
(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof
(xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this invention within the dosage range described herein and the other pharmaceutically active compound or compounds within approved dosage ranges and/or the dosage described in the publication reference.

Methods of Preparation

The present invention also relates to processes for preparing the compound of formula (I) as a free base or a pharmaceutically acceptable salt thereof. Throughout the following description of such processes it is to be understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in

*Protective Groups in Organic Synthesis* by T. W. Greene, P. G. M Wutz, 3rd Edition, Wiley-Interscience, New York, 1999. It is to be understood that microwaves can alternatively be used for the heating of reaction mixtures.

Another aspect of the present invention provides a process for preparing a compound of formula (I), or a pharmaceutically acceptable salt thereof, wherein $R^{13}$ and $R^{14}$ are defined as for A or B in formula (I) above, $R^C$ is defined as for C in formula (I) above and $R^1$ is, unless specified otherwise, as defined in formula (I). Said process comprises of:

(i) Formation of a Corresponding Compound of Formula (V):

A compound of formula (V) may be obtained as depicted in Scheme 1, for example by metallation or halogen metal exchange of a compound of formula (II), wherein G is either a hydrogen or a halogen respectively, to obtain an intermediate of formula (III), wherein L is a ligand such as halogen and n is between 0 and 6. The intermediate (III) is not isolated but reacted further with a compound of formula (IV), wherein LG is either $N(CH_3)(OCH_3)$ or halogen or another suitable leaving group as described by R. K. Dieter, (*Tetrahedron*, 55 (1999) 4177-4236).

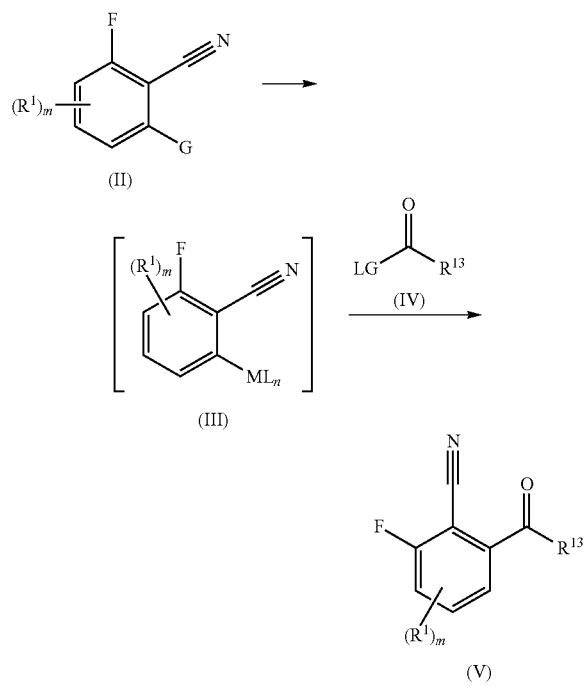

The reaction may be carried out by treating a compound of formula (II), wherein G is a halogen (such as iodine or bromine) with an appropriate metallating reagent, such as a lithium reagent (such as tert-butyllithium, n-butyllithium, lithium diispropylamide or lithium tetramethyl piperidine) or with a Grignard reagent (such as isopropylmagnesium bromide) or with a metal (such as magnesium, zinc or manganese), by standard methods known in the art. Optionally, the formed intermediate of formula (III) may be further transmetallated by treatment with a metal salt or metal complex, such as copper cyanide di(lithium bromide), to obtain a new intermediate of formula (III), and then treat said intermediate of formula (III) with a compound of formula (IV), wherein LG represents a leaving group such as a halogen (such as chlorine) or $N(CH_3)(OCH_3)$. Optionally, this transformation may be performed under the influence of a transition metal catalyst, such as a palladium salt or complex as described in the literature by R. K. Dieter, (*Tetrahedron*, 55 (1999) 4177-4236). The reaction may be performed in a suitable solvent, such as diethyl ether or tetrahydrofuran at a temperature between −105° C. and room temperature.

(ii) Formation of a Corresponding Compound of Formula (VIII):

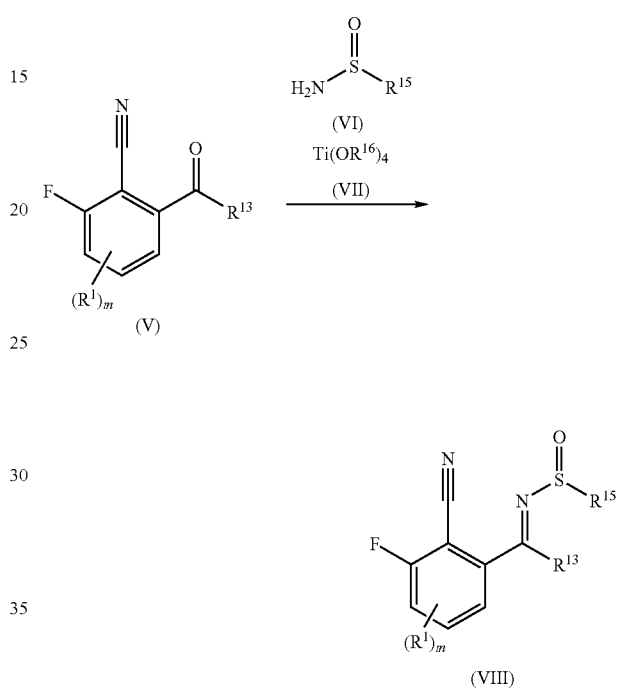

A compound of formula (VIII) may be obtained by reacting a compound of formula (V) with a compound of formula (VI) (Scheme 2), wherein $R^{15}$ is alkyl (such as for example ten-butyl). The reaction is performed in the presence of a suitable Lewis acid of formula (VII), wherein $R^{16}$ is alkyl (such as ethyl or isopropyl). The reaction is performed in a suitable solvent (such as diethyl ether or tetrahydrofuran) at a temperature between room temperature and reflux temperature. Compound (VI) might be used as the pure enantiomer to obtain an enantiomerically pure compound (VII).

(iii) Formation of a Corresponding Compound of Formula (X)

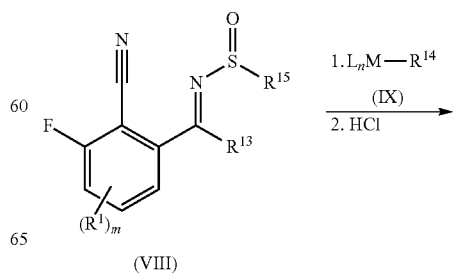

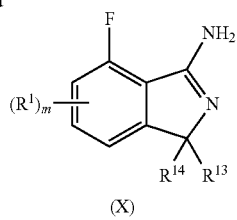

(X)

A compound of formula (X) may be prepared as shown in Scheme 3 by treating a compound of formula (VIII), with an appropriate organo metallic reagent of formula (IX) wherein M is a metal (such as lithium zinc or magnesium), L is a ligand (such as halogen) and n is between 0 and 2, and $R^{14}$ is as defined above, followed by treatment with a suitable acid, such as hydrochloric acid. The reaction may be performed in a suitable solvent, such as diethyl ether or tetrahydrofuran, at a temperature between −105° C. and room temperature. The organo metallic reagent of formula (IX) may be generated from the corresponding LG-$R^{14}$, wherein LG represents a leaving group such as a halogen, such as iodide, bromide or chloride by known methods as described in *Advanced Organic Chemistry* by Jerry March 4$^{th}$ edition, Wiley Interscience. If enantiomerically pure or enriched compound (VIII) is used in this reaction, an enantiomerically pure or enantiomerically enriched compound (X) might be obtained.

(iv) Formation of a Corresponding Compound of Formula (I):

A compound of formula (I) may be obtained (Scheme 4) by starting from, for example, a compound of formula (Xa), wherein LG represents a leaving group such as halogen (such as chlorine, bromine or iodine) or an alkyl-, aryl- or haloalkyl-sulfonate (such as triflate), and reacting said compound (Xa) with a compound of formula (XI), wherein $R^C$ is defined as above and T represents a boronic acid or a boronic ester or a stannane, under the influence of a transition metal catalyst as described in for example *Metal Catalyzed Cross-coupling Reactions* by F. Diederich and P. J. Stang, Wiley VCH, Weinheim, 1998. The compound of formula (XI) may be generated from the corresponding LG-$R^C$, wherein LG represents a leaving group, such as a halogen, (such as iodide, bromide or chlorine) by known methods as described in for example *Advanced Organic Chemistry* by Jerry March 4$^{th}$ edition, Wiley Interscience, Scheme 4

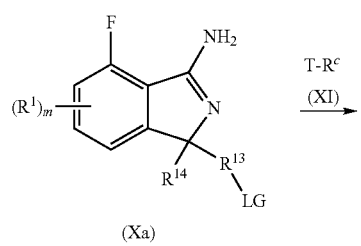

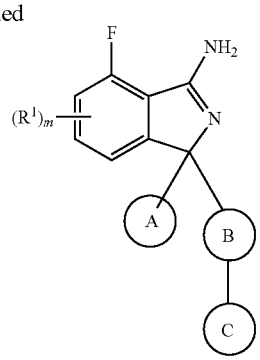

(I)

The reaction may be carried out by coupling of a compound of formula (Xa), with an appropriate aryl or heteroaryl boronic acid or boronic ester or stannane of formula T-$R^C$. The reaction may also be carried out using a suitable metal catalyst such as a palladium catalyst, such as [1,1'-bis(diphenylphosphino)ferrocene]palladium(II) chloride, tetrakis(triphenylphosphine)-palladium(0), palladium diphenylphosphineferrocene dichloride, palladium(II) acetate or bis(dibenzylideneacetone) palladium (0). Optionally, a suitable ligand such as triphenylphosphine, tri-tert-butylphosphine or 2-(dicyclohexylphosphino)biphenyl. A suitable base, such as cesium fluoride, an alkyl amine, such as triethyl amine, or an alkali metal or alkaline earth metal carbonate or hydroxide such as potassium carbonate, sodium carbonate, cesium carbonate, or sodium hydroxide, may be used in the reaction. Said reaction may be performed at a temperature range between +20° C. and +160° C., in a suitable solvent, such as toluene, tetrahydrofuran, dioxane, dimethoxyethane, water, ethanol, N,N-dimethylacetamide or N,N-dimethylformamide, or mixtures thereof. If enantiomerically pure or enriched compound (Xa) is used in this reaction, an enantiomerically pure or enantiomerically enriched compound (I) might be obtained.

Compounds of formula (II), (IV), (VI), (VII), (IX) and (XI) are commercially available compounds, or they are known in the literature, or they are prepared by standard processes known in the art.

General Methods

All solvents used were of analytical grade and commercially available anhydrous solvents were routinely used for reactions.

Starting materials used were available from commercial sources, or prepared according to literature procedures.

Microwave heating was performed in a Creator, Initiator or Smith Synthesizer Single-mode microwave cavity producing continuous irradiation at 2450 MHz.

$^1$H NMR spectra were recorded in the indicated deuterated solvent at 400 MHz and the spectra were obtained unless stated otherwise, using a Bruker av400 NMR spectrometer equipped with a 3 mm flow injection SEI $^1$H/D-$^{13}$C probe head with Z-gradients, using a BEST 215 liquid handler for sample injection, or using a Bruker DPX400 NMR spectrometer equipped with a 4-nucleus probehead with Z-gradients. 500 MHz spectra were recorded using a Bruker 500 MHz Avance III NMR spectrometer, operating at 500 MHz for $^1$H, 125 MHz for $^{13}$C, and 50 MHz for $^{15}$N equipped with a 5 mm TXI probehead with Z-gradients. 600 MHz spectra were recorded using aBruker DRX 600 NMR spectrometer, operating at 600 MHz for $^1$H, 150 MHz for $^{13}$C, and 60 MHz for $^{15}$N equipped with a 5 mm TXI probehead with Z-gradients.

Chemical shifts are given in ppm down- and upheld from TMS. Resonance multiplicities are denoted s, d, t, q, m and br for singlet, doublet, triplet, quartet, multiplet, and broad respectively. In cases where the NMR spectra are complex; only diagnostic signals are reported. LC-MS analyses were recorded on a Waters LCMS equipped with a Waters X-Terra MS, C8-column, (3.5 µm, 100 mm×3.0 mm i.d.). The mobile phase system consisted of A: 10 mM ammonium acetate in water/acetonitrile (95:5) and B: acetonitrile. A linear gradient was applied running from 0% to 100% B in 4-5 minutes with a flow rate of 1.0 mL/min. The mass spectrometer was equipped with an electrospray ion source (ESI) operated in a positive or negative ion mode. The capillary voltage was 3 kV and the mass spectrometer was typically scanned between m/z 100-700. Alternative, LC-MS HPLC conditions were as follows: Column: Agilent Zorbax SB-C8 2 mm ID×50 mm Flow: 1.4 mL/minGradient: 95% A to 90% B over 3 min. hold 1 minute ramp down to 95% A over 1 minute and hold 1 minute. Where A=2% acetonitrile in water with 0.1% formic acid and B=2% water in acetonitrile with 0.1% formic acid. UV-DAD 210-400 nm. Or LC-MS analyses were performed on a LC-MS consisting of a Waters sample manager 2777C, a Waters 1525µ binary pump, a Waters 1500 column oven, a Waters ZQ single quadrupole mass spectrometer, a Waters PDA2996 diode array detector and a Sedex 85 ELS detector. The mass spectrometer was configured with an atmospheric pressure chemical ionisation (APCI) ion source which was further equipped with atmospheric pressure photo ionisation (APPI) device. The mass spectrometer scanned in the positive mode, switching between APCI and APPI mode. The mass range was set to m/z 120-800 using a scan time of 0.3 s. The APPI repeller and the APCI corona were set to 0.86 kV and 0.80 µA, respectively. In addition, the desolvation temperature (300° C.), desolvation gas (400 L/Hr) and cone gas (5 L/Hr) were constant for both APCI and APPI mode. Separation was performed using a Gemini column C18, 3.0 mm×50 mm, 3 µm, (Phenomenex) and run at a flow rate of 1 ml/min. A linear gradient was used starting at 100% A (A: 10 mM ammonium acetate in 5% methanol) and ending at 100% B (methanol). The column oven temperature was set to 40° C.

Mass spectra (MS) were run using an automated system with atmospheric pressure chemical (APCI or CI) or electrospray (+ESI) ionization. Generally, only spectra where parent masses are observed are reported. The lowest mass major ion is reported for molecules where isotope splitting results in multiple mass spectral peaks (for example when chlorine is present). UPLCMS analyses were performed on an Waters Acquity UPLC system consisting of a Acquity Autosampler, Acquity Sample Organizer, Acquity Column Manager, Acquity Binary Solvent Manager, Acquity UPLC PDA detector and a Waters SQ Detector.

The mass spectrometer was equipped with an electrospray ion source (ES) operated in positive and negative ion mode. The capillary voltage was set to 3.0 kV and the cone voltage to 30 V, respectively. The mass spectrometer was scanned between m/z 100-600 with a scan time of 0.105s. The diode array detector scanned from 200-400 nm. The temperature of the Column Manager was set to 60° C. Separation was performed on a Acquity column, UPLC BEH, C18 1.7 µM run at a flow rate of 0.5 ml/min. A linear gradient was applied starting at 100% A (A: 10 mM NH$_4$OAc in 5% CH$_3$CN) ending at 100% B (B: CH$_3$CN) after 1.3 min then 100% B for 0.6 min.

Acquity column, UPLC BEH, C18 1.7 µM. Linear gradient, flow 0.5 ml/min. 0-100% B (MeCN) in 1.3 min, then 100% B for 0.6 min. ESpos/ESneg, m/z 100-600. A (A: 10 mM NH$_4$OAc in 5% CH$_3$CN)

Acquity column, UPLC BEH, C18 1.7 µM. Linear gradient, flow 0.5 ml/min, 0-100% B (MeCN) in 2.5 min, then 100% B until 3.8 min. ES+/ES−, m/z 100-600. A (A: 10 mM NH$_4$OAc in 5% CH$_3$CN)

GC-MS analyses were performed on a Agilent 6890N GC equipped with a Chrompack CP-Sil 5CB column (25 m×0.25 mm i.d. df=0.25)), coupled to an Agilent 5973 Mass Selective Detector operating in a chemical ionization (CI) mode and the MS was scanned between m/z 50-500.

Accurate mass analyses were performed on a QTOF micro (Waters). The mass spectrometer was equipped with an electrospray ion source that uses two probes, a sample probe and a lock mass probe, respectively. The lock mass solution was Leucine Enkephaline (0.5 ng/µL in MilliQ water) infused at flow rate of 0.1 mL/min. The reference scan frequency was set to 5.5 s. Before the analysis, the mass spectrometer was calibrated in the positive mode between 90-1000 Da using a solution of NaFormate. The mass spectrometer scanned in the centroid mode between m/z 100-1000 with a scan time of 1.0 s. The capillary voltage was set to 3.3 kV and the ES cone voltage was set to 28 V. The source temperature and desolvation temperature were set to 110° C. and 350° C., respectively. The collision energy was set to 6.0 V. The QTOF micro was equipped with an LC (HP1100 Agilent, Degasser, Binary pump, ALS and a column compartment). The column used was a Gemini C18, 3.0×50 mm, 3 u run at a flowrate of 1.0 mL/min. A linear gradient was applied starting at 100% A (A: 10 mM ammonium acetate) and ending at 100% B (B: acetonitrile) after 4 min. The column oven temperature was set to 40° C. The flow was split 1:4 prior to the ion source. 3 µL of the sample was injected on the column.

HPLC assays were performed using an Agilent HP1100 Series system equipped with a Waters X-Terra MS, C$_8$ column (3.0×100 mm, 3.5 µm). The column temperature was set to 40° C. and the flow rate to 1.0 mL/min. The Diode Array Detector was scanned from 200-300 nm. A linear gradient was applied, run from 0% to 100% B in 4 min. Mobile phase A: 10 mM ammonium acetate in water/acetonitrile (95:5), mobile phase B: acetonitrile.

Preparative HPLC was performed on a Waters Auto purification HPLC-UV system with a diode array detector using a Waters XTerra MS, C$_8$ column (19×300 mm, 7 µm) and a linear gradient of mobile phase B was applied. Mobile phase A: 0.1 M ammonium acetate in water/acetonitrile (95:5) and mobile phase B: acetonitrile. Flow rate: 20 mL/min. Thin layer chromatography (TLC) was performed on Merck TLC-plates (Silica gel 60 F$_{254}$) and spots were UV visualized. Flash chromatography was performed using Merck Silica gel 60 (0.040-0.063 mm), or employing a Combi Flash® Companion™ system using RediSep™ normal-phase flash columns.

Phase separation was optionally performed on an Isolute® phase separator

Room temperature refers to 20-25° C.

Solvent mixture compositions are given as volume percentages or volume ratios.

Terms and Abbreviations
atm: atmospheric pressure;
Boc: t-butoxycarbonyl;
Cbz: benzyloxycarbonyl;
DCM: dichloromethane;
DIPEA: diisopropylethylamine;
DMF: N;N-dimethyl formamide;
DMSO: dimethyl sulfoxide;
Et$_2$O: diethyl ether;
EtoAc: ethyl acetate;
h: hour(s);

HPLC: high pressure liquid chromatography;
min: minute(s);
MeOH: methanol;
NMR: nuclear magnetic resonance;
psi: pounds per square inch;
TFA: trifluoroacetic acid;
THF: tetrahydrofuran;
ACN: acetonitrile.
r.t. room temperature
sat saturated
aq aqueous Compounds have been named using CambridgeSoft MedChem ELN v2.1 or ACD/Name, version 9.0, software from Advanced Chemistry Development, Inc. (ACD/Labs), Toronto ON, Canada, www.acdlabs.com, 2004.

EXAMPLES

Below follows a number of non-limiting examples of compounds of the invention.

Example 1i

5-Bromo-2-fluoro-benzoyl chloride

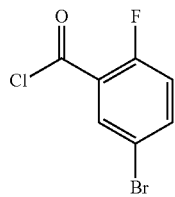

To a suspension of 5-bromo-2-fluoro-benzoic acid (10.0 g, 45.7 mmol) in anhydrous dichloromethane (200 mL) was added oxalyl chloride (5.2 mL, 59.4 mmol) followed by addition of anhydrous DMF (0.2 mL). The reaction mixture was stirred at room temperature overnight, then concentrated to dryness in vacuo to give title compound in quantitative yield, which was used directly in the next step.

$^1$H NMR (400 MHz, CDCl$_3$) δ ppm 8.22 (dd, 1 H), 7.77-7.73 (m, 1 H), 714 (dd, 1 H); $^{19}$F NMR (400 MHz, CDCl$_3$) δ ppm-110.55

Example 2i

2-Methoxy-isonicotinoyl chloride

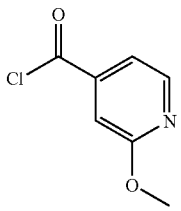

Thionyl chloride (30.0 mL, 0.39 mol) was added to a suspension of 2-methoxy-isonicotinic acid (15.0 g, 97.9 mmol) in anhydrous toluene (150 mL). The mixture was heated at 80° C. under nitrogen for 3 hours, cooled to room temperature and filtered. The filtrate was concentrated in vacuo to afford the title compound 7.7 g (46% yield).

$^1$H NMR (400 MHz, CDCl$_3$) δ ppm 8.36 (d, 1 H), 5.30 (d, 1 H), 7.38 (s, 1 H), 4.00 (s, 3 H).

Example 3i 2-(3-Bromobenzoyl)-6-fluorobenzonitrile

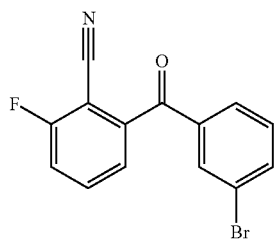

A solution of copper(I) cyanide (4.70 g, 52.50 mmol) and lithium bromide (2.63 mL, 105.00 mmol) in THF (65 mL) was added to (2-cyano-3-fluorophenyl)zinc(II) iodide (100 mL, 50 mmol) at −78° C. under an argon atmosphere. The mixture was stirred at r.t. for 1 h and then cooled to −78° C. 3-Bromobenzoyl chloride (6.94 mL, 52.50 mmol) was added dropwise and the mixture was stirred at r.t. for 4 h. NH$_4$Cl (50 mL, sat aq) was added followed by water (50 mL). The THF was removed in vacuo and the aqueous residue was diluted with water (100 mL) and DCM (150 mL). A precipitate was filtered off and the filtrate was added to a separation funnel. The organic layer was separated and the water phase extracted with DCM (100 mL). The combined organics were washed with brine (150 mL), dried over MgSO$_4$, concentrated and purified on a silica gel column eluted with DCM to give the title compound (13.37 g, 88% yield): MS (ES+) m/z 304, 306 [M+H]$^+$.

Example 4i 2-(3-Bromo-4-fluoro-benzoyl)-6-fluoro-benzonitrile

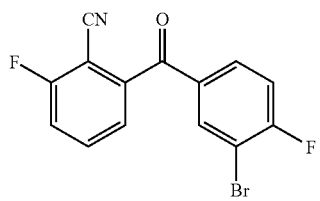

To a solution of 2-cyano-3-fluorophenylzinc (80.0 mL, 40.0 mmol, 0.5 M in THF), tetrakistriphenylphosphine palladium(0) (2.3 g, 2.0 mmol) was added in small portions at 0° C. A solution of 3-bromo-4-fluorobenzoyl chloride (10.0 g, 42.1 mmol) in anhydrous THF (20 mL) was then added dropwise and the reaction mixture was stirred at 0° C. for 1 hour. The reaction was quenched by addition of water (150 mL) and the resulting mixture was extracted with ethyl acetate (2×150 mL). The combined organic extracts were washed with brine, dried over sodium sulfate and concentrated in vacuo. The crude product was purified by flash column chromatography using 30% ethyl acetate in hexanes to afford the title compound (7.90 g, 61% yield).

$^{1}$H NMR (400 MHz, CDCl$_{3}$) δ ppm 8.07 (dd, 1 H), 7.79-7.71 (m, 2 H), 7.48-7.42 (m, 2 H), 7.26 (m, 1 H); $^{19}$F NMR (400 MHz, CDCl$_{3}$) δ ppm-97.16, -103.63.

Example 5i 2-(5-Bromo-2-fluoro-benzoyl)-6-fluoro-benzonitrile

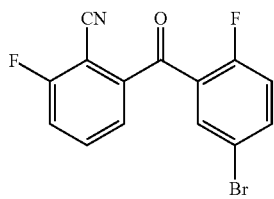

The title compound was synthesized as described for Example 41 in 61% yield starting from 5-bromo-2-fluoro-benzoyl chloride (11.0 g, 45.7 mmol).

$^{1}$H NMR (400 MHz, CDCl$_{3}$) δ ppm 7.87 (dd, 1 H), 7.74-7.70 (m, 2 H), 7.49-7.44 (m, 2 H), 7.07 (t, 1 H). $^{19}$F NMR (400 MHz, CDCl$_{3}$) δ ppm-104.24, -111.43.

Example 6i

2-Fluoro-6-(2-methoxy-pyridine-4-carbonyl)-benzonitrile

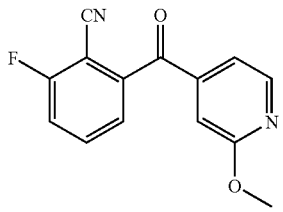

The title compound was synthesized as described for Example 41 in 73% yield starting from 3-fluoro-2-cyanozinc iodide (0.5M in THF, 88.0 mL, 44.0 mmol) and 2-methoxy-isonicotinoyl chloride (7.7 g, 44.9 mmol).

$^{1}$H NMR (400 MHz, CDCl$_{3}$) δ ppm 8.39 (d, 1 H), 7.75-7.71 (m, 1 H), 7.50-7.46 (m, 2 H), 7.22 (d, 1 H), 6.99 (s, 1 H), 4.00 (s, 3 H); $^{19}$F NMR (400 MHz, CDCl$_{3}$) δ ppm-103.46.

Example 7i

N-((3-Bromo-4-fluorophenyl)(2-cyano-3-fluorophenyl)methylene)-2-methylpropane-2-sulfinamide

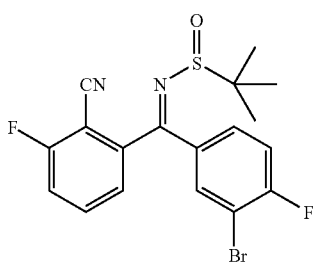

2-(3-Bromo-4-fluoro-benzoyl)-6-fluoro-benzonitrile (7.9 g, 24.5 mmol) dissolved in dry THF (40 mL) was added to a solution of titanium (IV) ethoxide (12.7 ml, 61.3 mmol) in dry THF (30 mL) at room temperature. 2-Methyl-2-propanesulfinamide (3.57 g, 29.4 mmol) was added and the resulting mixture was heated at reflux temperature for 22 h. The reaction mixture was cooled to room temperature and methanol (120 mL) was added, followed by addition of saturated sodium bicarbonate (12 mL). The resulting suspension was filtered through a pad of sodium sulfate and the solids were washed thoroughly with ethyl acetate. The filtrate was concentrated in vacuo and purified by flash column chromatography using a gradient of 30-50% ethyl acetate in hexanes to afford 5.7 g (55% yield) of the title compound.

$^{1}$H NMR (400 MHz, CDCl$_{3}$) δ ppm 7.81 (m, 1 H), 7.72-7.67 (m, 1 H), 7.48 (m, 1 H), 7.36-7.32 (m, 1 H), 7.22 (m, 1 H), 7.19 (t, 1 H), 1.37 (s, 9 H); $^{19}$F NMR (400 MHz, CDCl$_{3}$) δ ppm-99.65, -100.18, -104.55, -105.17; MS (ES+) m/z 424.94, 426.95 [M+1]$^{+}$ Example 8i N-((3-Bromophenyl)(2-cyano-3-fluorophenyl)methylene)-2-methylpropane-2-sulfinamide

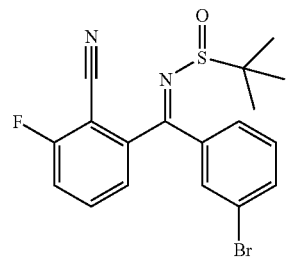

The title compound was synthesized as described for Example 71 in 78% yield starting from 2-(3-bromobenzoyl)-6-fluorobenzonitrile (10 g, 32.88 mmol):

MS (ES+) m/z 407, 409 [M+1]$^{+}$.

Example 9i

N-((5-bromo-2-fluorophenyl)(2-cyano-3-fluorophenyl)methylene)-2-methylpropane-2-sulfinamide

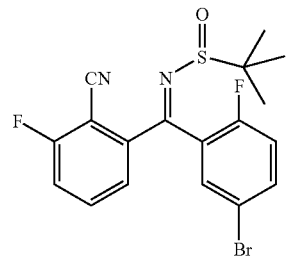

The title compound was synthesized as described for Example 71 in 59% yield starting from 2-(5-bromo-2-fluoro-benzoyl)-6-fluoro-benzonitrile (7.9 g, 24.5 mmol).

$^{1}$H NMR (400 MHz, CDCl$_{3}$) δ ppm 7.62-7.58 (m, 2H), 7.37-7.06 (m, 4H), 1.41 (s, 9H);

¹⁹F NMR (400 MHz, CDCl₃) δ ppm-103.44, -105.53, -112.29, -113.76; MS (ES+) m/z 425.00, 427.02 [M+1]⁺

Example 10i

N-((2-Cyano-3-fluorophenyl)(2-methoxypyridin-4-yl)methylene)-2-methylpropane-2-sulfinamide

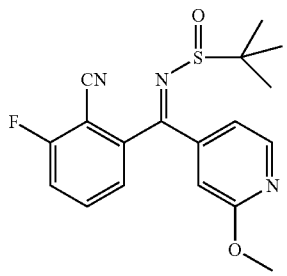

The title compound was synthesized as described for Example 71 in 49% yield starting from 2-Fluoro-6-(2-methoxy-pyridine-4-carbonyl)-benzonitrile (8.2 g, 32.0 mmol)
¹H NMR (400 MHz, CDCl₃) δ ppm 8.27 (d, 1 H), 7.68 (m, 1 H), 7.32 (t, Hz, 1 H), 7.20 (d, 1 H), 7.12 (m, 1 H), 6.99 (s, 1 H), 3.96 (s, 3 H), 1.39 (s, 9 H).
¹⁹F NMR (400 MHz, CDCl₃) δ ppm-105.02, -105.36; MS (ES+) m/z 360.08 [M+1]⁺

Example 11i 1-(3-Bromo-4-fluorophenyl)-4-fluoro-1-(pyridin-4-yl)-1H-isoindol-3-amine

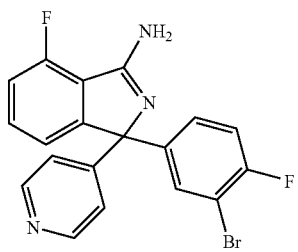

A solution of 4-iodopyridine (0.530 g, 2.59 mmol) in THF (5 mL) was added dropwise to a is mixture of tert-butyllithium (1.6 M in pentane, 2.94 mL, 4.70 mmol) in THF (20.00 mL) at −100° C. under an argon atmosphere. N-((3-Bromo-4-fluorophenyl)(2-cyano-3-fluorophenyl)methylene)-2-methylpropane-2-sulfinamide (1.00 g, 2.35 mmol) in THF (7.50 mL) was added and the resulting reaction mixture was stirred at −100° C. for 30 min. The cooling bath was removed and the mixture was stirred at room temperature for 2 h. Water was added and the mixture was extracted with EtOAc (×3). The combined organic layers were dried over Na₂SO₄ and concentrated. The residue was dissolved in MeOH (15.00 mL), and then hydrogen chloride (2 M in diethyl ether, 2.351 mL, 4.70 mmol) was added and the mixture was stirred at room temperature for 1.5 h. The solvents were removed in vacuo, and the residue was partitioned between aqueous sodium bicarbonate (saturated) and chloroform. The combined organic layers were dried (Na₂SO₄), filtered and concentrated in vacuo. Purification by silica gel chromatography using a gradient of 0 to 10% (3.5 M ammonia in methanol) in dichloromethane afforded 0.088 g (9% yield) of the title compound. MS (ES+) m/z 400 [M+1]⁺.

Example 12i 1-(3-Bromophenyl)-4-fluoro-1-(pyridin-4-yl)-1H-isoindol-3-amine

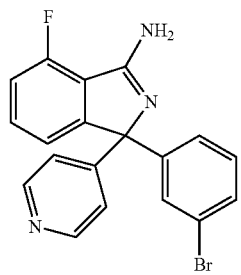

The title compound was synthesized as described for Example 11i in 88% yield, starting from N-((3-bromophenyl)(2-cyano-3-fluorophenyl)methylene)-2-methylpropane-2-sulfinamide (4.07 g, 10 mmol). MS (ES+) m/z 382, 384 [M+1]⁺.

Example 13i 1-(3-Bromophenyl)-4-fluoro-1-(4-methoxyphenyl)-1H-isoindol-3-amine

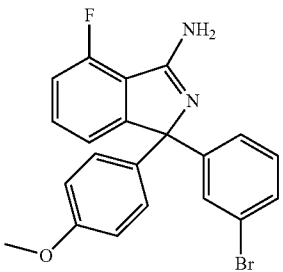

4-Methoxyphenylmagnesium bromide (6.00 mL, 3.00 mmol) was added to a solution of N-((3-bromophenyl)(2-cyano-3-fluorophenyl)methylene)-2-methylpropane-2-sulfinamide (0.407 g, 1 mmol) in THF (10 mL) at 0° C. under an argon atmosphere. The resulting mixture was stirred and allowed to reach r.t. over night, then quenched with saturated aqueous NH₄Cl, diluted with saturated aqueous NaHCO₃ and extracted with DCM. The combined organics were passed through a phase separator (Sorbent) and concentrated. The residue was dissolved in MeOH (10 mL), and hydrogen chloride (2M in diethyl ether, 2 mL, 4 mmol) was added and the resulting mixture was stirred at r.t for 2.5 h. The mixture was concentrated in vacuo and purified on a silica gel column eluted with 0-5% 0.1M NH₃ in MeOH in DCM to afford 0.39 g (95% yield) of the title compound: MS (ES+) m/z 411, 413 [M+1]⁺.

Example 14i 1-(3-Bromo-4-fluorophenyl)-4-fluoro-1-(pyrimidin-5-yl)-1H-isoindol-3-amine

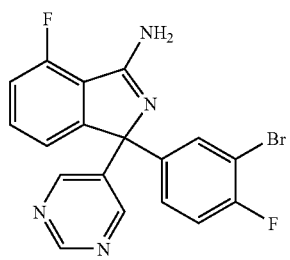

n-Butyllithium (0.136 mL, 0.34 mmol) was slowly added to 5-bromopyrimidine (50 mg, 0.31 mmol) in THF (1.0 mL) at −78° C. under argon atmosphere. The reaction mixture was stirred for 45 min. N-((3-Bromo-4-fluorophenyl)(2-cyano-3-fluorophenyl)methylene)-2-methylpropane-2-sulfinamide (111 mg, 0.26 mmol) in THF (1.0 mL) was added dropwise and the resulting reaction mixture was stirred at −78° C. for 1 h, and then allowed to reach room temperature. The reaction was quenched with water and extracted with ethyl acetate (×3). The combined organic layers were washed with brine and concentrated in vacuo. The residue was dissolved in methanol (2.0 mL) and hydrochloric acid (2.0 M in diethyl ether, 0.393 mL, 0.79 mmol) was added at room temperature. The mixture was stirred over night, and then concentrated in vacuo. The residue was partitioned between aqueous sodium bicarbonate (saturated) and ethyl acetate (×3). The combined organic layers were dried (Na₂SO₄), filtered and concentrated in vacuo. Purification by silica gel chromatography using a gradient of 0 to 10% (3.5 M ammonia in methanol) in dichloromethane gave the title compound (59.4 mg, 56% yield). MS (ES+) m/z 401, 403 [M+1]⁺.

Example 15i 1-(5-Bromo-2-fluorophenyl)-4-fluoro-1-(2-methylpyridin-4-yl)-1H-isoindol-3-amine

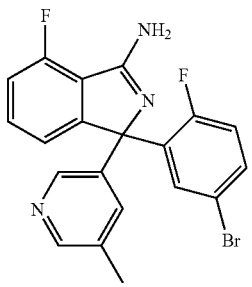

The title compound was synthesized as described for Example 14i in 15% yield, starting from N-((5-bromo-2-fluorophenyl)(2-cyano-3-fluorophenyl)methylene)-2-methylpropane-2-sulfinamide (100 mg, 0.24 mmol) and 4-bromo-2-methylpyridine (44.5 mg, 0.26 mmol). Purification was achieved by preparative HPLC.

¹H NMR (500 MHz, DMSO-d₆, 298 K) δ ppm 8.30 (d, 1 H), 7.51-7.62 (m, 3 H), 7.42 (dd, 1 H), 7.29-7.36 (m, 1 H), 7.19 (dd, 1 H), 6.98 (s, 1 H), 6.91 (dd, 1 H), 6.79 (br. s., 2 H), 2.37 (s, 3 H); MS (ES+) m/z 414, 416 [M+1]⁺.

Example 16i 1-(5-Bromo-2-fluorophenyl)-4-fluoro-1-(2-(trifluoromethyl)pyridin-4-yl)-1H-isoindol-3-amine

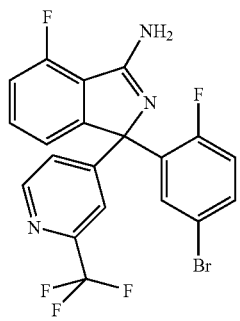

The title compound was synthesized as described for example 11i in 90% yield starting from N-((5-bromo-2-fluorophenyl)(2-cyano-3-fluorophenyl)methylene)propane-2-sulfinamide (0.980 g, 2.38 mmol) and 4-bromo-2-(trifluoromethyl)pyridine (0.646 g, 2.86 mmol). Purification was achieved by flash chromatography using a gradient of 100% CH₂Cl₂ to 30% 0.1M NH₃ in MeOH in CH₂Cl₂.

¹H NMR (500 MHz, DMSO-d₆) δ ppm 8.66 (d, 1 H) 7.66-7.50 (m, 5 H) 7.41-7.32 (m, 2 H) 7.24-7.17 (m, 1 H) 6.93 (br. s., 2 H), MS (ES+) m/z 468, 470 [M+1]⁺.

Example 17i

4-Methoxy-2-(tributylstannyl)pyridine

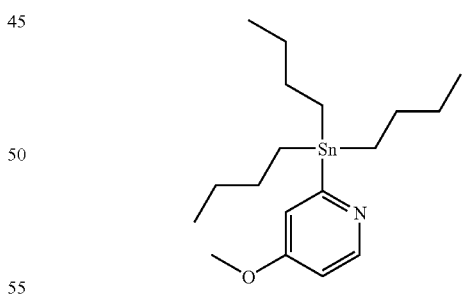

*Biological & Pharmaceutical Bulletin* (2006), 29(10), 2046-2050

A solution of 2-bromo-4-methoxypyridine (2.50 g, 13.30 mmol) in dry THF (30.0 mL) was added dropwise to a mixture of n-butyllithium (2.5 M in hexane) (5.32 mL, 13.30 mmol) and isopropylmagnesium bromide (1 M in THF) (6.65 mL, 6.65 mmol) in dry THF (20.0 mL) at −78° C. The reaction mixture was stirred at −78° C. for 30 min where after tri-n-butyltin chloride (3.97 mL, 14.63 mmol) was added and the mixture was stirred at −78° C. for 5 min. The mixture was allowed to reach room temperature and stirring was continued for 2 h. The reaction mixture was concentrated in vacuo. The residue was partitioned between water/brine and dichloromethane. The organic phase was filtered through celite and Na₂SO₄. The filtrate was concentrated in vacuo to give the title compound in quantitative yield which was used as such in next step. MS (ES+) m/z 400 [M+H]⁺.

Example 18i 1-(3-Bromophenyl)-4-fluoro-1-(2-methoxypyridin-4-yl)-1H-isoindol-3-amine

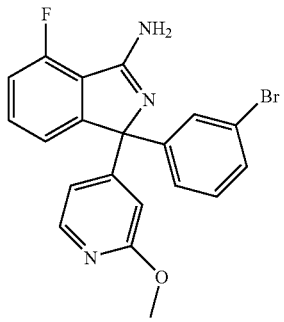

n-Butyllithium (1.7 mL, 4.17 mmol) (2.5 M in hexanes) was dropwise added to 1,3-dibromobenzene (0.504 mL, 4.17 mmol) in diethyl ether (25.00 mL) at −78° C. under argon. The resulting mixture was stirred at −78° C. for 1 h. Additional n-butyllithium (2.5 M in hexanes) (0.8 mL, 2.00 mmol) was added and the resulting reaction mixture was stirred at −78° C. for 30 min. N-((2-Cyano-3-fluorophenyl)(2-methoxypyridin-4-yl)methylene)-2-methylpropane-2-sulfinamide (1.500 g, 4.17 mmol) in diethyl ether (10.00 mL) was added dropwise and stirring was continued for 1 h at −78° C. Hydrochloric acid (25.04 mL, 12.52 mmol) (0.5 M in methanol) was added and the resulting reaction mixture was stirred at room temperature over night and concentrated in vacuo. The residue was partitioned between aqueous sodium bicarbonate (sat.) and ethyl acetate (×3). The combined organic layers were dried (Na₂SO₄), filtered and concentrated in vacuo. Purification by silica chromatography using 0% to 5% (3.5 M ammonia in methanol) in dichloromethane gave the title compound 0.812 g, (47% yield).
¹H NMR (500 MHz, DMSO-d₆) δ ppm 8.05 (d, 1 H), 7.63 (d, 1 H), 7.53 (td, 1 H), 7.46 (ddd, 1 H), 7.42 (t, 1 H), 7.23-7.32 (m, 3 H), 6.87 (dd, 1 H), 6.71 (br. s., 2 H), 6.61 (d, 1 H), 3.79 (s, 3 H); MS (ES+) m/z 412, 414 [M+H]⁺.

Example 19i 1-(3-Bromo-4-fluorophenyl)-4-fluoro-1-(2-(trifluoromethyl)pyridin-4-yl)-1H-isoindol-3-amine

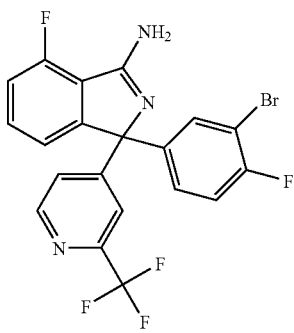

The title compound was synthesized as described for Example 11i in 35% yield, starting from of 4-bromo-2-(trifluoromethyl)pyridine (0.159 g, 0.71 mmol) and N-((3-bromo-4-fluorophenyl)(2-cyano-3-fluorophenyl)methylene)-2-methylpropane-2-sulfinamide (0.300 g, 0.71 mmol);
¹H NMR (500 MHz, DMSO-d₆) δ ppm 8.70 (d, 1 H), 7.76 (d, 1 H), 7.67 (d, 1 H), 7.64 (ddd, 1 H), 7.53-7.63 (m, 2 H), 7.27-7.42 (m, 3 H), 6.86 (br. s., 1 H); MS (ES+) m/z 468, 470 [M+H]⁺.

Example 20i 1-(3-bromo-4-fluorophenyl)-4-fluoro-1-(pyridin-4-yl)-1H-isoindol-3-amine

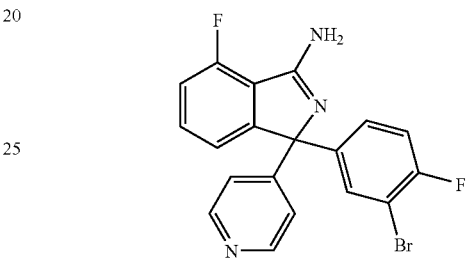

The title compound was synthesized as described for example 11i in 37% yield, starting from 4-iodopyridine (0.530 g, 2.59 mmol) and N-((3-bromo-4-fluorophenyl)(2-cyano-3-fluorophenyl)methylene)-2-methylpropane-2-sulfinamide (1.00 g, 2.35 mmol).

MS (ES+) m/z 400 [M+H]⁺.

n-Butyllithium (0.254 mL, 0.63 mmol) was dropwise added to 4-bromo-2-(difluoromethyl)pyridine (120 mg, 0.58 mmol) in anhydrous THF (5.00 mL) at −78° C. under argon atmosphere. The reaction mixture was stirred for 25 min. N-((3-bromophenyl)(2-cyano-3-fluorophenyl)methylene)-2-methylpropane-2-sulfinamide (235 mg, 0.58 mmol) in anhydrous THF (5.00 mL) was dropwise added. The reaction mixture was stirred for 2 h, then methanol (5 mL) was added and the temperature was allowed to reach room temperature. The reaction mixture was partitioned between aqueous ammonium chloride and ethyl acetate. The aqueous phase was extracted with ethyl acetate (×3). The combined organic layers were dried (Na₂SO₄), filtered and concentrated in vacuo. The residue was purified by prep. HPLC to afford the title compound (47.1 mg, 18%).

¹H NMR (500 MHz, DMSO-d₆) δ ppm 8.60 (d, 1 H) 7.67 (d, 1 H) 7.57 (td, 1 H) 7.52-7.55 (m, 1 H) 7.45-7.50 (m, 2 H)

7.42-7.45 (m, 1 H) 7.25-7.35 (m, 3 H) 6.92 (t, 1 H) 6.77 (br. s., 1 H); MS (ES+) m/z 432, 434 [M+H]$^+$.

Example 21i

4-Bromo-2-cyclopropylpyridine

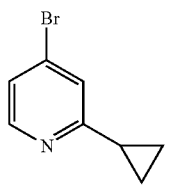

To a solution of 2,4-dibromopyridine (3.00 g, 12.66 mmol) in dry tetrahydrofuran (10 mL) under an atmosphere of argon was added tetrakis(triphenylphosphine)palladium(0) (0.435 g, 0.38 mmol). The reaction vessel was put in a water-bath (~20° C.) and cyclopropylzinc(II) bromide, 0.5M in tetrahydrofuran (30.1 mL, 15.05 mmol) was added is over a period of 10 minutes. The reaction mixture was stirred at 20° C. for 80 minutes. More cyclopropylzinc(II) bromide, 0.5M in tetrahydrofuran (7.52 mL, 3.76 mmol) was added and the reaction mixture was stirred for another 40 minutes before it was poured into saturated aqueous NaHCO$_3$ (100 mL) and diluted with EtOAc (100 mL). The layers were separated and the aqueous layer extracted with EtOAc (50 mL). The organics were combined, dried (Na$_2$SO$_4$), filtered and the solvent was evaporated at reduced pressure. The crude was purified by flash chromatography on silica gel to afford 2.12 g (85%) of the title compound.

$^1$H NMR (400 MHz, CDCl$_3$) δ ppm 8.25 (d, 1 H) 7.33 (d, 1 H) 7.21 (dd, 1 H) 1.93-2.06 (m, 1 H) 0.98-1.08 (m, 4 H); MS (CI+) m/z 198, 200 [M+H]$^+$ Example 22i 1-(3-Bromophenyl)-1-(2-cyclopropylpyridin-4-yl)-4-fluoro-1H-isoindol-3-amine

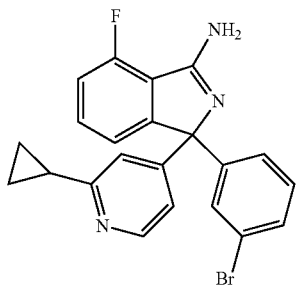

Under an atmosphere of argon, tert-butyllithium (0.731 mL, 1.24 mmol) was added drop wise over 3 minutes to tetrahydrofuran (5 mL) in a flask cooled in a liquid nitrogen-pentane bath at an external temperature between −105 to −120° C. To the solution was added drop wise over a period of 6 minutes 4-bromo-2-cyclopropylpyridine (123 mg, 0.62 mmol) dissolved in anhydrous tetrahydrofuran (2 mL). The solution was stirred for 4 minutes before drop wise addition of N-((3-bromophenyl)(2-cyano-3-fluorophenyl)methylene)-2-methylpropane-2-sulfinamide (253 mg, 0.62 mmol) dissolved in anhydrous tetrahydrofuran (2 mL) over a period of 10 minutes. The reaction mixture was stirred at a temperature below −100° C. for 45 minutes. MeOH (5.0 mL) was added at −100° C. and then hydrogen chloride-methanol solution (0.745 mL, 0.93 mmol) was added at −90° C. The reaction was left to stir overnight (17 h) and was allowed to reach ambient temperature. The solvents were evaporated and the residue was partitioned between EtOAc (25 mL) and saturated aqueous NaHCO$_3$ (25 mL). The aqueous layer was extracted with EtOAc (25 mL). The organics were combined, dried (Na$_2$SO$_4$), filtered and evaporated. The crude was purified by flash chromatography on silica gel and gave 100 mg (38%) of the title compound. MS (ES+) m/z 422, 424 [M+H]$^+$ Example 23i 1-(3-Bromophenyl)-1-(2-(difluoromethyl)-6-methylpyridin-4-yl)-4-fluoro-1H-isoindol-3-amine

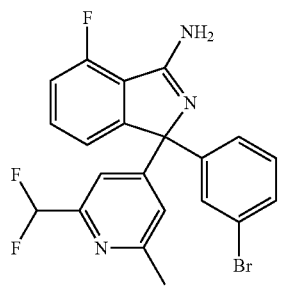

n-Butyllithium (0.359 mL, 0.90 mmol) was added to 4-bromo-2-(difluoromethyl)-6-methylpyridine (166 mg, 0.75 mmol) in THF (5 mL) at −78° C. under nitrogen atmosphere. The reaction mixture was stirred for 30 min before (E)-N-((3-bromophenyl)(2-cyano-3-fluorophenyl)methylene)-2-methylpropane-2-sulfinamide (335 mg, 0.82 mmol) in THF (2 mL) was added. The reaction was kept at −78° C. for 1 hour and then allowed to reach room temperature. The reaction was quenched with water and extracted with ethyl acetate (×3). The combined organic layers were washed with brine and concentrated in vacuo. The residue was dissolved in methanol (2.0 mL) and then hydrochloric acid (2.0 M in diethyl ether, 0.393 mL, 0.79 mmol) was added at room temperature. The mixture was stirred over night and then concentrated in vacuo. The residue was partitioned between aqueous sodium bicarbonate (saturated) and ethyl acetate (×3). The combined organic layers were dried (Na$_2$SO$_4$), filtered and concentrated in vacuo. Purification by silica gel chromatography using a gradient of 0 to 10% (3.5 M ammonia in methanol) in dichloromethane gave the title compound 40 mg (12%). MS (ES+) m/z 446, 448 [M+1]$^+$.

Example 24i 1-(2-Chloropyridin-4-yl)-1-(2-(difluoromethyl)-6-methylpyridin-4-yl)-4-fluoro-1H-isoindol-3-amine

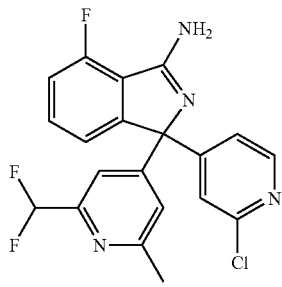

n-Butyllithium (1.174 mL, 2.94 mmol) was added to 4-bromo-2-(difluoromethyl)-6-methylpyridine (543 mg, 2.45 mmol) in THF (15 mL) at −78° C. under nitrogen atmosphere. The reaction was stirred for 30 min before (E)-N-((2-chloropyridin-4-yl)(2-cyano-3-fluorophenyl)methylene)-2-methylpropane-2-sulfinamide (890 mg, 2.45 mmol) in THF (5 mL) was added. The reaction was kept at −78° C. for 1 hour and then allowed to reach room temperature. MeOH (15 mL) was added followed by hydrochloric acid in diethylether (7.34 mL, 7.34 mmol) and the reaction was stirred for 1 hour. NaHCO$_3$(sat) was added and the mixture was extracted with EtOAc (×2). The combined organic phases were dried and concentrated to give 0.5 g (51%) of the title compound, which was used without further purification. MS (ES+) m/z 403 [M+1]$^+$.

Example 25i 1-(2-Bromopyridin-4-yl)-4-fluoro-1-(3-fluoro-4-methoxy-5-methylphenyl)-1H-isoindol-3-amine

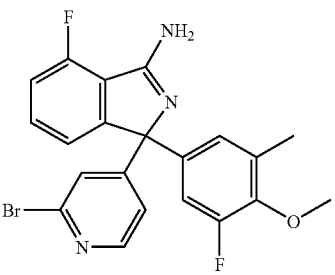

The title compound was synthesized as described in Example 24i starting from 5-bromo-1-fluoro-2-methoxy-3-methylbenzene (177 mg, 0.81 mmol) and (E)-N-((2-bromopyridin-4-yl)(2-cyano-3-fluorophenyl)methylene)-2-methylpropane-2-sulfinamide (300 mg, 0.73 mmol) to give the title compound which was used without further purification (330 mg, 99%). MS (ES+) m/z 444, 446 [M+1]$^+$.

Example 26i 1-(2-Bromopyridin-4-yl)-4-fluoro-1-(4-methoxy-3,5-dimethylphenyl)-1H-isoindol-3-amine

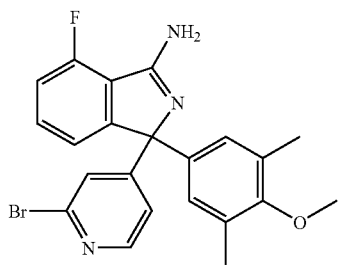

The title compound was synthesized as described in Example 24i starting from 5-bromo-2-methoxy-1,3-dimethylbenzene (190 mg, 0.88 mmol) and (E)-N-((2-bromopyridin-4-yl)(2-cyano-3-fluorophenyl)methylene)-2-methylpropane-2-sulfinamide (300 mg, 0.73 mmol) to give the title compound which was used without further purification (400 mg, quant.).

MS (ES+) m/z 440, 442 [M+1]$^+$.

Example 27i 1-(2-Bromopyridin-4-yl)-4-fluoro-1-(5-methoxy-4,6-dimethylpyridin-2-yl)-1H-isoindol-3-amine

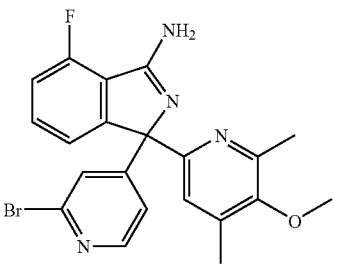

n-Butyllithium (0.229 mL, 0.57 mmol) was added to 6-bromo-3-methoxy-2,4-dimethylpyridine (124 mg, 0.57 mmol) in THF (7 mL) at −78° C. under nitrogen atmosphere. The reaction was stirred for 30 min before (E)-N-((2-bromopyridin-4-yl)(2-cyano-3-fluorophenyl)methylene)-2-methylpropane-2-sulfinamide (180 mg, 0.44 mmol) in THF (2 mL) was added. The reaction was kept at −78° C. for 1 hour and then allowed to reach room temp. Methanol (5 mL) was added followed by hydrochloric acid in diethylether (1.323 mL, 1.32 mmol) and the reaction mixture was stirred 1 hour at room temperature. NaHCO$_3$(sat) was added and the mixture was extracted with EtOAc (×2). The combined organic phases were dried and concentrated to give the title compound (200 mg, 97%), which was used without further purification. MS (ES+) m/z 441, 443 [M+1]+.

Example 28i 2-(Trimethylstannyl)isonicotinonitrile

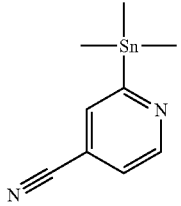

2-Bromo-isoniconinonitrile (1.00 g, 5.46 mmol) was dissolved in toluene (25 mL) and 1,1,1,2,2,2-hexamethyldistannane (2.266 mL, 10.93 mmol) and tetrakis(triphenylphosphine)palladium(0) (0.316 g, 0.27 mmol) were added and the reaction was stirred at 80° C. over night under nitrogen atmosphere. The mixture was cooled to room temperature and filtered through a pad of Celite® twice and concentrated. Toluene (20 mL) was added and the mixture was concentrated to give the title compound (1.079 g, 74%), which was used without further purification in the next step. MS (EI+) m/z 268 [M]+.

Example 29i

4-Bromopicolinaldehyde

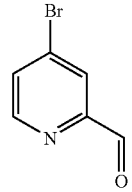

Manganese(IV) oxide (22.19 g, 255.29 mmol) was added to a solution of (4-bromopyridin-2-yl)methanol (4.00 g, 21.27 mmol) in chloroform (80 mL) and the reaction mixture was stirred under reflux for 45 min. After the mixture had cooled to room temperature the solids were removed by filtration through a pad of Celite®. The solvent was removed in vacuo and the residue (3.96 g, quant.) was used without further purification in the next step.

$^1$H NMR (500 MHz, DMSO-$d_6$) δ ppm 9.97 (s, 1 H) 8.80 (d, 1 H) 7.98 (d, 1 H) 7.88 (dd, 1 H); MS (APCI+): m/z 186, 188 [M+H]+.

Example 30i

4-Bromo-2-(difluoromethyl)pyridine

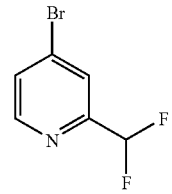

Diethylaminosulphur trifluoride (4.08 mL, 33.31 mmol) was added to 4-bromopicolinaldehyde (0.267 M in chloroform) (100 mL, 26.7 mmol) at 0° C. under an atmosphere of argon. The reaction mixture was stirred over night while the temperature was raised to room temperature. The reaction was quenched by addition of aqueous sodium bicarbonate (sat.) and was further diluted with dichloromethane. The solids were filtered off through a pad of Celite®. The organic layer was collected and the water phase was extracted with dichloromethane (×3). The organic layers were pooled, dried (Na$_2$SO$_4$), filtered and concentrated. Purification by silica chromatography using 0 to 60% diethyl ether in pentane gave the title compound (1.78 g, 32%).

$^1$H NMR (400 MHz, DMSO-$d_6$) δ ppm 8.59 (d, 1 H) 7.98 (d, 1 H) 7.90 (dt, 1 H) 6.98 (t, 1 H); MS (APCI+) m/z 208, 210 [M+H]+.

Example 31i 1-(3-Bromophenyl)-1-(2-(difluoromethyl)pyridin-4-yl)-4-fluoro-1H-isoindol-3-amine

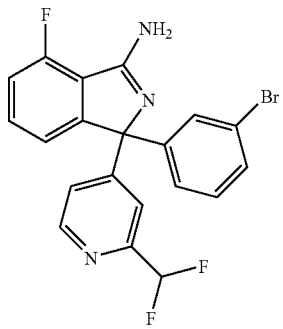

n-Butyllithium (0.254 mL, 0.63 mmol) was dropwise added to 4-bromo-2-(difluoromethyl)pyridine (120 mg, 0.58 mmol) in anhydrous THF (5.00 mL) at −78° C. under argon atmosphere. The reaction mixture was stirred for 25 min. N-((3-bromophenyl)(2-cyano-3-fluorophenyl)methylene)-2-methylpropane-2-sulfinamide (235 mg, 0.58 mmol) in anhydrous THF (5.00 mL) was dropwise added. The reaction mixture was stirred for 2 h, then methanol (5 mL) was added and the temperature was allowed to reach room temperature.

The reaction mixture was partitioned between aqueous ammonium chloride and ethyl acetate. The aqueous phase was extracted with ethyl acetate (×3). The combined organic layers were dried (Na$_2$SO$_4$), filtered and concentrated in vacuo. The residue was purified by prep. HPLC to afford the title compound (47.1 mg, 18%).

$^1$H NMR (500 MHz, DMSO-d$_6$) δ ppm 8.60 (d, 1 H) 7.67 (d, 1 H) 7.57 (td, 1 H) 7.52-7.55 (m, 1 H) 7.45-7.50 (m, 2 H) 7.42-7.45 (m, 1 H) 7.25-7.35 (m, 3 H) 6.92 (t, 1 H) 6.77 (br. s., 1 H); MS (ES+) m/z 432, 434 [M+H]$^+$.

Example 32i 1-(2-Bromopyridin-4-yl)-1-(2-(difluoromethyl)pyridin-4-yl)-4-fluoro-1H-isoindol-3-amine

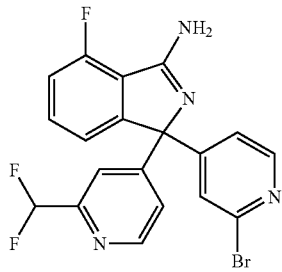

n-Butyllithium (2.5 M in hexane) (0.353 mL, 0.88 mmol) was added to 4-bromo-2-(difluoromethyl)pyridine (183 mg, 0.88 mmol) in THF (7 mL) at −78° C. under argon atmosphere. The reaction was stirred for 30 min before N-((2-bromopyridin-4-yl)(2-cyano-3-fluorophenyl)methylene)-2-methylpropane-2-sulfinamide (300 mg, 0.73 mmol) in THF (2 mL) was added. The reaction was kept at −78° C. for 1 hour and then allowed to reach room temperature. Methanol (5 mL) was added followed by hydrochloric acid (1 M in diethylether) (2.204 mL, 2.20 mmol) and the reaction was stirred for 1 hour at room temperature. The reaction mixture was concentrated in vacuo and the residue was partitioned between aqueous sodium bicarbonate (sat.) and ethyl acetate. The aqueous phase was extracted with EtOAc (×3). The combined organic phases were dried (Na$_2$SO$_4$), filtered and concentrated in vacuo. The residue was purified by prep. HPLC to afford the title compound (64 mg, 20%).

$^1$H NMR (400 MHz, DMSO-d$_6$) δ ppm 8.62 (d, 1 H) 8.33 (dd, 1 H) 7.76 (d, 1 H) 7.61 (td, 1 H) 7.54 (s, 1 H) 7.46-7.50 (m, 2 H) 7.32-7.40 (m, 2 H) 6.78-7.10 (m, 3 H); MS (ES+) m/z 433, 435 [M+H]$^+$.

Example 33i 1-(3-Bromophenyl)-1-(3-chloro-4-methoxyphenyl)-4-fluoro-1H-isoindol-3-amine

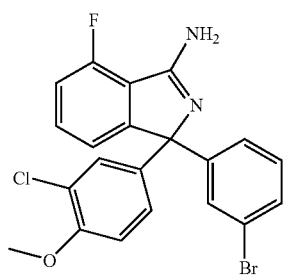

To tetrahydrofuran (20 mL) at −100° C. was added tert-butyllithium (1.7M in pentane, 4.30 mL, 7.31 mmol) dropwise over 5 min. 4-Bromo-2-chloro-1-methoxybenzene (0.81 g, 3.66 mmol) dissolved in tetrahydrofuran (5 mL) was added over 10 min. The mixture was stirred for 5 min then was (E)-N-((3-bromophenyl)(2-cyano-3-fluorophenyl)methylene)-2-methylpropane-2-sulfinamide (1.241 g, 3.05 mmol) in tetrahydrofuran (10 mL) added over 10 min. The reaction mixture was held at −100° C. for 20 min and then slowly allowed to reach r.t. over night. Hydrogen chloride-methanol solution (14.63 mL, 18.29 mmol) was added and the resulting mixture was stirred at r.t. for 1 h. The mixture was concentrated and purified on a silica gel column eluted with 0-10% 0.1M NH$_3$ in MeOH in DCM to give the title compound (570 mg, 42%). MS (ES+) m/z 445, 447 [M+1]$^+$.

Example 34i 1-(3-Chloro-4-methoxyphenyl)-4-fluoro-1-(3-(pyrimidin-5-yl)phenyl)-1H-isoindol-3-amine

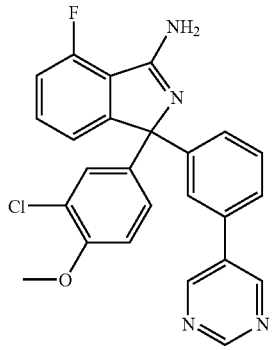

1-(3-Bromophenyl)-1-(3-chloro-4-methoxyphenyl)-4-fluoro-1H-isoindol-3-amine (570 mg, 1.28 mmol), pyrimidin-5-ylboronic acid (190 mg, 1.53 mmol), cesium carbonate (1250 mg, 3.84 mmol) and dichloro[1,1'-bis(diphenylphosphino)ferrocene]palladium (II) dichloromethane adduct (104 mg, 0.13 mmol) were dissolved in DME:EtOH:Water (6:3:1) (5 mL) and irradiated in a microwave oven for 20 min at 150° C. EtOAc, water and brine were added. The organic phase was collected, dried, filtered and then the solvent was removed under reduced pressure. The residue was purified by preparative HPLC to give 212 mg (37%) of the title product. MS (ES+) m/z 445 [M+1]$^+$.

Example 35i 1-(3-Bromophenyl)-4-fluoro-1-(5-methoxy-4,6-dimethylpyridin-2-yl)-1H-isoindol-3-amine

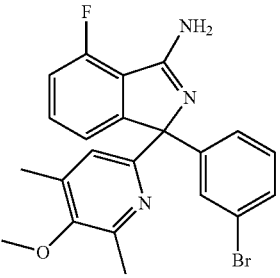

tert-Butyllithium (1.040 mL, 1.77 mmol) was added dropwise to THF (5 mL) at −100° C. under an argon atmosphere. A solution of 6-bromo-3-methoxy-2,4-dimethylpyridine (191 mg, 0.88 mmol) in THF (3 ml) was added dropwise followed by the addition of (E)-N-((3-bromophenyl)(2-cyano-3-fluorophenyl)methylene)-2-methylpropane-2-sulfinamide (300 mg, 0.74 mmol) in THF (7 ml). The resulting reaction mixture was left on the thawing cooling bath for 30 min then the cooling bath was removed and the mixture was stirred at r.t. for 1 h. Hydrogen chloride-methanol solution (3.54 mL, 4.42 mmol) was added and the resulting mixture was stirred at r.t. for 1 h. The mixture was concentrated under reduced pressure and the residue was purified on a silica gel column eluted with 0-10% 0.1 M $NH_3$ in MeOH in DCM to give the title compound (272 mg, 84%). MS (ES+) m/z 440, 442 $[M+1]^+$.

Example 36i 1-(3-Bromophenyl)-1-(2,6-dimethylpyrimidin-4-yl)-4-fluoro-1H-isoindol-3-amine

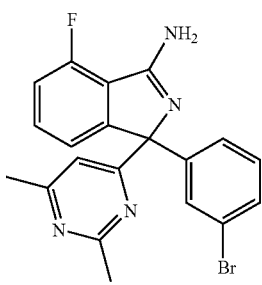

The title compound was synthesized as described for Example 35i in 35% yield, starting from of 4-bromo-2,6-dimethylpyrimidine (507 mg, 2.71 mmol) and N-((3-bromophenyl)(2-cyano-3-fluorophenyl)methylene)-2-methylpropane-2-sulfinamide (850 mg, 2.09 mmol). MS (ES+) m/z 411, 413 $[M+H]^+$.

Example 37i 1-(3-Bromophenyl)-1-(3,4-difluoro-5-methoxyphenyl)-4-fluoro-1H-isoindol-3-amine

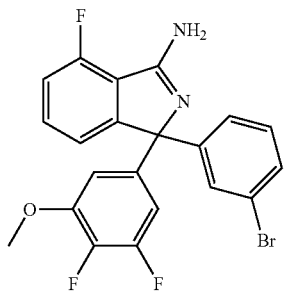

Magnesium turnings (0.692 g, 28.47 mmol) were stirred under Ar(g) for 10 min and LiCl 0.5M in THF (28.5 mL, 14.24 mmol) was added followed by DIBAL-H 1M in THF (0.228 mL, 0.23 mmol). The mixture was stirred for 5 min and then 5-bromo-1,2-difluoro-3-methoxybenzene (2.54 g, 11.39 mmol) in 5 mL THF was added in one portion and stirred for 1 h. The mixture was added to N-((3-bromophenyl)(2-cyano-3-fluorophenyl)methylene)-2-methylpropane-2-sulfinamide (4.64 g, 11.39 mmol) in THF (20 mL) and stirred 1 h. MeOH (3 mL) was added and the mixture was treated with HCl in 2.0 MeOH (22.78 mL, 22.78 mmol) for 1 h. $NaHCO_3$(sat) was added and the mixture was extracted with EtOAc. The organic phase was washed with brine, dried over $MgSO_4$ and concentrated. The residue was purified by preparative HPLC to give 714 mg (14%) of the title product as a solid. MS (ES+) m/z 447, 449 $[M+H]^+$.

Example 38i (5-(3-Amino-1-(3-bromophenyl)-4-fluoro-1H-isoindol-1-yl)-2-methoxy-3-methylphenyl)methanol

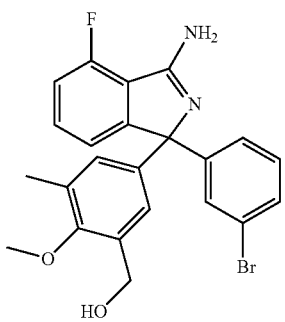

The title compound was synthesized as described for Example 35i in 54% yield, starting from of (5-bromo-2-methoxy-3-methylbenzyloxy)(tert-butyl)dimethylsilane (1.44 g, 4.17 mmol) and (E)-N-((3-bromophenyl)(2-cyano-3-fluorophenyl)methylene)-2-methylpropane-2-sulfinamide (1.415 g, 3.47 mmol). MS (ES+) m/z 455, 457 $[M+H]^+$.

Example 39i (5-(3-Amino-4-fluoro-1-(3-(pyrimidin-5-yl)phenyl)-1H-isoindol-1-yl)-2-methoxy-3-methylphenyl)methanol

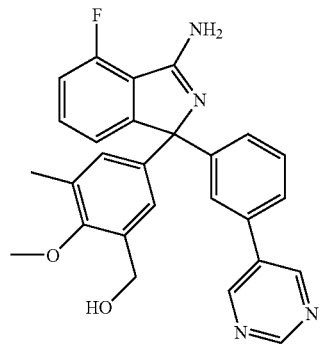

(5-(3-Amino-1-(3-bromophenyl)-4-fluoro-1H-isoindol-1-yl)-2-methoxy-3-methylphenyl)methanol (338 mg, 0.74 mmol), pyrimidine-5-boronic acid (110 mg, 0.89 mmol), cesium carbonate (726 mg, 2.23 mmol) and dichloro[1,1'-bis(diphenylphosphino)ferrocene]palladium (II) dichloromethane adduct (60.6 mg, 0.07 mmol) were dissolved in DME:EtOH:water (6:3:1) (5 mL) and irradiated in a microwave oven for 20 min at 150° C. The solvent was evaporated in vacuo and to the residue was added water, 2 M HCl solution to reach pH~7, and EtOAc. The organic phase was collected, dried and filtered. The solvent was removed under reduced pressure and the residue was purified by preparative HPLC to give 250 mg (74%) of the title compound.

$^1$H NMR (500 MHz, DMSO-d$_6$) δ ppm 9.17 (s, 1 H) 8.99 (s, 2 H) 7.57-7.72 (m, 3 H) 7.47-7.57 (m, 1 H) 7.45 (d, 2 H) 7.15-7.29 (m, 2 H) 7.02 (d, 1 H) 6.47 (br. s., 2 H) 4.85-5.11 (m, 1 H) 4.45 (br. s., 2 H) 3.61 (s, 3 H) 2.13 (s, 3 H); MS (ES+) m/z 455 (M+H)$^+$ Example 40i 1-(3-(Bromomethyl)-4-methoxy-5-methylphenyl)-4-fluoro-1-(3-(pyrimidin-5-yl)phenyl)-1H-isoindol-3-amine

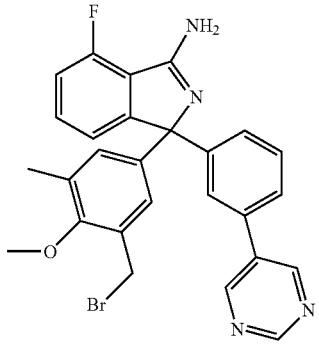

To (5-(3-amino-4-fluoro-1-(3-(pyrimidin-5-yl)phenyl)-1H-isoindol-1-yl)-2-methoxy-3-methylphenyl)methanol (250 mg, 0.55 mmol) in DCM (5 mL) was added HBr (33% in acetic acid) (5 mL, 92.08 mmol) and the mixture was stirred at rt over night. Aqueous Na$_2$CO$_3$ was added to the mixture to reach pH ~9. The water layer was extracted with DCM and the combined extracts were dried (MgSO$_4$) and concentrated under reduced pressure to afford 185 mg (65%) of the title compound. MS (ES+) m/z 517, 519 [M+H]$^+$.

Example 41i 1-(3-Bromophenyl)-4-fluoro-1-(4-fluoro-3-methoxyphenyl)-1H-isoindol-3-amine

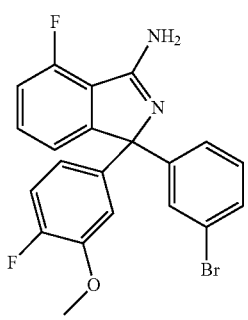

tert-Butyllithium (3.68 mL, 5.89 mmol) was added dropwise to THF (10 mL) at –100° C. under an argon atmosphere. A solution of 4-bromo-1-fluoro-2-methoxybenzene (0.604 g, 2.95 mmol) in THF (5 ml) was added dropwise followed by the addition of (E)-N-((3-bromophenyl)(2-cyano-3-fluorophenyl)methylene)-2-methylpropane-2-sulfinamide (1 g, 2.46 mmol) in THF (5 ml). The resulting reaction mixture was left on the thawing cooling bath for 30 min then the cooling bath was removed and the mixture was stirred at r.t. for 1 h. Hydrogen chloride-methanol solution (11.78 mL, 14.73 mmol) was added and the resulting mixture was stirred at r.t. for 1 h. The mixture was concentrated and purified on a silica gel column eluting with 0-10% 0.1 M NH$_3$ in MeOH in DCM to afford 0.98 g (93%) of the title compound. MS (ES+) m/z 429, 431 (M+H)$^+$ Example 42i S-Ethyl 2-bromopyridine-4-carbothioate

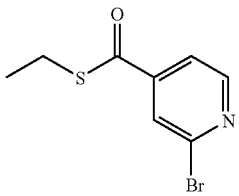

Triethylamine (3.0 g, 29.7 mmol) was added to a suspension of 2-bromo-isonicotinic acid (5.0 g, 24.8 mmol) in anhydrous dichloromethane (50 mL). The mixture was stirred at room temperature for 10 minutes, cooled to 0° C. and isobutyl chloroformate (3.6 g, 26.0 mmol) was added dropwise. The reaction mixture was then stirred at 0° C. for 30 minutes, ethanethiol (1.6 g, 25.99 mmol) was then added dropwise and the stirring was continued for an additional 2 h at 0° C. The reaction mixture was diluted with dichloromethane (100 mL) and water (100 mL). The organic layer was separated, washed with water, dried over is sodium sulfate and concentrated under reduced pressure. The residue was purified by flash column chromatography using 15% ethyl acetate in hexane to afford the title compound (5.0 g, 80%).

$^1$H NMR (400 MHz, CDCl$_3$) δ ppm 8.53 (d, 1 H) 7.93 (s, 1 H) 7.70 (dd, 1 H) 3.12 (q, 2 H) 1.37 (t, 3 H); MS (ES+) m/z: 246, 248 [M+1]$^+$ Example 43i 2-(2-Bromopyridine-4-carbonyl)-6-fluorobenzonitrile

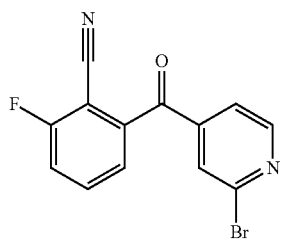

To a degassed solution of S-ethyl 2-bromopyridine-4-carbothioate (5.0 g, 20.3 mmol) in anhydrous toluene (50 mL), Pd(OAc)₂ (0.82 g, 3.66 mmol) was added followed by dropwise addition of 2-cyano-3-fluorophenylzinc iodide (0.5M in THF, 36.6 mL, 18.3 mmol). The reaction mixture was stirred at room temperature for 2 hours with continued bubbling of nitrogen. Water (50 mL) and saturated aqueous NH₄Cl (100 mL) were added and the resulting mixture was extracted with ethyl acetate (2×200 mL). The combined organic extracts were washed with brine, dried over sodium sulfate and concentrated under reduced pressure. The residue was purified by flash column chromatography using a gradient of 25% to 100% ethyl acetate in hexanes to afford 3.4 g of the title compound (1.5 g, 27%).

¹H NMR (400 MHz, CDCl₃) δ ppm 8.63 (d, 1 H) 7.73-7.83 (m, 2 H) 7.50-7.61 (m, 2 H) 7.46 (d, 1 H); MS (ES+) m/z: 305, 307 [M+1]⁺

Example 44i

N-[(2-bromopyridin-4-yl)-(2-cyano-3-fluorophenyl)methylidene]-2-methylpropane-2-sulfinamide

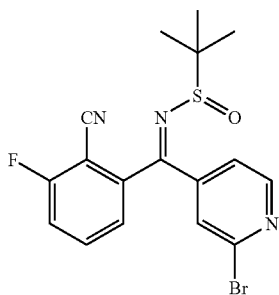

A solution of 2-(2-bromopyridine-4-carbonyl)-6-fluorobenzonitrile (3.0 g, 9.8 mmol) in dry THF (60 mL) was added to a solution of titanium (IV) ethoxide (8.0 mL, 38.6 mmol) in dry THF (20 mL) at room temperature. 2-Methyl-2-propanesulfinamide (1.8 g, 14.7 mmol) was then added in one portion and the reaction mixture was heated at reflux temperature for 40 hours. The reaction mixture was cooled to room temperature and methanol (10 mL) was added, followed by saturated sodium bicarbonate solution (10 drops). The mixture was stirred at room temperature for 1 hour, filtered through a pad of sodium sulfate, and the solids were washed thoroughly with ethyl acetate. The filtrate was concentrated under reduced pressure and the residue was purified by flash column chromatography (20-50% ethyl acetate in hexanes) to afford the title compound (2.7 g, 67.5%).

¹H NMR (400 MHz, CDCl₃) δ ppm 8.49 (d, 1 H) 7.71 (d, 1 H) 7.53 (s, 1 H) 7.36 (t, 2 H) 7.19 (d, 1 H) 1.40 (s, 9 H); MS (ES+) m/z: 408, 410 [M+1]⁺

Example 45i

6-Bromo-2,4-dimethyl-3-hydroxypyridine

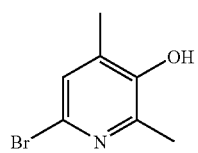

A solution of bromine (4.2 mL, 81.2 mmol) in anhydrous pyridine (80 mL) was added dropwise to a solution of 2,4-dimethyl-3-hydroxypyridine (10.0 g, 81.2 mmol) in anhydrous pyridine (160 mL). The mixture was stirred at room temperature for 1 hour, concentrated under reduced pressure and then further dried under vacuum. The residue was taken up in water (100 mL) and the resulting mixture was stirred for 0.5 hour at room temperature. The precipitated solid was collected by filtration, washed with water and air dried overnight to afford 8.7 g (53%) of the title compound.

¹H NMR (400 MHz, CDCl₃) δ ppm 7.10 (s, 1 H), 4.73 (br, s, 1 H), 2.45 (s, 3 H), 2.23 (s, 3 H)

Example 46i

6-Bromo-3-methoxy-2,4-dimethyl-pyridine

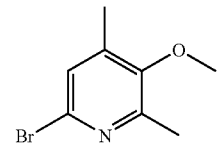

A mixture of 6-bromo-2,4-dimethyl-3-hydroxypyridine (8.7 g, 43.1 mmol), iodomethane (4.0 mL, 64.6 mmol) and potassium carbonate (11.9 g, 86.1 mmol) in acetone (250 mL) was heated at reflux temperature for 3 hours. The reaction mixture was then cooled to room temperature and filtered through a pad of Celite®. The filtrate was concentrated under reduced pressure and the residue was purified by flash column chromatography using 20% ethyl acetate in hexane to afford 7.9 g (85%) of the title compound.

¹H NMR (400 MHz, CDCl₃) δ ppm 7.14 (s, 1 H), 3.72 (s, 3 H), 2.48 (s, 3 H), 2.26 (s, 3 H) MS (ES+) m/z: 216, 218 [M+1]⁺

Example 47i 1-(3-Bromophenyl)-4-fluoro-1-(6-methoxy-5-(trifluoromethyl)pyridin-3-yl)-1H-isoindol-3-amine

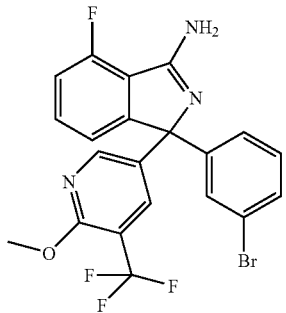

The title compound was synthesized as described for Example 14i in 71% yield, starting from N-((3-bromophenyl)(2-cyano-3-fluorophenyl)methylene)-2-methylpropane-2-sulfinamide (815 mg, 2 mmol) and 5-iodo-2-methoxy-3-(trifluoromethyl)pyridine (606 mg, 2 mmol).

¹H NMR (400 MHz, DMSO-d₆) δ ppm 8.37 (d, 1 H) 7.87 (d, 1 H) 7.72-7.77 (m, 1 H) 7.54-7.59 (m, 1 H) 7.44-7.49 (m, 2 H) 7.31-7.36 (m, 1 H) 7.24-7.31 (m, 2 H) 6.75 (br. s., 2 H) 3.95 (s, 3 H); MS (ES+) m/z 480, 482 [M+1]+.

Example 48i

3-Bromo-4-methoxybenzoyl chloride

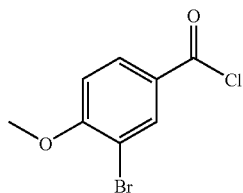

See also: *Liebigs Annalen der Chemie*, 1989, (9), 863-81.

To a solution of 3-bromo-4-methoxybenzoic acid (5.0 g, 21.64 mmol) in DCM (52 mL) oxalyl chloride (2.27 mL, 26 mmol) was added at room temperature followed by DMF (one drop). The reaction mixture was stirred for 3 h and the reaction mixture was concentrated under reduced pressure. Toluene (50 mL) was added and the mixture was concentrated under reduced pressure. This procedure was repeated twice. The product (5.4 g, quant.) was used without further purification.

Example 49i 2-(3-Bromo-4-methoxybenzoyl)-6-fluorobenzonitrile

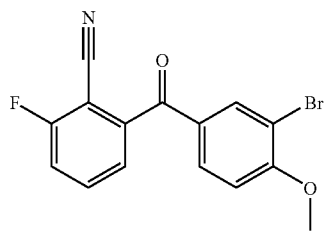

To a solution of copper(I) cyanide (1.746 g, 19.50 mmol) and lithium bromide (0.98 mL, 39 mmol) in anhydrous THF (40 mL), (2-cyano-3-fluorophenyl)zinc(II) iodide (0.5M in THF, 39 mL, 19.50 mmol) was added at −78° C. followed by addition of 3-bromo-4-methoxybenzoyl chloride (5.35 g, 21.45 mmol) in THF (40 mL). The reaction mixture was allowed to reach room temperature and stirred over night. Saturated aqueous NH$_4$Cl (40 mL) was added and the resulting mixture was concentrated under reduced pressure. The residue was diluted with water (30 ml) and extracted with DCM (3×50 mL). The combined organic extracts were passed though a phase separator (Sorbent) and concentrated under reduced pressure. The residue was purified by flash column chromatography (0-60% ethyl acetate in heptane) to afford the title compound (3.5 g, 54%).

$^1$H NMR (500 MHz, DMSO-d$_6$) δ ppm 8.02 (d, 1 H) 7.89-7.96 (m, 1 H) 7.75-7.85 (m, 2 H) 7.60 (d, 1 H) 7.30 (d, 1 H) 3.99 (s, 3 H).

Example 50i

N-[(2-Bromopyridin-4-yl)-(2-cyano-3-fluorophenyl)methylidene]-2-methylpropane-2-sulfinamide

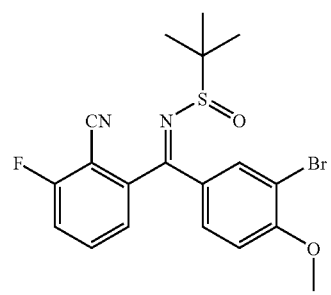

A solution of 2-(3-bromo-4-methoxybenzoyl)-6-fluorobenzonitrile (3.50 g, 10.47 mmol) in dry THF (55 mL) was added to titanium(IV) ethoxide (5.3 mL, 25.4 mmol) at room temperature. 2-Methyl-2-propanesulfinamide (1.65 g, 13.6 mmol) was added in one portion and the reaction mixture was heated at reflux temperature for 64 hours. The reaction mixture was cooled to room temperature and DCM (50 mL) was added, followed by saturated sodium bicarbonate solution (5 mL). Silica powder was added and the mixture was concentrated under reduced pressure. The residue was purified by flash column chromatography (0-60% ethyl acetate in heptane) to afford the title compound (3.1 g, 67.6%).

$^1$H NMR (400 MHz, DMSO-d$_6$) δ ppm 7.88 (br. s. 1H) 7.82 (d, 1 H) 7.67 (t, 1 H) 7.46 (br. s., 2 H) 7.21 (d, 1 H) 3.93 (s, 3 H) 1.25 (d, 9 H).

Example 51i 1-(3-Bromo-4-methoxyphenyl)-4-fluoro-1-(2-(trifluoromethyl)pyridin-4-yl)-1H-isoindol-3-amine

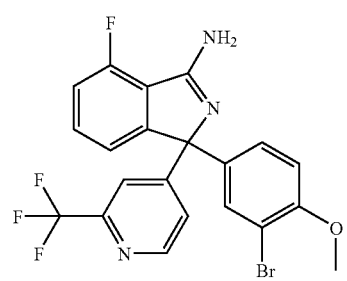

A solution of 4-bromo-2-trifluoromethylpyridine (1.76 g, 7.80 mmol) in THF (2 mL) was added dropwise at −100° C. to t-butyllithium (9.17 mL, 15.59 mmol) in THF (15 mL) followed by the addition of (E)-N-((3-bromo-4-methoxyphenyl)(2-cyano-3-fluorophenyl)methylene)-2-methylpropane-2-sulfinamide (3.1 g, 7.09 mmol) in THF (10 mL). The reaction mixture was left on a thawing cooling bath for 1 hour and then allowed to reach room temperature and stirred for 2.5 hours. Hydrochloric acid in methanol (1.25 M, 28.4 mL, 35.4 mmol) was added and the reaction was stirred for 1 hour.

Silica powder was added and the mixture was concentrated under reduced pressure. The residue was purified by flash column chromatography (0-10% 0.1M NH$_3$ in methanol in DCM) to afford the title compound (3.04 g, 89%).

$^1$H NMR (400 MHz, DMSO-d$_6$) δ ppm 8.79 (br. s., 1 H) 7.72-7.91 (m, 3 H) 7.67 (br. s., 1 H) 7.53 (br. s., 1 H) 7.45 (d, 1 H) 7.23 (dd, 1 H) 7.09-7.15 (m, 1 H) 3.84 (s, 3 H)

Example 52i

4-Fluoro-1-(4-methoxy-3-(pyrazin-2-yl)phenyl)-1-(2-(trifluoromethyl)pyridin-4-yl)-1H-isoindol-3-amine

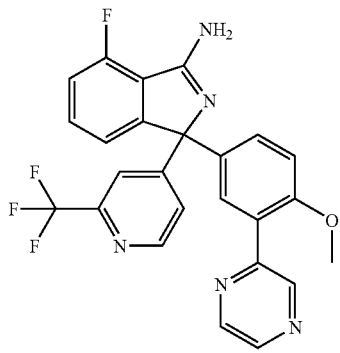

1-(3-Bromo-4-methoxyphenyl)-4-fluoro-1-(2-(trifluoromethyl)pyridin-4-yl)-1H-isoindol-3-amine (1.5 g, 3.12 mmol), 2-tributylstannylpyrazine (1.268 g, 3.44 mmol), tetrakis(triphenylphosphine)palladium(0) (0.361 g, 0.31 mmol) and DMF (10 mL) were heated in a microwave oven for 20 min at 150° C. The reaction mixture was filtered and concentrated under reduced pressure. The residue was diluted with DCM (40 ml) and silica powder was added and the mixture was concentrated under reduced pressure. The residue was purified by flash column chromatography (0-10% 0.1M NH$_3$ in Methanol in DCM) to afford the title compound (0.82 g, 54.8%).

$^1$H NMR (600 MHz, chloroform-d) δ ppm 9.12 (d, 1 H) 8.67 (d, 1 H) 8.59-8.62 (m, 1 H) 8.46 (d, 1 H) 7.71 (d, 1 H) 7.67 (d, 1 H) 7.57 (td, 1 H) 7.51-7.54 (m, 1 H) 7.42 (d, 1 H) 7.37 (dd, 1 H) 7.19 (t, 1 H) 7.02 (d, 1 H) 3.91 (s, 3 H)
MS (ES+) m/z 480 [M+1]$^+$.

Example 53i 1-(2-Bromopyridin-4-yl)-1-(2-cyclopropylpyridin-4-yl)-4-fluoro-1H-isoindol-3-amine

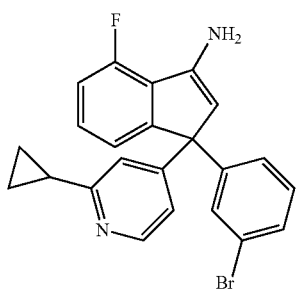

Under an atmosphere of argon, tert-butyllithium (1.7 M in pentane) (0.576 mL, 0.98 mmol) was added dropwise to anhydrous tetrahydrofuran (4.00 mL) at −100° C. 4-Bromo-2-cyclopropylpyridine (0.097 g, 0.49 mmol) in anhydrous THF (2.00 mL) was added dropwise to the mixture. The solution was stirred for 2 minutes before dropwise addition of a solution of N-((2-bromopyridin-4-yl)(2-cyano-3-fluorophenyl)methylene)-2-methylpropane-2-sulfinamide (0.200 g, 0.49 mmol) in anhydrous THF (2.00 mL). The reaction was stirred at −100° C. for 20 minutes, then the temperature was raised to −78° C. over a period of 10 minutes. The reaction was stirred at −78° C. for another 60 minutes. MeOH (2.0 mL) was added dropwise at −78° C. followed by hydrogen chloride (1.25 M in methanol) (1.176 mL, 1.47 mmol). The cooling bath was removed and the reaction was left to stir at ambient temperature for 60 minutes. The solvents were evaporated and the residue was partitioned between EtOAc and saturated aqueous NaHCO$_3$. The aqueous layer was extracted with EtOAc (×2), the organics were combined, dried (Na$_2$SO$_4$), filtered and evaporated. Purification by silica chromatography using 0 to 5% (3.5 M ammonia in methanol) in dichloromethane gave the title compound (0.094 g, 45%).

$^1$H NMR (500 MHz, DMSO-d$_6$) δ ppm 8.30 (dd, 2 H) 7.72 (d, 1 H) 7.58 (td, 1 H) 7.42-7.47 (m, 1 H) 7.37 (dd, 1 H) 7.32 (dd, 1 H) 7.18-7.22 (m, 1 H) 7.00 (dd, 1 H) 6.80 (br. s., 2 H) 1.99-2.07 (m, 1 H) 0.81-0.95 (m, 4 H); MS (ES+) m/z 423, 425 [M+1]$^+$.

Example 54i

6-Bromo-3-difluoromethoxy-2,4-dimethyl-pyridine

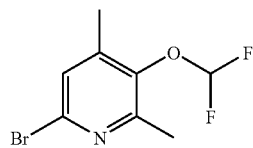

A three-necked round bottom flask (500 mL) equipped with dry ice condenser (−78° C., acetone/dry ice) was charged with a solution of 6-bromo-2,4-dimethyl-3-hydroxypyridine (7.2 g, 35.6 mmol) in i-propanol (100 mL) and aqueous sodium hydroxide solution (20%, 100 mL) was added. The reaction mixture was stirred vigorously at 40° C. for 5 hours while chlorodifluoromethane was bubbled continuously into the solution at a moderate rate. The reaction mixture was then cooled to room temperature and extracted with Et$_2$O (3×100 mL). The combined extracts were washed with water (2×50 mL), dried over magnesium sulfate and concentrated in vacuo. Purification of the crude mixture by flash column chromatography using 5% ethyl acetate in hexane afforded the title compound (5.4 g, 60%).

$^1$H NMR (400 MHz, CDCl$_3$) δ ppm 7.23 (s, 1 H) 6.40 (t, 1 H) 2.51 (s, 3 H) 2.30 (s, 3 H);

$^{19}$F NMR (376 MHz, CDCl$_3$) δ ppm-79.97.

Example 55i 2-(2-Chloro-pyridine-4-carbonyl)-6-fluoro-benzonitrile

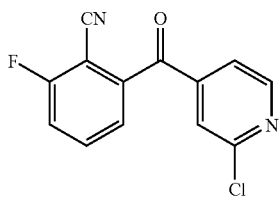

To a solution of 2-cyano-3-fluorophenylzinc iodide (0.5 M, 31 mL, 15.5 mmol) in THF was added 2-chloro-isonicotinoyl chloride (3 g, 17.05 mmol), followed by Pd(PPh$_3$)$_2$Cl$_2$ (0.33 g, 0.465 mmol). The resulting mixture was stirred at room temperature for 4 hours and diluted with ethyl acetate (80 mL) and H$_2$O (40 mL). The organic phase was separated, washed with H$_2$O (3×30 mL), dried over Na$_2$SO$_4$, filtered and concentrated under reduced pressure. The residue was purified by flash column chromatography using a gradient of 20-50% EtOAc in hexane to afford of the title compound (3.6 g, 88%).

$^1$H NMR (400 MHz, CDCl$_3$) δ ppm 8.65 (d, 1 H) 7.77 (td, 1 H) 7.63 (s, 1 H) 7.51-7.56 (m, 2 H) 7.46 (d, 1 H); MS (ES+) m/z 261 [M+1]$^+$

Example 56i

N-[(2-Chloropyridin-4-yl)(2-cyano-3-fluorophenyl)methylidene]-2-methylpropane-2-sulfinamide

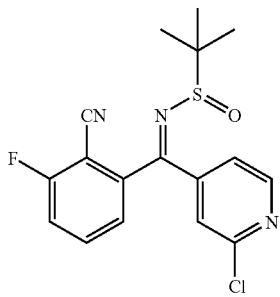

Ti(OEt)$_4$ (15 mL) was added to a solution of 2-(2-chloro-pyridine-4-carbonyl)-6-fluoro-benzonitrile (3.6 g, 13.81 mmol) and 2-methyl-propane-2-sulfinic acid amide (2.5 g, 20.72 mmol) in dry THF (100 mL) at room temperature. The resulting mixture was stirred to reflux for 40 hours and then treated with CH$_3$OH (50 mL) and saturated sodium bicarbonate solution (10 mL). The resulting suspension was filtered through a pad of Celite® and the solids were washed with THF (50 mL) and CH$_3$OH (20 mL). The filtrate was concentrated under reduced pressure and the residue was purified by flash column chromatography using a gradient of 25-50% EtOAc in hexane to afford the title compound (2.4 g, 48%).

$^1$H NMR (400 MHz, CDCl$_3$) δ ppm 8.51 (d, 1 H) 7.71 (d, 1 H) 7.39 (s, 1 H) 7.35 (d, 2 H) 7.20 (d, 1 H) 1.40 (s, 9 H); MS (ES+) m/z 364 [M+1]$^+$.

Example 57i 3-(2-Chloro-pyridin-4-yl)-3-(5-difluoromethoxy-4,6-dimethyl-pyridin-2-yl)-7-fluoro-3H-isoindol-1-ylamine

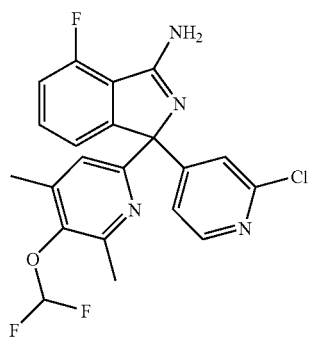

n-Butyllithium (2.5 M in hexane, 0.144 mL, 0.36 mmol) was added dropwise to a solution of 6-bromo-3-difluoromethoxy-2,4-dimethyl-pyridine (0.29 g, 1.15 mmol) in dry THF (1 mL) at −78° C. The reaction mixture was stirred for 5 minutes and a solution of N-[(2-chloro-4-pyridyl)-(2-cyano-3-fluoro-phenyl)methylene]-2-methyl-propane-2-sulfinamide (0.28 g, 0.77 mmol) in dry THF (1 mL) was added dropwise at −78° C. The stirring was continued for 1 hour, a solution of HCl in CH$_3$OH (1.25M, 1.1 mL) was added dropwise at −78° C. and the mixture was allowed to warm slowly to room temperature and stirred overnight. Dichloromethane (20 mL) and saturated sodium bicarbonate solution (50 mL) were added and the phases separated. The organic layer was washed with H$_2$O, dried over Na$_2$SO$_4$, filtered and concentrated under reduced pressure. The residue was purified by flash column chromatography using 5% CH$_3$OH in DCM to afford the title compound (120 mg, 36%).

$^1$H NMR (400 MHz, CDCl$_3$) δ ppm 8.15 (d, 1 H) 7.94 (s, 1 H) 7.79 (d, 1 H) 7.35-7.42 (m, 1 H) 7.26 (d, 1 H) 7.17-7.22 (m, 1 H) 6.97-7.07 (m, 1 H) 6.28 (s, 1 H) 2.81 (s, 3 H) 2.43 (s, 3 H); $^{19}$F NMR (376 MHz, CDCl$_3$) δ ppm-79.62, -123.41; MS (ES+) m/z 433 [M+1]$^+$.

Example 58i 5-(3-Amino-1-(3-bromophenyl)-4-fluoro-1H-isoindol-1-yl)-2-methoxy-3-methylbenzonitrile

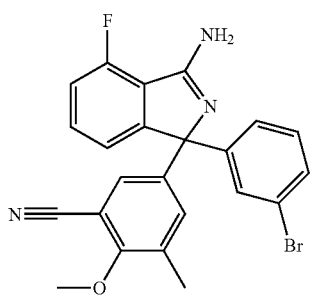

Magnesium turnings (37.3 mg, 1.53 mmol) were stirred under Ar(g) for 10 min and LiCl 0.5M in THF (1.841 mL, 0.92 mmol) was added followed by DIBAL-H 1M in THF (6.14 µL, 6.14 µmol). The mixture was stirred for 5 min and 5-bromo-2-methoxy-3-methylbenzonitrile (194 mg, 0.86 mmol) in THF (1 mL) was added in one portion and stirring was continued for 2 h. The solution was transferred via canula to N-((3-bromophenyl)(2-cyano-3-fluorophenyl)methylene)-2-methylpropane-2-sulfinamide (250 mg, 0.61 mmol) in THF (3 mL) at rt and stirred o.n. MeOH (4 mL) was added and the mixture was treated with HCl in MeOH (1.473 mL, 1.84 mmol) o.n. The solvents were removed in vacuo, and the residue was partitioned between saturated aqueous sodium bicarbonate solution and ethyl acetate. The combined organic layers were dried ($Na_2SO_4$), filtered and concentrated in vacuo. Purification by silica gel chromatography using a gradient of 0 to 2.5% (3.5 M ammonia in methanol) in dichloromethane afforded 0.088 g (32% yield) of the title compound.

$^1$H NMR (500 MHz, DMSO-$d_6$) δ ppm 7.70 (d, 1 H) 7.50-7.57 (m, 2 H) 7.39-7.47 (m, 3 H) 7.24-7.31 (m, 3 H) 6.64 (br. s., 2 H) 3.87 (s, 3 H) 2.21 (s, 3 H); MS (ES+) m/z 450, 452 [M+1]$^+$.

Example 59i 1-(3-Bromophenyl)-6-chloro-4-fluoro-1-(2-methylpyridin-4-yl)-1H-isoindol-3-amine

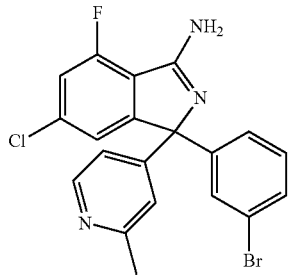

The title compound was synthesized as described for Example 11i in 83% yield, starting from N-((3-bromophenyl)(5-chloro-2-cyano-3-fluorophenyl)methylene)-2-methylpropane-2-sulfinamide (2 g, 4.53 mmol) and 4-bromo-2-methylpyridine (0.935 g, 5.43 mmol)
MS (ES+) m/z 432, 434 [M+1]$^+$.

Example 60i 3-(3-Amino-6-chloro-4-fluoro-1-(2-(trifluoromethyl)pyridin-4-yl)-1H-isoindol-1-yl)phenyl trifluoromethanesulfonate

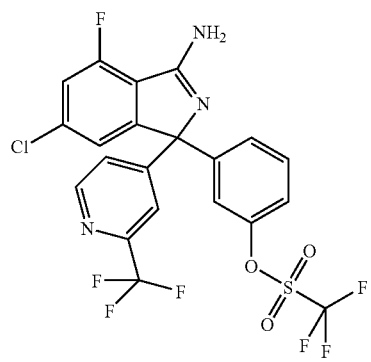

3-(3-Amino-6-chloro-4-fluoro-1-(2-(trifluoromethyl)pyridin-4-yl)-1H-isoindol-1-yl)phenol (200 mg, 0.47 mmol), N-phenylbis(trifluoromethanesulphonimide) (186 mg, 0.52 mmol), potassium carbonate (197 mg, 1.42 mmol) and THF (3 mL) were added into a vial and heated in a microwave reactor at 120° C. for 10 min. The mixture was filtered and the filtrate was purified on a silica gel column eluted with 0-5% 0.1 M $NH_3$ in MeOH in DCM to afford 75 mg (29%) of the title compound.
MS (ES+) m/z 554, 556 [M+1]$^+$.

Example 61i 3-(3-Amino-6-chloro-4-fluoro-1-(2-(trifluoromethyl)pyridin-4-yl)-1H-isoindol-1-yl)phenol

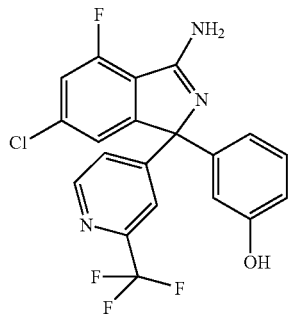

Boron tribromide (0.472 mL, 4.99 mmol) was added to a solution of 6-chloro-4-fluoro-1-(3-methoxyphenyl)-1-(2-(trifluoromethyl)pyridin-4-yl)-1H-isoindol-3-amine (870 mg, 2.00 mmol) in DCM (10 mL) at 0° C. under an argon atmosphere. The cooling bath was removed and the resulting mixture was stirred at rt for 45 min. The mixture was cooled to 0° C. and subsequently ice was added. The pH was adjusted to ~8 with 4 M aq NaOH. The DCM was removed in vacuo and the resulting residue was extracted with EtOAc. The combined organics were dried over $Na_2SO_4$, concentrated and purified on a silica gel column eluted with 0-10% 0.1M $NH_3$ in MeOH in DCM to afford 200 mg (24%) of the title compound.
MS (ES+) m/z 422, 424 [M+1]$^+$.

Example 62i

6-Chloro-4-fluoro-1-(3-methoxyphenyl)-1-(2-(trifluoromethyl)pyridin-4-yl)-1H-isoindol-3-amine

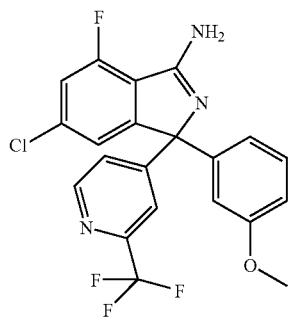

tert-Butyllithium (1.7 M in pentane, 6.59 mL, 11.20 mmol) was added dropwise to THF (10 mL) at −100° C. under an argon atmosphere. A solution of 4-bromo-2-trifluoromethylpyridine (1.266 g, 5.60 mmol) in THF (1 mL) was added dropwise followed by the addition of N-((5-chloro-2-cyano-3-fluorophenyl)(3-methoxyphenyl)methylene)-2-methylpropane-2-sulfinamide (2 g, 5.09 mmol) in THF (6 mL). The resulting reaction mixture was left on the thawing cooling bath for 30 min then the cooling bath was removed and the mixture was stirred at rt for 1.5 h. Hydrogen chloride in methanol solution (20.36 mL, 25.45 mmol) was added and the mixture was stirred at rt for 1 h. The mixture was concentrated and purified on a silica gel column eluted with 0-10% 0.1M NH$_3$ in MeOH in DCM to afford 870 mg (39%) of the title compound.

MS (ES+) m/z 436, 438 [M+1]$^+$.

Example 63i

N-((5-Chloro-2-cyano-3-fluorophenyl)(3-methoxyphenyl)methylene)-2-methylpropane-2-sulfinamide

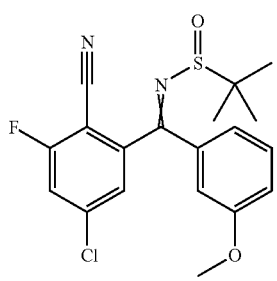

4-Chloro-2-fluoro-6-(3-methoxybenzoyl)benzonitrile (2.56 g, 8.84 mmol), 2-methyl-2-propanesulfinamide (1.392 g, 11.49 mmol) and titanium(IV) ethoxide (4.62 mL, 22.09 mmol) were dissolved in THF (30 mL) and stirred at 75° C. over weekend. When cooled to rt, the mixture was diluted with DCM (25 mL). Saturated aqueous NaHCO$_3$ (3 mL) was added followed by silica and the mixture concentrated under reduced pressure until a free flowing powder was obtained. Purification on a silica gel column (0-40% EtOAc in heptane as eluent) gave 2.04 g (59% yield) of the title compound.

MS (ES+) m/z 393, 395 [M+1]$^+$.

Example 64i

4-Chloro-2-fluoro-6-(3-methoxybenzoyl)benzonitrile

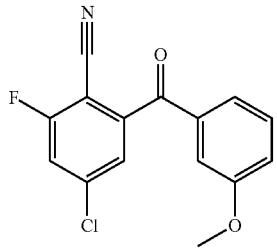

2-Bromo-4-chloro-6-fluorobenzonitrile (6.95 g, 29.64 mmol) was dissolved in THF (15 mL) and added to a bottle of Rieke® Zinc in THF (50 mg/mL, 50.0 mL, 38.24 mmol) at 0° C. under an argon atmosphere. The resulting mixture was stirred at rt for 6 h and then stored in a refrigerator for 60 h allowing the excess of zinc to settle. The solution was carefully decanted off and cooled to −78° C. under an argon atmosphere. A solution of lithium bromide (5.15 g, 59.28 mmol) and copper(I) cyanide (2.65 g, 29.64 mmol) in THF (30 mL) was added and the resulting mixture was stirred at rt for 30 min. The mixture was cooled to −78° C. and then 3-methoxybenzoyl chloride (4.17 mL, 29.64 mmol) was added dropwise. The cooling bath was removed and the resulting mixture was stirred at rt for 1.5 h. Saturated aqueous NH$_4$Cl (12 mL) was added to the mixture, the THF was removed in vacuo and the residue was diluted with water (50 mL) and DCM (50 mL). The mixture was poured into a phase separator, the organic phase was collected, concentrated and purified on a silica gel column (0-30% EtOAc in heptane) to give 4.7 g (55%) of the title compound.

MS (CI) m/z 290, 292 [M+1]$^+$.

Example 65i

N-((3-Bromophenyl)(5-chloro-2-cyano-3-fluorophenyl)methylene)-2-methylpropane-2-sulfinamide

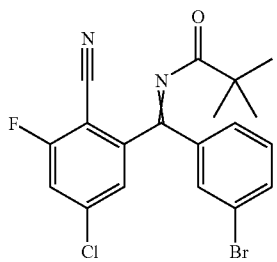

The title compound was synthesized as described for Example 63i in 55% yield starting from 2-(3-bromobenzoyl)-4-chloro-6-fluorobenzonitrile (5 g, 14.77 mmol).

MS (ES+) m/z 443, 445 [M+1]$^+$.

Example 66i 2-(3-Bromobenzoyl)-4-chloro-6-fluorobenzonitrile

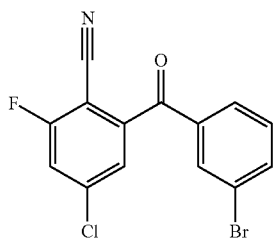

The title compound was synthesized as described for Example 64i in 55% yield starting from 2-bromo-4-chloro-6-fluorobenzonitrile (6.35 g, 27.08 mmol) and 3-bromobenzoyl chloride (3.58 mL, 27.08 mmol).

MS (CI) m/z 337, 339 [M+1]$^+$.

Example 67i

2-Bromo-4-chloro-6-fluorobenzonitrile

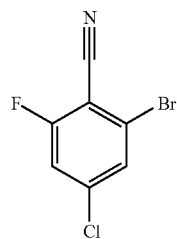

4-Chloro-2-fluoro-6-(4,4,5,5-tetramethyl-1,3,2-dioxaborolan-2-yl)benzonitrile (14 g, 49.73 mmol) was dissolved in MeOH (75 mL). A solution of copper(II) bromide (33.3 g, 149.19 mmol) in water (75 mL) was added and the resulting mixture was heated to reflux over night. When cooled to rt, the mixture was extracted with Et$_2$O (3×100 mL). The combined organics were washed with water (2×100 mL), brine (75 mL), dried over MgSO$_4$, concentrated and purified on a silica gel column eluted with 0-30% DCM in heptane to afford 6.35 g (55%) of the title compound.

MS (CI) m/z 234, 236 [M+1]$^+$.

Example 68i

4-Chloro-2-fluoro-6-(4,4,5,5-tetramethyl-1,3,2-dioxaborolan-2-yl)benzonitrile

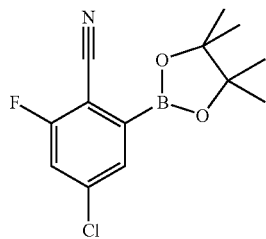

4-Chloro-2-fluorobenzonitrile (10 g, 64.29 mmol), pinacolborane (18.66 mL, 128.57 mmol), 4,4'-di-tert-butyl-2,2'-dipyridyl (0.414 g, 1.54 mmol) and di-μ-methoxobis(1,5-cyclooctadiene)diiridium(I) (0.511 g, 0.77 mmol) were dissolved in THF (125 mL) under an argon atmosphere and stirred at 50° C. over night. The mixture was concentrated and the resulting residue was passed through a plug of silica eluted with 15% MeCN in DCM to afford 14 g (77%) of the title compound.

MS (CI) m/z 282, 284 [M+1]$^+$.

Example 1

4-Fluoro-1-(2-fluoro-5-(pyrimidin-5-yl)phenyl)-1-(2-methylpyridin-4-yl)-1H-isoindol-3-amine

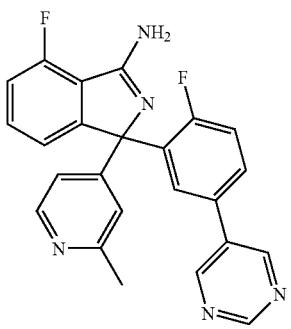

1-(5-Bromo-2-fluorophenyl)-4-fluoro-1-(2-methylpyridin-4-yl)-1H-isoindol-3-amine (80 mg, 0.19 mmol), 5-pyrimidinylboronic acid (31.1 mg, 0.25 mmol), [1,1-bis(diphenylphosphino)ferrocene]dichloropalladium(II) (15.77 mg, 0.02 mmol), potassium carbonate (2.5 M, aq, 0.290 mL, 0.58 mmol) and DMF (2 mL) were added to a vial and heated in a microwave reactor at 150° C. for 15 min. Brine was added and the product mixture was extracted EtOAc. The organic phase was dried (Na$_2$SO$_4$), filtered and concentrated in vacuo. Purification by preparative HPLC afforded 34.0 mg (43% yield) of the title compound.

$^1$H NMR (500 MHz, DMSO-d$_6$, 298 K) δ ppm 9.17 (s, 1 H), 8.99 (s, 2 H), 8.31 (d, 1 H), 7.77-7.83 (m, 1 H), 7.52-7.66 (m, 3 H), 7.27-7.40 (m, 2 H), 7.05 (s, 1 H), 6.99 (dd, 1 H), 6.74 (br. s., 2 H), 2.38 (s, 3 H); MS (ES+) m/z 414 [M+1]$^+$

Example 2

4-Fluoro-1-(2-fluoro-5-(5-(methylsulfonyl)pyridin-3-yl)phenyl)-1-(2-methylpyridin-4-yl)-1H-isoindol-3-amine

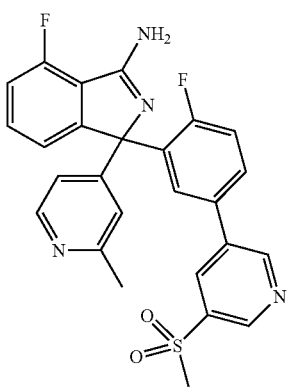

The title compound was synthesized as described for Example 1 in 32% yield, starting from 1-(5-bromo-2-fluorophenyl)-4-fluoro-1-(2-methylpyridin-4-yl)-1H-isoindol-3-amine (80 mg, 0.19 mmol) and 5-(methylsulfonyl)pyridin- 3-ylboronic acid (50.5 mg, 0.25 mmol). $^1$H NMR (500 MHz, DMSO-d$_6$, 298 K) δ ppm 9.07 (d, 1 H), 9.04 (d, 1 H), 8.39 (t, 1 H), 8.31 (d, 1 H), 7.84 (m, 1 H), 7.62-7.69 (m, 2 H), 7.56 (m, 1 H), 7.38 (dd, 1 H), 7.28-7.34 (m, 1 H), 7.04 (s, 1 H), 6.98 (dd, 1 H), 6.76 (br. s., 2 H), 3.37 (s, 3 H), 2.38 (s, 3 H); MS (ES+) m/z 491 (M+1).

The compound displays an IC$_{50}$ of 27000 nM in the FRET assay.

Example 3

5-(3-(3-Amino-4-fluoro-1-(2-methylpyridin-4-yl)-1H-isoindol-1-yl)-4-fluorophenyl)nicotinonitrile

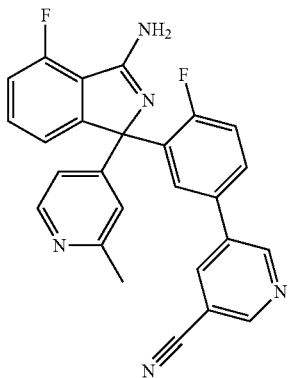

The title compound was synthesized as described for Example 1 in 38% yield, starting from 1-(5-bromo-2-fluorophenyl)-4-fluoro-1-(2-methylpyridin-4-yl)-1H-isoindol-3-amine (80 mg, 0.19 mmol) and 5-cyanopyridin-3-ylboronic acid (37.1 mg, 0.25 mmol).

$^1$H NMR (500 MHz, DMSO-d$_6$, 298 K) δ ppm 9.01 (dd, 2 H), 8.53 (t, 1 H), 8.31 (d, 1 H), 7.79 (m, 1 H), 7.60-7.66 (m, 2 H), 7.56 (m, 1 H), 7.27-7.39 (m, 2 H), 7.04 (s, 1 H), 6.98 (dd, 1 H), 6.74 (br. s., 2 H), 2.38 (s, 3 H); MS (ES+) m/z 438 (M+1)

Example 4

4-Fluoro-1-(2-fluoro-5-(5-fluoropyridin-3-yl)phenyl)-1-(2-methylpyridin-4-yl)-1H-isoindol-3-amine

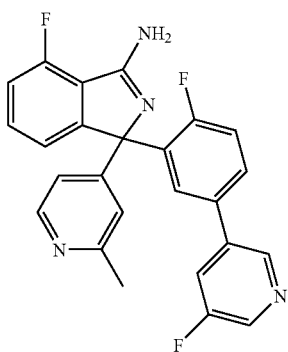

The title compound was synthesized as described for Example 1 in 41% yield, starting from 1-(5-bromo-2-fluorophenyl)-4-fluoro-1-(2-methylpyridin-4-yl)-1H-isoindol-3-amine (80 mg, 0.19 mmol) and 5-fluoropyridin-3-ylboronic acid (35.4 mg, 0.25 mmol).

$^1$H NMR (500 MHz, DMSO-d$_6$, 298 K) δ ppm 8.62 (t, 1 H), 8.57 (d, 1 H), 8.31 (d, 1 H), 7.93 (m, 1 H), 7.76 (m, 1 H), 7.64 (d, 1 H), 7.53-7.61 (m, 2 H), 7.27-7.36 (m, 2 H), 7.05 (s, 1 H), 6.99 (dd, 1 H), 6.74 (br. s., 2 H), 2.38 (s, 3 H); MS (ES) m/z 431 (M+1)

Example 5

4-Fluoro-1-(2-fluoro-5-(pyridin-3-yl)phenyl)-1-(2-methylpyridin-4-yl)-1H-isoindol-3-amine

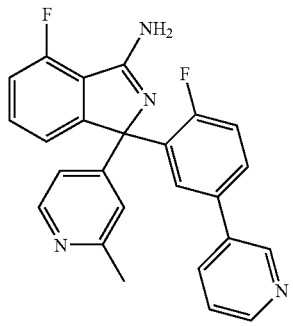

The title compound was synthesized as described for Example 1 in 37% yield, starting from 1-(5-bromo-2-fluorophenyl)-4-fluoro-1-(2-methylpyridin-4-yl)-1H-isoindol-3-amine (80 mg, 0.19 mmol) and pyridin-3-ylboronic acid (30.9 mg, 0.25 mmol).

$^1$H NMR (500 MHz, DMSO-d$_6$, 298 K) δ ppm 8.73 (d, 1 H), 8.55 (dd, 1 H), 8.31 (d, 1 H), 7.91 (dt, 1 H), 7.69-7.74 (m, 1 H), 7.60-7.65 (m, 1 H), 7.52-7.59 (m, 2 H), 7.46 (dd, 1 H), 7.27-7.35 (m, 2 H), 7.05 (s, 1 H), 6.99 (dd, 1 H), 6.74 (br. s., 2 H), 2.38 (s, 3 H); MS (ES+) m/z 413 (M+1).

Example 6

4-Fluoro-1-(2-fluoro-5-(pyrimidin-5-yl)phenyl)-1-(2-(trifluoromethyl)pyridin-4-yl)-1H-isoindol-3-amine

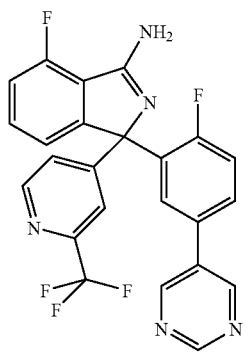

The title compound was synthesized as described for Example 1 in 58% yield, starting from 1-(5-bromo-2-fluorophenyl)-4-fluoro-1-(2-(trifluoromethyl)pyridin-4-yl)-1H-isoindol-3-amine (59.0 mg, 0.13 mmol), pyrimidin-5-ylboronic acid (17.17 mg, 0.14 mmol).

$^1$H NMR (500 MHz, DMSO-d$_6$) δ ppm 9.16 (s, 1 H) 8.99 (s, 2 H) 8.67 (d, 1 H) 7.87-7.78 (m, 1 H) 7.70 (d, 1 H)

7.67-7.63 (m, 1 H) 7.63-7.53 (m, 3 H) 7.42-7.29 (m, 2 H) 6.89 (br. s., 2 H), MS (ES+) m/z 469 [M+1]$^+$.

Example 7

5-(3-(3-Amino-4-fluoro-1-(2-(trifluoromethyl)pyridin-4-yl)-1H-isoindol-1-yl)-4-fluorophenyl)nicotinonitrile

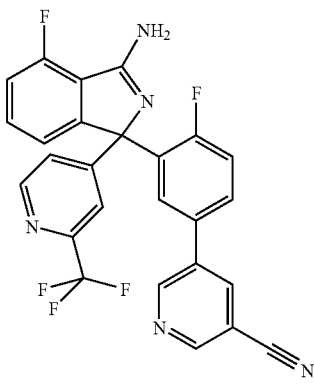

The title compound was synthesized as described for Example 1 in 65% yield, starting from 1-(5-bromo-2-fluorophenyl)-4-fluoro-1-(2-(trifluoromethyl)pyridin-4-yl)-1H-isoindol-3-amine (60.0 mg, 0.13 mmol) and 5-(4,4,5,5-tetramethyl-1,3,2-dioxaborolan-2-yl)nicotinonitrile (32.4 mg, 0.14 mmol).

$^1$H NMR (500 MHz, DMSO-d$_6$) δ ppm 9.03 (d, 1 H) 9.00 (d, 1 H) 8.67 (d, 1 H) 8.53 (t, 1 H) 7.86-7.78 (m, 1 H) 7.71 (d, 1 H) 7.66-7.55 (m, 4 H) 7.43-7.28 (m, 2 H) 6.89 (br. s., 2 H), MS (ES+) m/z 492 [M+H]$^+$

Example 8

4-Fluoro-1-(2-fluoro-5-(5-(methylsulfonyl)pyridin-3-yl)phenyl)-1-(2-(trifluoromethyl)pyridin-4-yl)-1H-isoindol-3-amine

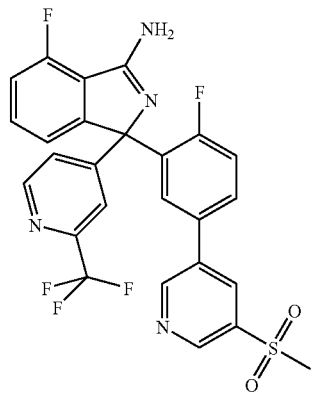

The title compound was synthesized as described for Example 1 in 58% yield, starting from 1-(5-bromo-2-fluorophenyl)-4-fluoro-1-(2-(trifluoromethyl)pyridin-4-yl)-1H-isoindol-3-amine (64.8 mg, 0.14 mmol) and 5-(methylsulfonyl)pyridin-3-ylboronic acid (30.6 mg, 0.15 mmol).

$^1$H NMR (500 MHz, DMSO-d$_6$) δ ppm 9.07 (d, 1 H) 9.03 (d, 1 H) 8.68 (d, 1 H) 8.40 (t, 1 H) 7.82-7.92 (m, 1 H) 7.71 (d, 1 H) 7.53-7.67 (m, 4 H) 7.40 (dd, 1 H) 7.30-7.37 (m, 1H) 6.91 (br. s., 2 H) 3.36 (s, 3 H), MS (ES+) m/z 545 [M+1]$^+$

Example 9

1-(3'-Chlorobiphenyl-3-yl)-4-fluoro-1-(pyridin-4-yl)-1H-isoindol-3-amine

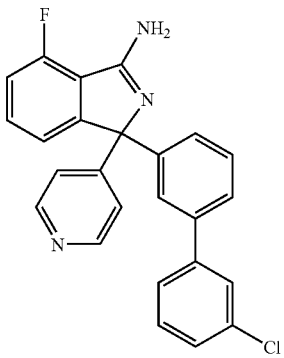

The title compound was synthesized as described for Example 1 in 38% yield, starting from 1-(3-bromophenyl)-4-fluoro-1-(pyridin-4-yl)-1H-isoindol-3-amine (80 mg, 0.21 mmol) and 3-chlorophenylboronic acid (39.3 mg, 0.25 mmol).

$^1$H NMR (500 MHz, DMSO-d$_6$) δ ppm 8.46 (d, J=6.15 Hz, 2 H) 7.71 (d, J=7.57 Hz, 1 H) 7.51-7.63 (m, 4 H) 7.45-7.51 (m, 2 H) 7.38-7.45 (m, 2 H) 7.32-7.38 (m, 1 H) 7.24-7.32 (m, 3 H) 6.69 (br. s., 2 H); MS (ES+) m/z 414 [M+1]$^+$.

Example 10

4-Fluoro-1-(pyridin-4-yl)-1-(3-(pyrimidin-5-yl)phenyl)-1H-isoindol-3-amine

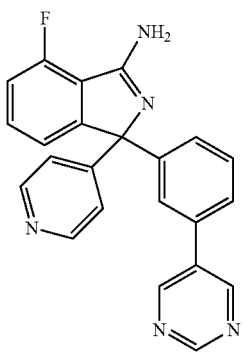

The title compound was synthesized as described for Example 1 in 47% yield, starting from 4-fluoro-1-(pyridin-4-yl)-1-(3-(pyrimidin-5-yl)phenyl)-1H-isoindol-3-amine and 5-pyrimidinylboronic acid (0.034 g, 0.28 mmol).

$^1$H NMR (DMSO-d$_6$) δ ppm 9.17 (s, 1 H) 9.01 (s, 2 H) 8.50-8.42 (m, 2 H) 7.80-7.74 (m, 1 H) 7.70-7.65 (m, 1 H)

7.65-7.63 (m, 1 H) 7.58-7.51 (m, 1 H) 7.50-7.44 (m, 2 H) 7.32-7.26 (m, 3 H) 6.66 (br. s., 2 H), MS (ES+) 382 [M+1]+.

Example 11

(R) and (S) 4-Fluoro-1-(pyridin-4-yl)-1-(3-(pyrimidin-5-yl)phenyl)-1H-isoindol-3-amine

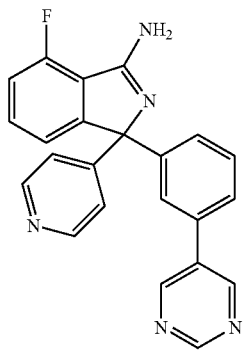

Chromatographic separation of the enantiomers of 4-fluoro-1-(pyridin-4-yl)-1-(3-(pyrimidin-5-yl)phenyl)-1H-isoindol-3-amine-4-fluoro-1-(pyridin-4-yl)-1-(3-(pyrimidin-5-yl)phenyl)-1H-isoindol-3-amine (1 g, 2.62 mmol) was dissolved in methanol (30 mL) and the resulting solution was injected (30 stacked injections) on a Chiralcel OD column (20×250 mm), using methanol/CO₂ (30:70) as eluent at a flow rate of 50 mL/min. Detection was monitored at 220 nm and the two isomers were collected and concentrated in vacuo. Isomer 1, 414 mg with unknown absolute configuration was collected:

¹H NMR (DMSO-d₆) δ ppm 9.18 (s, 1 H) 9.02 (s, 2 H) 8.50-8.42 (m, 2 H) 7.81-7.74 (m, 1 H) 7.71-7.66 (m, 1 H) 7.66-7.63 (m, 1 H) 7.58-7.51 (m, 1 H) 7.51-7.44 (m, 2 H) 7.33-7.24 (m, 3 H) 6.69 (br. s., 2 H), MS (ES+) 382 [M+H]+.

Isomer 2, 422 mg with unknown absolute configuration was collected:

¹H NMR (DMSO-d₆) δ ppm 9.18 (s, 1 H) 9.02 (s, 2 H) 8.52-8.42 (m, 2 H) 7.81-7.75 (m, 1 H) 7.71-7.66 (m, 1 H) 7.66-7.62 (m, 1 H) 7.58-7.51 (m, 1 H) 7.51-7.44 (m, 2 H) 7.33-7.24 (m, 3 H) 6.69 (br. s., 2 H), MS (ES+) 382 [M+H]+.

Example 12

4-Fluoro-1-(4-fluoro-3-(pyrimidin-5-yl)phenyl)-1-(2-(trifluoromethyl)pyridin-4-yl)-1H-isoindol-3-amine

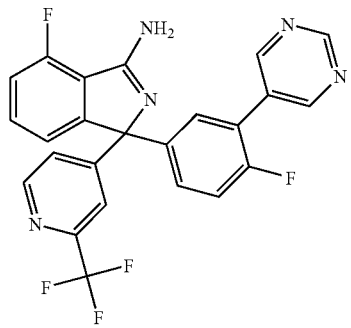

1-(3-Bromo-4-fluorophenyl)-4-fluoro-1-(2-(trifluoromethyl)pyridin-4-yl)-1H-isoindol-3-amine (0.30 g, 0.64 mmol) and 5-pyrimidinylboronic acid (0.104 g, 0.84 mmol) in DMF (5.00 mL) was heated to 90° C. under argon atmosphere. Dichloro[1,1'-bis(diphenylphosphino)ferrocene]palladium (II) dichloromethane adduct (0.039 g, 0.05 mmol) and aqueous potassium carbonate (2.00 M) (0.961 mL, 1.92 mmol) were added and the resulting mixture was stirred at 90° C. for 1 h. The reaction mixture was cooled to room temperature, and then filtered through a syringe filter and purified by preparative HPLC to give the title compound (0.158 g, 51% yield).

¹H NMR (500 MHz, DMSO-d₆) δ ppm 9.21 (s, 1 H) 8.95 (d, J=1.10 Hz, 2 H) 8.70 (d, J=5.20 Hz, 1 H) 7.86 (d, J=7.57 Hz, 1 H) 7.71 (s, 1 H) 7.68 (dd, J=5.20, 1.26 Hz, 1 H) 7.55-7.63 (m, 2 H) 7.51 (ddd, J=8.63, 4.93, 2.52 Hz, 1 H) 7.27-7.41 (m, 2 H) 6.83 (br. s., 2 H) 1.90 (s, 0.68 H); MS (ES+) m/z 468 [M+H]+.

Example 13

(R) and (S) 4-Fluoro-1-(4-fluoro-3-(pyrimidin-5-yl)phenyl)-1-(2-(trifluoromethyl)pyridin-4-yl)-1H-isoindol-3-amine

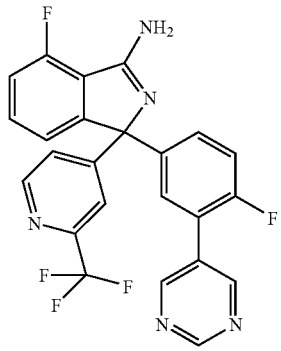

4-Fluoro-1-(4-fluoro-3-(pyrimidin-5-yl)phenyl)-1-(2-(trifluoromethyl)pyridin-4-yl)-1H-isoindol-3-amine (0.502 g, 1.07 mmol) was dissolved in methanol (20 mL) and the resulting solution was injected (20 stacked injections) on a Chiralcel AD column (20×250 mm), using isopropanol(diethylamine)/CO₂ (20:80) as eluent at a flow rate of 50 mL/min. Detection was monitored at 220 nm and the two isomers were collected and concentrated to in vacuo.

Isomer 1, with unknown absolute configuration was collected: (0.209 g, 42% yield).

¹H NMR (500 MHz, DMSO-d₆) δ ppm 9.21 (s, 1 H) 8.95 (d, 2 H) 8.70 (d, 1 H) 7.86 (d, 1 H) 7.69-7.73 (m, 1 H) 7.68 (m, 1 H) 7.55-7.62 (m, 2 H) 7.37 (dd, 1 H) 7.27-7.34 (m, 1H) 6.82 (br. s., 2 H); MS (ES+) m/z 468 (M+1)+

Isomer 2, with unknown absolute configuration was collected (0.204 g, 41% yield).

¹H NMR (500 MHz, DMSO-d₆) δ ppm 9.21 (s, 1 H) 8.95 (dd, 2 H) 8.70 (d, 1 H) 7.86 (d, 1 H) 7.71 (s, 1 H) 7.68 (d, 1 H)

7.55-7.62 (m, 2 H) 7.48-7.54 (m, 1 H) 7.37 (t, 1 H) 7.32 (t, 1 H) 6.83 (br. s, 1 H); MS (ES+) m/z 468 (M+H)+

Example 14

4-Fluoro-1-(2'-fluoro-3'-methoxybiphenyl-3-yl)-1-(pyridin-4-yl)-1H-isoindol-3-amine

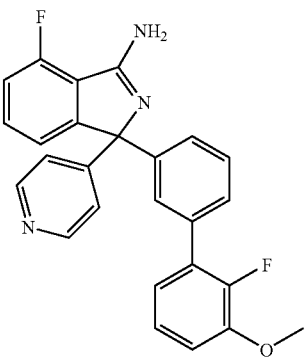

The title compound was synthesized as described for Example 1 in 28% yield, starting from 1-(3-bromophenyl)-4-fluoro-1-(pyridin-4-yl)-1H-isoindol-3-amine (0.096 g, 0.25 mmol) and 2-fluoro-3-methoxybenzeneboronic acid (0.047 g, 0.28 mmol): $^1$H NMR (DMSO-$d_6$) δ ppm 8.50-8.44 (m, 2 H) 7.65-7.60 (m, 1 H) 7.58-7.49 (m, 1 H) 7.45-7.37 (m, 3 H) 7.36-7.24 (m, 4 H) 7.22-7.11 (m, 2 H) 6.96-6.90 (m, 1 H) 6.64 (br. s, 2H) 3.85 (s, 3 H), MS (ES+) m/z 428 [M+1]+.

Example 15

4-Fluoro-1-(3-(5-fluoropyridin-3-yl)phenyl)-1-(pyridin-4-yl)-1H-isoindol-3-amine

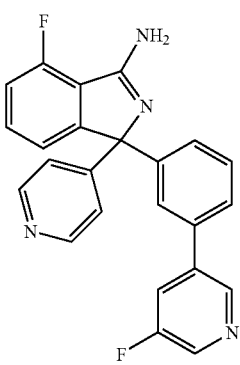

The title compound was synthesized as described for Example 1 in 25% yield, starting from 1-(3-bromophenyl)-4-fluoro-1-(pyridin-4-yl)-1H-isoindol-3-amine (0.096 g, 0.25 mmol) and 3-fluoro-5-(4,4,5,5-tetramethyl-1,3,2-dioxaborolan-2-yl)pyridine (0.061 g, 0.28 mmol):

$^1$H NMR (DMSO-$d_6$) δ ppm 8.46-8.40 (m, 1 H) 8.37-8.31 (m, 1 H) 8.28-8.19 (m, 2 H) 7.77-7.68 (m, 1 H) 7.56-7.50 (m, 1 H) 7.47-7.37 (m, 2 H) 7.36-7.28 (m, 1 H) 7.28-7.19 (m, 2 H) 7.12-6.99 (m, 3 H) 6.44 (br. s., 2 H), MS (ES−) m/z 397 [M−H]−.

Example 16

4-Fluoro-1-(4-fluoro-3-(pyrimidin-5-yl)phenyl)-1-(pyridin-4-yl)-1H-isoindol-3-amine

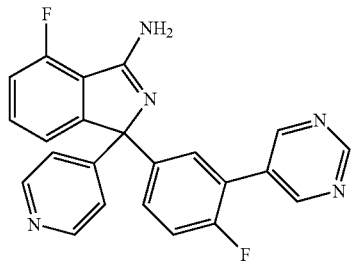

The title compound was synthesized as described for Example 12 in 29% yield, starting from 1-(3-bromo-4-fluorophenyl)-4-fluoro-1-(pyridin-4-yl)-1H-isoindol-3-amine (44 mg, 0.11 mmol) and 5-pyrimidinylboronic acid (18.66 mg, 0.15 mmol).

$^1$H NMR (600 MHz, DMSO-$d_6$) δ ppm 9.21 (s, 1 H) 8.94 (d, J=1.21 Hz, 2 H) 8.47 (dd, J=4.55, 1.64 Hz, 2 H) 7.76 (d, J=7.54 Hz, 1 H) 7.48-7.57 (m, 3 H) 7.35 (dd, J=10.07, 8.79 Hz, 1 H) 7.25-7.31 (m, 3 H) 1.91 (s, 1.5 H); MS (ES+) m/z 400 [M+H]+.

Example 17

4-Fluoro-1-(4-methoxyphenyl)-1-(3-(pyrimidin-5-yl)phenyl)-1H-isoindol-3-amine

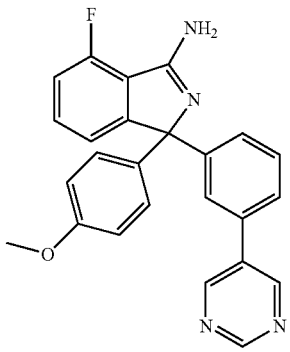

The title compound was synthesized as described for Example 1 in 59% yield, starting from 1-(3-bromophenyl)-4-fluoro-1-(4-methoxyphenyl)-1H-isoindol-3-amine (0.13 g, 0.25 mmol) and 5-pyrimidinylboronic acid (0.037 g, 0.30 mmol):

$^1$H NMR (DMSO-$d_6$) δ ppm 9.17 (s, 1 H) 8.99 (s, 2 H) 7.69-7.58 (m, 3 H) 7.53-7.46 (m, 1 H) 7.46-7.42 (m, 2 H)

7.26-7.17 (m, 3 H) 6.85-6.78 (m, 2 H) 6.50 (br. s., 2 H) 3.69 (s, 3 H), MS (ES−) m/z 409 [M−H]⁻.

Example 18

1-(2',6-Difluoro-3'-methoxybiphenyl-3-yl)-4-fluoro-1-(pyrimidin-5-yl)-1H-isoindol-3-amine

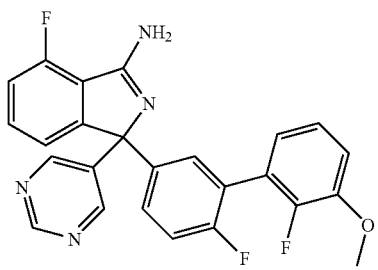

The title compound was synthesized as described for Example 12 in 18% yield, starting from 1-(3-bromo-4-fluorophenyl)-4-fluoro-1-(pyrimidin-5-yl)-1H-isoindol-3-amine (59.6 mg, 0.15 mmol) and 2-fluoro-3-methoxybenzeneboronic acid (59.5 mg, 0.35 mmol); $^1$H NMR (500 MHz, DMSO-d$_6$)$_6$ ppm 9.08 (s, 1 H) 8.74 (s, 2 H) 7.81 (d, 1 H) 7.53-7.60 (m, 1 H) 7.42-7.49 (m, 1 H) 7.37 (dd, 1 H) 7.25-7.33 (m, 2 H) 7.18-7.25 (m, 2 H) 6.87-6.93 (m, 1 H) 6.77 (br. s., 2 H) 3.85 (s, 3 H). MS (ES−) m/z 445 [M−H]⁻

Example 19

4-Fluoro-1-(4-fluoro-3-(4-methoxypyridin-2-yl)phenyl)-1-(pyrimidin-5-yl)-1H-isoindol-3-amine

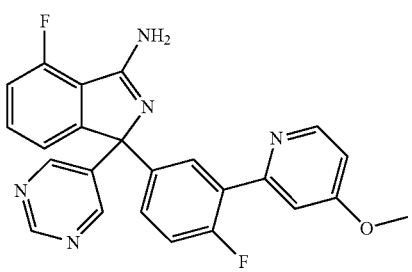

4-Methoxy-2-(tributylstannyl)pyridine (265 mg, 0.67 mmol), 1-(3-bromo-4-fluorophenyl)-4-fluoro-1-(pyrimidin-5-yl)-1H-isoindol-3-amine (178.3 mg, 0.44 mmol) and tetrakis(triphenylphosphine)palladium(0) (138 mg, 0.11 mmol) were mixed in dry DMF (2.00 mL) and heated in a microwave reactor at 110° C. for 305 min. The resulting product mixture was filtered and purified by preparative-HPLC to give the title compound (28.2 mg, 12% yield):

$^1$H NMR (500 MHz, DMSO-d$_6$) δ ppm 9.09 (s, 1 H) 8.74 (s, 2 H) 8.48 (d, 1 H) 7.89 (dd, 2.44 Hz, 1 H) 7.75 (d, Hz, 1 H) 7.57 (td, 4.81 Hz, 1 H) 7.41 (m 1 H) 7.24-7.34 (m, 3 H) 6.99 (dd, 2.44 Hz, 1 H) 6.78 (br. s., 1 H) 3.85 (s, 3 H) 1.90 (s, 4 H), MS (ES+) m/z 430 [M+H]⁺.

Example 20

4-Fluoro-1-(3-(pyrimidin-5-yl)phenyl)-1-(2-(trifluoromethyl)pyridin-4-yl)-1H-isoindol-3-amine

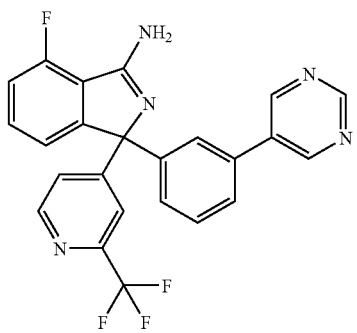

The title compound was synthesized as described for Example 12 in 46% yield starting from 1-(3-bromophenyl)-4-fluoro-1-(2-(trifluoromethyl)pyridin-4-yl)-1H-isoindol-3-amine (56.2 mg, 0.12 mmol), pyrimidin-5-ylboronic acid (17.0 mg, 0.14 mmol), PdCl$_2$(dppf)-CH$_2$Cl$_2$ adduct (10.2 mg, 0.01 mmol), K$_2$CO$_3$ (aq) (0.19 mL, 0.37 mmol).

$^1$H NMR (400 MHz, CDCl$_3$) δ ppm 9.20 (s, 1H), 8.88 (s, 2H), 8.66 (d, 1H), 7.67 (s, 1H), 7.58-7.47 (m, 5H), 7.42-7.33 (m, 2H), 7.18 (t, 1H), 6.03 (br s, 2H); MS (ES+) m/z 450 [M+1]⁺.

Example 21

1-(2,6-Dimethylpyridin-4-yl)-4-fluoro-1-(3-(pyrimidin-5-yl)phenyl)-1H-isoindol-3-amine

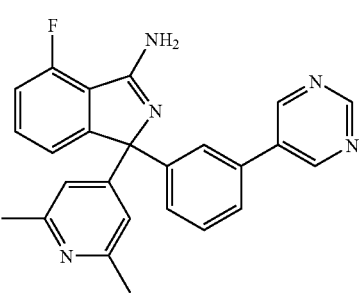

The title compound was synthesized as described for Example 12 in 50% yield starting from 1-(3-bromophenyl)-1-(2,6-dimethylpyridin-4-yl)-4-fluoro-1H-isoindol-3-amine (70.2 mg, 0.17 mmol), pyrimidin-5-ylboronic acid (23.3 mg, 0.19 mmol), PdCl$_2$(dppf)-CH$_2$Cl$_2$ adduct (14.0 mg, 0.02 mmol), and K$_2$CO$_3$ (aq) (0.26 mL, 0.51 mmol).

¹H NMR (400 MHz, CDCl₃) δ ppm 9.17 (s, 1H), 8.87 (s, 2H), 7.51-7.42 (m, 4H), 7.39-7.34 (m, 2H), 7.11 (t, 1H), 6.89 (s, 2H), 5.54 (br s, 2H), 2.46 (s, 6H); MS (ES+) m/z 410 [M+1]⁺.

Example 22

5-(3-(3-Amino-1-(2,6-dimethylpyridin-4-yl)-4-fluoro-1H-isoindol-1 yl)phenyl)nicotinonitrile

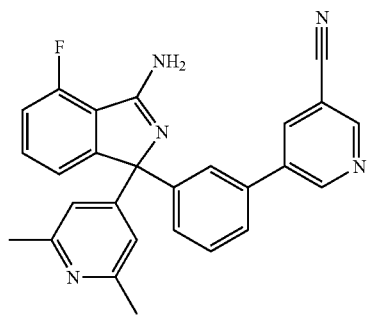

The title compound was synthesized as described for Example 12 in 53% yield starting from 1-(3-bromophenyl)-1-(2,6-dimethylpyridin-4-yl)-4-fluoro-1H-isoindol-3-amine (104.8 mg, 0.26 mmol), 5-cyanopyridin-3-ylboronic acid (37.8 mg, 0.26 mmol), PdCl₂(dppf)-CH₂Cl₂ adduct (20.9 mg, 0.03 mmol), and K₂CO₃ (aq) (0.38 mL, 0.77 mmol).

¹H NMR (400 MHz, CDCl₃) δ ppm 8.95 (d, 1H), 8.83 (d, 1H), 8.06 (t, 1H), 7.52-7.43 (m, 4H), 7.41-7.35 (m, 2H), 7.13 (t, 1H), 6.89 (s, 2H), 5.30 (br s, 2H), 2.46 (s, 6H); MS (ES+) m/z 434 [M+1]⁺.

Example 23

5-(3-(3-Amino-4-fluoro-1-(2-(trifluoromethyl)pyridin-4-yl)-1H-isoindol-1-yl) phenyl)nicotinonitrile

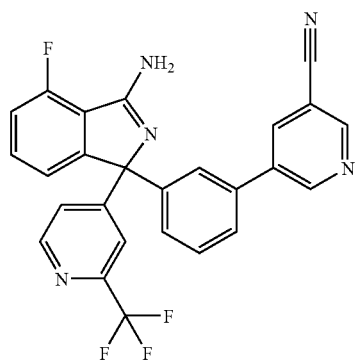

The title compound was synthesized as described for Example 12 in 38% yield starting from 1-(3-bromophenyl)-4-fluoro-1-(2-(trifluoromethyl)pyridin-4-yl)-1H-isoindol-3-amine (24.2 mg, 0.05 mmol), 5-cyanopyridin-3-ylboronic acid (8.0 mg, 0.05 mmol), PdCl₂(dppf)-CH₂Cl₂ adduct (4.4 mg, 0.005 mmol), and K₂CO₃ (aq) (0.08 mL, 0.16 mmol).

¹H NMR (400 MHz, CDCl₃) δ ppm 8.73 (d, 1H), 8.63 (d, 1H), 8.44 (d, 1H), 7.86 (t, 1H), 7.43 (s, 1H), 7.36-7.24 (m, 5H), 7.18-7.12 (m, 2H), 6.97 (t, 1H), 5.45 (br s, 2H); MS (ES+) m/z 474 [M+1]⁺.

Example 24

4-Fluoro-1-(4-fluoro-3-(pyrimidin-5-yl)phenyl)-1-(2-methoxypyridin-4-yl)-1H-isoindol-3-amine

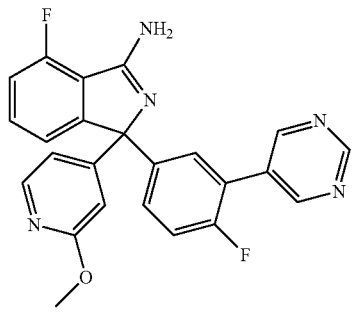

1-(3-Bromo-4-fluorophenyl)-4-fluoro-1-(2-methoxypyridin-4-yl)-1H-isoindol-3-amine (98.9 mg, 0.23 mmol), 5-pyrimidinylboronic acid (31.3 mg, 0.25 mmol), 1,1'-bis (diphenylphosphino)ferrocene-palladium(II)dichloride dichloromethane complex (9.39 mg, 0.01 mmol), 2 M aqueous potassium carbonate (0.345 mL, 0.69 mmol) and DMF (2.0 mL) were put in a microwave vial and irradiated in a microwave oven at 110° C. for 20 min. Additional 5-pyrimidinylboronic acid (18.51 mg, 0.15 mmol) and [1,1'-bis (diphenylphosphino)ferrocene]palladium(II) chloride (9.39 mg, 0.01 mmol) were added and the resulting mixture was irradiated at 110° C. for 40 min. The resulting product mixture was filtered and purified by preparative-HPLC to give the title compound (38.9 mg, 39.4% yield).

¹H NMR (500 MHz, DMSO-d₆) δ ppm 9.21 (s, 1 H) 8.94 (d, 2 H) 8.05 (d, 1 H) 7.77 (d, 1 H) 7.48-7.57 (m, 3 H) 7.34 (dd, 1 H) 7.24-7.31 (m, 1 H) 6.91 (dd, 1 H) 6.65 (d, 1 H) 3.78 (s, 3 H) 1.91 (s, 2 H); MS (ES+) m/z 430 [M+H]⁺

Example 25

5-(5-(3-Amino-4-fluoro-1-(2-(trifluoromethyl)pyridin-4-yl)-1H-isoindol-1-yl)-2-fluorophenyl) nicotinonitrile trifluoroacetate

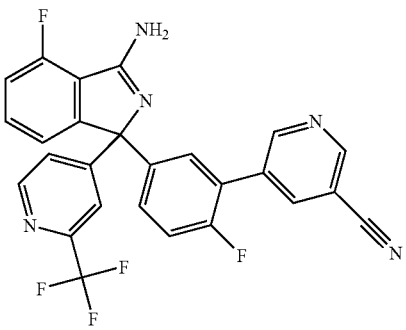

3-Cyanopyridine-5-boronic acid pinacol ester (85 mg, 0.37 mmol), 1-(3-bromo-4-fluorophenyl)-4-fluoro-1-(2-(trifluoromethyl)pyridin-4-yl)-1H-isoindol-3-amine (115.5 mg, 0.25 mmol), [1,1'-bis(diphenylphosphino)ferrocene]palladium(II) chloride (10.07 mg, 0.01 mmol), 2 M aqueous potassium carbonate (0.370 mL, 0.74 mmol) and DMF (2.00 mL) were put in a microwave vial and irradiated in a microwave oven at 110° C. for 20 min. Additional 3-cyanopyridine-5-boronic acid pinacol ester (36.9 mg, 0.16 mmol) and [1,1'-bis (diphenylphosphino)ferrocene]palladium(II) chloride (10.07 mg, 0.01 mmol) were added and the resulting mixture was irradiated at 110° C. for 20 min. Additional 3-cyanopyridine-5-boronic acid pinacol ester (36.9 mg, 0.16 mmol) and [1,1'-bis (diphenylphosphino)ferrocene]palladium(II) chloride (10.07 mg, 0.01 mmol) were added and the resulting mixture was irradiated at 110° C. for 30 min. Additional 3-cyanopyridine-5-boronic acid pinacol ester (36.9 mg, 0.16 mmol) and [1,1'-bis (diphenylphosphino)ferrocene]palladium(II) chloride (10.07 mg, 0.01 mmol) were added and the resulting mixture was irradiated for 30 min. The resulting product mixture was filtered and purified by preparative-HPLC to give the title compound 11.4 mg, (7.6% yield).

$^1$H NMR (500 MHz, DMSO-d$_6$) δ ppm 11.78 (br. s., 1 H) 10.11 (br. s., 1 H) 9.56 (br. s., 1 H) 9.08 (dd, J=1.73, 0.31 Hz, 1 H) 9.02 (t, J=1.89 Hz, 1 H) 8.77-8.89 (m, 1 H) 8.47-8.54 (m, 1 H) 7.95 (br. s., 1 H) 7.79-7.89 (m, 2 H) 7.70 (ddd (m), 1 H) 7.56-7.66 (m, 2 H) 7.41-7.55 (m, 2 H); MS (ES−) m/z 490 [M+H]$^-$.

Example 26

5-(5-(3-Amino-4-fluoro-1-(pyridin-4-yl)-1H-isoindol-1-yl)-2-fluorophenyl) nicotinonitrile

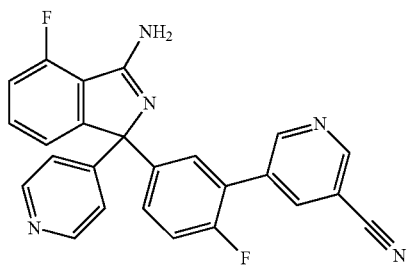

3-Cyanopyridine-5-boronic acid pinacol ester (58.1 mg, 0.25 mmol), 1-(3-bromo-4-fluorophenyl)-4-fluoro-1-(pyridin-4-yl)-1H-isoindol-3-amine (67.4 mg, 0.17 mmol), [1,1'-bis (diphenylphosphino)ferrocene]palladium(II) chloride (6.88 mg, 8.42 µmol), 2 M aqueous potassium carbonate (0.253 mL, 0.51 mmol) and DMF (2.00 mL) were put in a microwave vial and irradiated in a microwave oven at 110° C. for 20 min. Additional 3-cyanopyridine-5-boronic acid pinacol ester (25.2 mg, 0.11 mmol) and [1,1'-bis (diphenylphosphino)ferrocene]palladium(II) chloride (6.88 mg, 8.42 µmol) were added and the resulting mixture was irradiated at 110° C. for 30 min. Additional 3-cyanopyridine-5-boronic acid pinacol ester (25.2 mg, 0.11 mmol) and [1,1'-bis (diphenylphosphino)ferrocene]palladium(II) chloride (6.88 mg, 8.42 µmol) were added and the resulting mixture was irradiated at 110° C. for 30 min. The product was purified by preparative HPLC. The desired fractions were pooled and concentrated in vacuo. The residue was partitioned between water and ethyl acetate (×3). The organic layer was collected, dried (Na$_2$SO$_4$), filtered and concentrated in vacuo. The residue was redissolved in methanol and concentrated in vacuo three times to give the title compound 5.80 mg, (7.4% yield).

$^1$H NMR (500 MHz, DMSO-d$_6$) δ ppm 9.05 (d, 1 H) 8.93-8.99 (m, 1 H) 8.40-8.56 (m, 3 H) 7.78 (d, 1 H) 7.46-7.63 (m, 3 H) 7.36 (t, 1 H) 7.28 (d, 3 H) 6.70 (br. s., 1 H) 1.91 (s, 2 H); MS (ES+) m/z 424 [M+H]$^+$.

Example 27

4-Fluoro-1-(2-methoxypyridin-4-yl)-1-(3-(pyrimidin-5-yl)phenyl)-1H-isoindol-3-amine

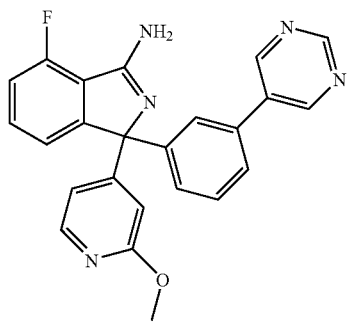

1-(3-Bromophenyl)-4-fluoro-1-(2-methoxypyridin-4-yl)-1H-isoindol-3-amine (100 mg, 0.24 mmol), 5-pyrimidinylboronic acid (31.6 mg, 0.25 mmol), [1,1'-bis (diphenylphosphino)ferrocene]palladium(II) chloride (9.90 mg, 0.01 mmol), cesium carbonate (0.058 mL, 0.73 mmol) and DME:EtOH:water (6:3:1) (3.00 mL) were mixed in a microwave vial and heated in a microwave reactor at 150° C. for 20 min. The resulting product mixture was filtered and purified by preparative-HPLC to give 58 mg (54% yield of the title compound (after pooling and freeze drying of the fractions).

$^1$H NMR (400 MHz, DMSO-d$_6$) δ ppm 9.17 (s, 1 H) 9.02 (s, 2 H) 8.04 (d, 1 H) 7.77 (d, 1 H) 7.68 (dd, 1 H) 7.64 (s, 1 H) 7.55 (td (m), 1 H) 7.47 (d, 2 H) 7.28 (t, 1 H) 6.91 (dd, 1 H) 6.66 (s, 1 H) 3.79 (s, 3 H) 1.91 (s, 2 H); MS (ES+) m/z 412 [M+H]$^+$.

Example 28

5-(3-(3-Amino-4-fluoro-1-(2-methoxypyridin-4-yl)-1H-isoindol-1-yl) phenyl)nicotinonitrile acetate

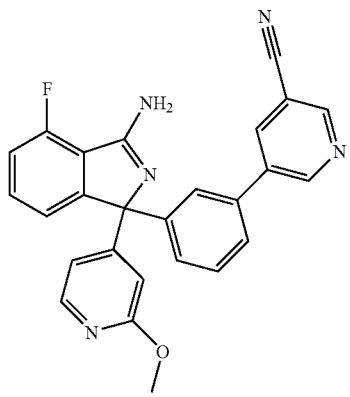

The title compound was synthesized as described for example 27 in 52% yield, starting from 1-(3-bromophenyl)-4-fluoro-1-(2-methoxypyridin-4-yl)-1H-isoindol-3-amine (100 mg, 0.24 mmol) and 3-cyanopyridine-5-boronic acid pinacol ester (58.6 mg, 0.25 mmol). $^1$H NMR (400 MHz, DMSO-$d_6$) δ ppm 9.06 (d, 1 H) 9.00 (d, 1 H) 8.56 (s, 1 H) 8.04 (d, 1 H) 7.79 (d, 1 H) 7.63-7.73 (m, 2 H) 7.51-7.60 (m, 1 H) 7.41-7.51 (m, 2 H) 7.28 (t, 1 H) 6.90 (d, 1 H) 6.64 (s, 1 H) 3.78 (s, 3 H) 1.89 (s, 3 H); MS (ES+) m/z 436 [M+H]$^+$.

Example 29

4-Fluoro-1-(2-methoxypyridin-4-yl)-1-(3-(pyrazin-2-yl)phenyl)-1H-isoindol-3-amine acetate

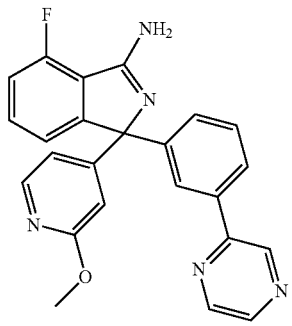

1-(3-Bromophenyl)-4-fluoro-1-(2-methoxypyridin-4-yl)-1H-isoindol-3-amine (0.150 g, 0.36 mmol), 2-(tributylstannyl)pyrazine (0.120 mL, 0.38 mmol), tetrakis(triphenylphosphine)palladium(0) (0.042 g, 0.04 mmol) and DMF (4 mL) were put in microwave vial and irradiated in a microwave reactor at 150° C. for 20 min. The resulting product mixture was filtered and purified by preparative-HPLC to give the title compound 0.083 g, (48.5% yield).

$^1$H NMR (500 MHz, DMSO-$d_6$) δ ppm 9.17 (d, 1 H), 8.68 (dd, 1 H), 8.60 (d, 1 H), 8.07-8.11 (m, 1 H), 8.05 (d, 1 H), 7.97-8.02 (m, 1 H), 7.65 (d, 1 H), 7.54 (td (m), 1 H) 7.41-7.49 (m, 2 H), 7.25-7.32 (m, 1 H), 6.91 (dd, 1.50 Hz, 1 H), 6.65 (d, 1 H), 3.79 (s, 3 H) 1.89 (s, 3 H); MS (ES+) m/z 412 [M+H]$^+$.

Example 30

4-Fluoro-1-(3-(pyrazin-2-yl)phenyl)-1-(2-(trifluoromethyl)pyridin-4-yl)-1H-isoindol-3-amine

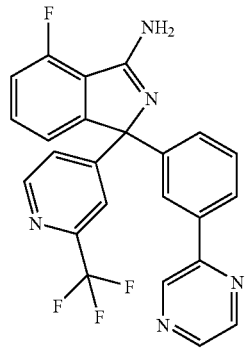

1-(3-Bromophenyl)-4-fluoro-1-(2-(trifluoromethyl)pyridin-4-yl)-1H-isoindol-3-amine (131 mg, 0.29 mmol), 2-(tributylstannyl)pyrazine (0.096 mL, 0.31 mmol) and Pd(Ph$_3$P)$_4$ (33.6 mg, 0.03 mmol) were dissolved in DMF (2 mL) and the reaction mixture was heated in a microwave reactor at 180° C. for 15 min. Brine was added and the mixture was extracted with EtOAc (3×). The combined organic phases were dried (Na$_2$SO$_4$), filtered and concentrated in vacuo. Purification by preperative HPLC afforded the title compound 18 mg (14% yield).

$^1$H NMR (400 MHz, CDCl$_3$) δ ppm 8.96 (s, 1H), 8.66 (d, 1H), 8.63-8.58 (m, 1H), 8.50 (d, 1H), 7.99-7.91 (m, 2H), 7.64 (s, 1H), 7.61-7.53 (m, 1H), 7.52-7.45 (m, 2H), 7.43-7.34 (m, 2H), 7.18 (t, 1H); MS (ES+) m/z 450 [M+1]$^+$.

Example 31

1-(2-Cyclopropylpyridin-4-yl)-4-fluoro-1-(3-(pyrimidin-5-yl)phenyl)-1H-isoindol-3-amine

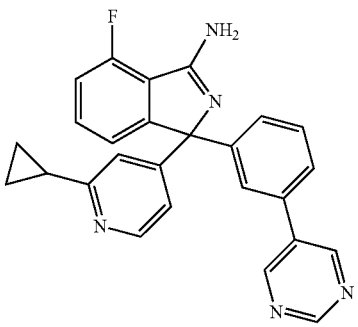

To a solution of 1-(3-bromophenyl)-1-(2-cyclopropylpyridin-4-yl)-4-fluoro-1H-isoindol-3-amine (97 mg, 0.23 mmol) in DME:EtOH:water (6:3:1) (5 mL) was added pyrimidin-5-ylboronic acid (37.0 mg, 0.30 mmol), dichloro[1,1'-bis(diphenylphosphino)ferrocene]-palladium (II) dichloromethane adduct (9.38 mg, 0.01 mmol) and cesium carbonate (225 mg, 0.69 mmol). The vial was sealed and heated in a microwave reactor at 150° C. for 20 minutes. The reaction was diluted with EtOAc and brine, the layers were separated and the aqueous layer was extracted with EtOAc. The organics were combined, dried (Na$_2$SO$_4$), filtered and the solvent was removed under reduced pressure. The crude was purified by preparative HPLC, appropriate fractions combined and the MeOH removed by evaporation. The remaining aqueous phase was basified by addition of sat. aqueous NaHCO$_3$ (pH~9) and extracted with dichloromethane (×3). The organics were combined, washed once with sat. aqueous NaHCO$_3$, dried (Na$_2$SO$_4$), filtered and evaporated to give 60 mg (62%) of the title compound.

$^1$H NMR (600 MHz, DMSO-$d_6$) δ ppm 9.16 (s, 1 H) 9.01 (s, 2 H) 8.26 (d, 1 H) 7.78 (d, 1 H) 7.64-7.70 (m, 1 H) 7.63 (s, 1 H) 7.53 (td, 1 H) 7.43-7.49 (m, 2 H) 7.26 (t, 1 H) 7.21 (d, 1 H) 7.03 (dd, 1 H) 6.62 (br. s., 2 H) 1.94-2.03 (m, 1 H) 0.78-0.90 (m, 4 H); MS (ES+) m/z 422 [M+H]$^+$

Example 32

1-(2-(Difluoromethyl)-6-methylpyridin-4-yl)-4-fluoro-1-(3-(pyrimidin-5-yl)phenyl)-1H-isoindol-3-amine

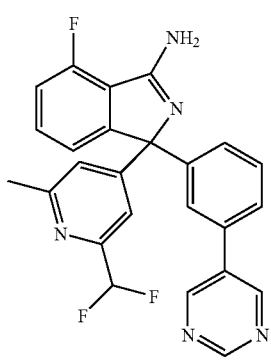

1-(3-Bromophenyl)-1-(2-(difluoromethyl)-6-methylpyridin-4-yl)-4-fluoro-1H-isoindol-3-amine (40 mg, 0.09 mmol), pyrimidin-5-ylboronic acid (12.22 mg, 0.10 mmol) and (1,1'-bis (diphenylphosphino)ferrocene)-dichloropalladium(II) (7.37 mg, 8.96 µmol) were mixed in THF (3 mL). Aqueous sodium carbonate (2M) (0.134 mL, 0.27 mmol) was added and the mixture was heated in a microwave reactor for 40 min at 140° C. The mixture was filtered through a pad of Celite®, eluated with DCM (15 mL) and concentrated in vacuo. Purification by preparative HPLC afforded 11.0 mg (27%) of the title compound.
$^1$H NMR (400 MHz, CDCl$_3$) δ ppm 9.20 (s, 1 H) 8.89 (s, 2 H) 7.44-7.58 (m, 4 H) 7.31-7.41 (m, 3 H) 7.26 (s, 1 H) 7.17 (t, 1 H) 6.72-6.43 (t, 1 H) 2.55 (s, 3 H); MS (ES+) m/z 446 [M+1]$^+$.

Example 33

1-(2-(Difluoromethyl)-6-methylpyridin-4-yl)-4-fluoro-1-(2-(pyrimidin-5-yl)pyridin-4-yl)-1H-isoindol-3-amine

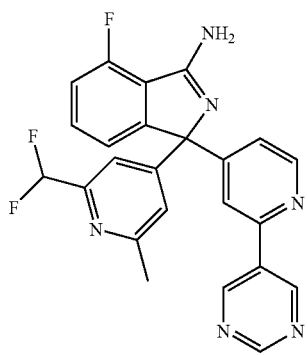

1-(2-Chloropyridin-4-yl)-1-(2-(difluoromethyl)-6-methylpyridin-4-yl)-4-fluoro-1H-isoindol-3-amine (400 mg, 0.99 mmol), pyrimidin-5-ylboronic acid (135 mg, 1.09 mmol) and (1,1'-bis(diphenylphosphino)ferrocene)-dichloropalladium (II) (82 mg, 0.10 mmol) were mixed in THF (3 mL). Aqueous sodium carbonate (2M) (1.490 mL, 2.98 mmol) was added and the mixture was heated in a microwave reactor for 40 min at 140° C. The mixture was filtered through a pad of Celite®, eluated with DCM (15 mL) and concentrated in vacuo. Purification by preparative HPLC afforded 60 mg (14%) of the title compound. $^1$H NMR (400 MHz, CDCl$_3$) δ ppm 9.26 (s, 2 H) 9.25 (s, 1 H) 8.69 (d, 1 H) 7.68 (s, 1 H) 7.50-7.58 (m, 1 H) 7.39 (d, 1 H) 7.35 (s, 1 H) 7.25 (dd, 1 H) 7.22 (s, 1 H) 7.19 (d, 1 H) 6.75-6.42 (t, 1 H) 2.56 (s, 3 H); MS (ES+) m/z 447 [M+1]$^+$.

Example 34

4-Fluoro-1-(3-fluoro-4-methoxy-5-methylphenyl)-1-(2-(pyrimidin-5-yl)pyridin-4-yl)-1H-isoindol-3-amine

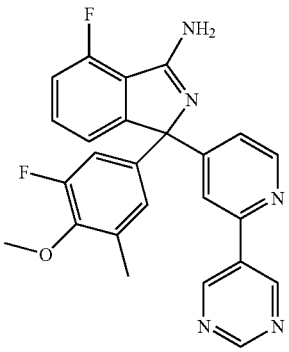

The title compound was synthesized as described in Example 33 in 11% yield starting from 1-(2-bromopyridin-4-yl)-4-fluoro-1-(3-fluoro-4-methoxy-5-methylphenyl)-1H-isoindol-3-amine (330 mg, 0.74 mmol) and pyrimidin-5-ylboronic acid (101 mg, 0.82 mmol).
$^1$H NMR (400 MHz, CDCl$_3$) δ ppm 9.26 (s, 2 H) 9.23 (s, 1 H) 8.65 (d, 1 H) 7.72 (s, 1 H) 7.49 (td, 1 H) 7.36 (d, 1 H) 7.30 (dd, 1 H) 7.14 (t, 1 H) 6.78-6.90 (m, 2 H) 3.88 (d, 3 H) 2.21 (s, 3 H); MS (ES+) m/z 444 [M+1]$^+$.

Example 35

4-Fluoro-1-(4-methoxy-3,5-dimethylphenyl)-1-(2-(pyrimidin-5-yl)pyridin-4-yl)-1H-isoindol-3-amine

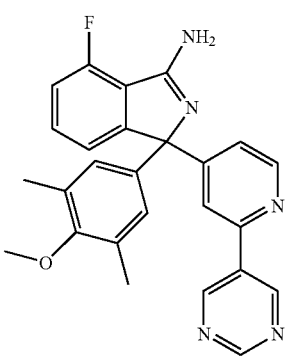

The title compound was synthesized as described in Example 33 in 5% yield starting from 1-(2-Bromopyridin-4- yl)-4-fluoro-1-(4-methoxy-3,5-dimethylphenyl)-1H-isoindol-3-amine (400 mg, 0.91 mmol) and pyrimidin-5-ylboronic acid (124 mg, 1.00 mmol).

$^1$H NMR (400 MHz, CDCl$_3$) δ ppm 9.27 (s, 2 H) 9.23 (s, 1 H) 8.65 (d, 1 H) 7.75 (s, 1 H) 7.50 (dd, 1 H) 7.38 (d, 1 H) 7.31 (dd, 1 H) 7.14 (t, 1 H) 6.88 (s, 2 H) 3.70 (s, 3 H) 2.22 (s, 6 H); MS (ES+) m/z 440 [M+1]$^+$.

Example 36

4-Fluoro-1-(5-methoxy-4,6-dimethylpyridin-2-yl)-1-(2-(pyrimidin-5-yl)pyridin-4-yl)-1H-isoindol-3-amine

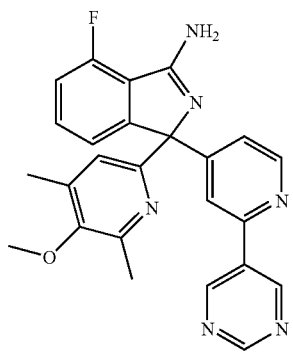

The title compound was synthesized as described in Example 33 in 7% yield starting from 1-(2-Bromopyridin-4-yl)-4-fluoro-1-(5-methoxy-4,6-dimethylpyridin-2-yl)-1H-isoindol-3-amine (200 mg, 0.45 mmol) and pyrimidin-5-ylboronic acid (61.8 mg, 0.50 mmol).

$^1$H NMR (400 MHz, CDCl$_3$) δ ppm 9.24 (s, 2 H) 9.22 (s, 1 H) 8.60 (d, 1 H) 7.94 (d, 1 H) 7.83 (s, 1 H) 7.44-7.54 (m, 1 H) 7.38-7.43 (m, 2 H) 7.11 (t, 1 H) 3.71 (s, 3 H) 2.49 (s, 3 H) 2.26 (s, 3 H); MS (ES+) m/z 441 [M+1]$^+$.

Example 37

1-(2-Cyclopropylpyridin-4-yl)-4-fluoro-1-(3-(pyrazin-2-yl)phenyl)-1H-isoindol-3-amine trifluoroacetate

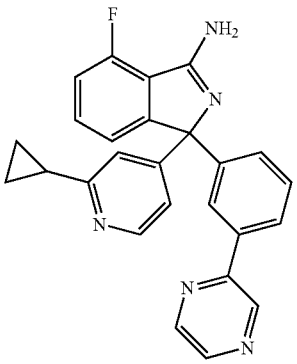

1-(3-Bromophenyl)-1-(2-cyclopropylpyridin-4-yl)-4-fluoro-1H-isoindol-3-amine (120 mg, 0.28 mmol), 2-(tributylstannyl)pyrazine (0.116 mL, 0.37 mmol), tetrakis(triphenylphosphine)palladium(0) (32.8 mg, 0.03 mmol) and DMF (2.5 mL) were heated in a microwave oven for 20 min at 150° C. The reaction mixture was diluted with brine and EtOAc and the phases were separated. The aqueous phase was extracted twice with EtOAc, and the combined organics were dried (Na$_2$SO$_4$), filtered and concentrated. The residue was purified twice by preparative chromatography to give the title compound (12.5 mg, 8.5%).

$^1$H NMR (400 MHz, DMSO-d$_6$, 296 K) δ ppm 11.92 (br. s., 1 H), 10.00 (br. s., 1 H), 9.48 (br. s., 1 H), 9.24 (d, 1 H), 8.71 (dd, 1 H), 8.64 (d, 1 H), 8.43 (d, 1 H), 8.19 (d, 1 H), 8.00-8.05 (m, 1 H), 7.94 (br. s., 1 H), 7.78 (d, 1 H), 7.55-7.66 (m, 2 H), 7.40 (m, 1 H), 7.30 (d, 1 H), 7.08 (dd, 1 H), 2.02-2.12 (m, 1 H), 0.86-0.98 (m, 4 H); MS (ES+) m/z 422 [M+1]$^+$.

Example 38

4-Fluoro-1-(3-(4-methoxypyridin-2-yl)phenyl)-1-(2-methoxypyridin-4-yl)-1H-isoindol-3-amine

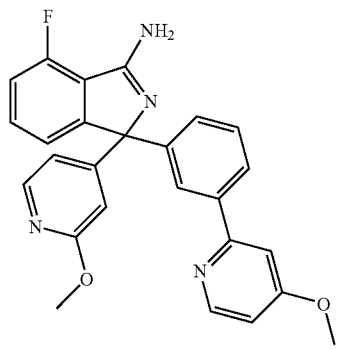

The title compound was synthesized as described in Example 29 in 13% yield starting from 1-(3-bromophenyl)-4-fluoro-1-(2-methoxypyridin-4-yl)-1H-isoindol-3-amine (0.150 g, 0.36 mmol) and 4-methoxy-2-(tributylstannyl)pyridine (0.188 g, 0.47 mmol).

$^1$H NMR (500 MHz, DMSO-d$_6$) δ ppm 8.43 (d, 1 H) 8.02-8.09 (m, 2 H) 7.90 (d, 1 H) 7.62 (d, 1 H) 7.50-7.58 (m, 1 H) 7.32-7.41 (m, 3 H) 7.25-7.32 (m, 1 H) 6.93 (dd, 1 H) 6.90 (dd, 1 H) 6.64 (d, 3 H) 3.88 (s, 3 H) 3.79 (s, 3 H); MS (ES+) m/z 441 [M+H]$^+$.

Example 39

2-(3-(3-Amino-4-fluoro-1-(2-methoxypyridin-4-yl)-1H-isoindol-1-yl) phenyl)isonicotinonitrile

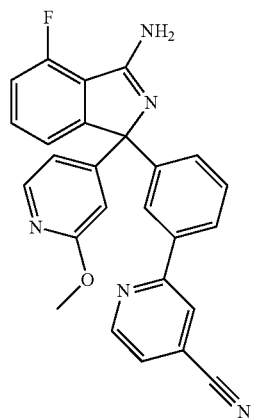

1-(3-Bromophenyl)-4-fluoro-1-(2-methoxypyridin-4-yl)-1H-isoindol-3-amine (0.200 g, 0.49 mmol), 2-(trimethylstannyl)isonicotinonitrile (0.194 g, 0.73 mmol), tetrakis(triphenylphosphine)palladium(0) (0.056 g, 0.05 mmol) and DMF (4 mL) were put in a microwave vial and heated in a microwave reactor at 110° C. for 20 min, then at 150° C. for 20 min. The reaction mixture was filtered through a syringe filter and purified by preparative HPLC. The desired fractions were pooled and concentrated in vacuo. The residue was partitioned between aqueous sodium bicarbonate (sat.) and ethyl acetate. The aqueous layer was extracted with EtOAc (×2), the combined organic layers were dried ($Na_2SO_4$), filtered and concentrated in vacuo to afford the title compound (0.018 g, 9%). $^1$H NMR (500 MHz, DMSO-$d_6$) δ ppm 8.86 (dd, 1 H) 8.40 (t, 1 H) 8.11-8.15 (m, 1 H) 8.04 (d, 1 H) 8.01 (ddd, 1 H) 7.78-7.81 (m, 1 H) 7.66 (d, 1 H) 7.51-7.57 (m, 1 H) 7.42-7.47 (m, 2 H) 7.24-7.31 (m, 1 H) 6.88 (dd, 1 H) 6.59-6.71 (m, 3 H) 3.79 (s, 3 H); MS (ES+) m/z 436 [M+H]$^+$.

Example 40

1-(2-(Difluoromethyl)pyridin-4-yl)-4-fluoro-1-(3-(pyrimidin-5-yl)phenyl)-1H-isoindol-3-amine

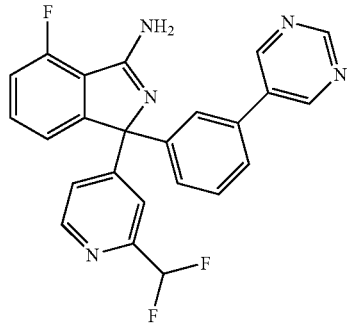

1-(3-Bromophenyl)-1-(2-(difluoromethyl)pyridin-4-yl)-4-fluoro-1H-isoindol-3-amine (0.168 g, 0.39 mmol), 5-pyrimidinylboronic acid (0.063 g, 0.51 mmol), [1,1'-bis (diphenylphosphino)ferrocene]palladium(II) chloride (0.016 g, 0.02 mmol), cesium carbonate (0.093 mL, 1.17 mmol) and DME:EtOH:water (6:3:1) (10.0 mL) were added to a microwave vial and heated at 150° C. in a microwave reactor for 20 min. Additional 5-pyrimidinylboronic acid (0.048 g, 0.39 mmol) was added. The reaction mixture was heated at 150° C. in a microwave reactor for 20 min. The reaction mixture was filtered through a syringe filter, concentrated in vacuo, redissolved in methanol and purified by preparative HPLC to afford the title compound (0.115 g, 60%).

$^1$H NMR (400 MHz, DMSO-$d_6$) δ ppm 9.18 (s, 1 H) 9.03 (s, 2 H) 8.59 (d, 1 H) 7.82 (d, 1 H) 7.70 (dt, 1 H) 7.63-7.67 (m, 1 H) 7.54-7.61 (m, 2 H) 7.44-7.53 (m, 3 H) 7.30 (dd, 1 H) 6.92 (t, 1 H); MS (ES+) m/z 432 [M+H]$^+$.

Example 41

(R) and (S) 1-(2-(Difluoromethyl)pyridin-4-yl)-4-fluoro-1-(3-(pyrimidin-5-yl)phenyl)-1H-isoindol-3-amine

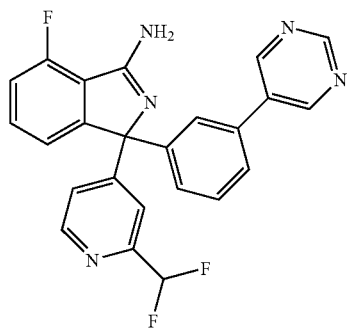

1-(2-(Difluoromethyl)pyridin-4-yl)-4-fluoro-1-(3-(pyrimidin-5-yl)phenyl)-1H-isoindol-3-amine was submitted to preparative chromatography for enantiomeric separation using a Chiralcel OD column (20×250 mm; 10 µm) using 10% MeOH+0.1% DEA/90% $CO_2$; as eluent (Flowrate: 50 mL/min).

Isomer 1 with unknown absolute configuration:

$^1$H NMR (400 MHz, DMSO-$d_6$) δ ppm 9.18 (s, 1 H) 9.03 (s, 2 H) 8.59 (d, 1 H) 7.82 (d, 1 H) 7.70 (dt, 1 H) 7.63-7.67 (m, 1 H) 7.53-7.61 (m, 2 H) 7.44-7.53 (m, 3 H) 7.30 (dd, 1 H) 6.67-7.09 (m, 3 H); MS (ES+) m/z 432 [M+H]$^+$.

Isomer 2 with unknown absolute configuration:

$^1$H NMR (400 MHz, DMSO-$d_6$) δ ppm 9.18 (s, 1 H) 9.03 (s, 2 H) 8.59 (d, 1 H) 7.82 (d, 1 H) 7.70 (dt, 1 H) 7.65 (t, 1 H) 7.54-7.61 (m, 2 H) 7.44-7.53 (m, 3 H) 7.30 (dd, 1 H) 6.67-7.07 (m, 3 H); MS (ES+) m/z 432 [M+H]$^+$.

Example 42

1-(2-(Difluoromethyl)pyridin-4-yl)-4-fluoro-1-(2-(pyrimidin-5-yl)pyridin-4-yl)-1H-isoindol-3-amine

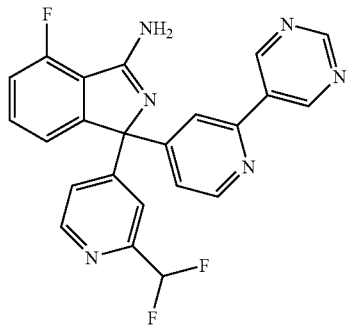

1-(2-Bromopyridin-4-yl)-1-(2-(difluoromethyl)pyridin-4-yl)-4-fluoro-1H-isoindol-3-amine (64 mg, 0.15 mmol), 5-pyrimidinylboronic acid (23.80 mg, 0.19 mmol), [1,1'-bis (diphenylphosphino)ferrocene]palladium(II) chloride (6.03 mg, 7.39 µmol), cesium carbonate (0.035 mL, 0.44 mmol) and DME:EtOH:water (6:3:1) (3.00 mL) were put in a microwave vial and heated at 150° C. in a microwave reactor for 20 min. The reaction mixture was filtered through a syringe filter and purified by prep-HPLC. The desired fractions were pooled and freeze dried over night to give the title compound (25.7 mg, 39%).

$^1$H NMR (400 MHz, DMSO-$d_6$) δ ppm 9.32-9.36 (m, 2 H) 9.24 (s, 1 H) 8.68 (dd, 1 H) 8.62 (d, 1 H) 7.98 (dd, 1 H) 7.89 (d, 1 H) 7.61 (td, 1 H) 7.56 (d, 1 H) 7.51 (dt, 1 H) 7.46 (dd, 1 H) 7.34 (dd, 1 H) 6.74-7.10 (m, 3 H); MS (ES−) m/z 431 [M−H]$^−$.

Example 43

5-(3-Amino-4-fluoro-1-(3-(pyrimidin-5-yl)phenyl)-1H-isoindol-1-yl)-2-methoxybenzonitrile

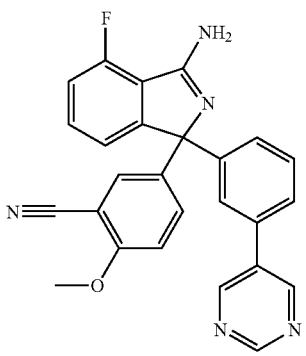

1-(3-Chloro-4-methoxyphenyl)-4-fluoro-1-(3-(pyrimidin-5-yl)phenyl)-1H-isoindol-3-amine (190 mg, 0.43 mmol), zinc cyanide (0.024 mL, 0.38 mmol), 2-dicyclohexylphosphino-2',6'-dimethoxybiphenyl (52.6 mg, 0.13 mmol), tris(dibenzylideneacetone)dipalladium(0) (58.7 mg, 0.06 mmol), DMF (5 mL) and a drop of water were added into a vial and heated in a microwave reactor for 1 h at 160° C. The mixture was filtered, diluted with MeOH and purified by preparative HPLC. The fractions containing the desired product were pooled and the MeCN removed in vacuo. The resulting aqueous residue was diluted with saturated aqueous NaHCO$_3$ and extracted with DCM. The combined organics were passed through a phase separator (Sorbent), concentrated and dried in vacuum oven at 40° C. over night, to afford 85 mg (45%) of the title compound.

$^1$H NMR (400 MHz, DMSO-d$_6$) δ ppm 9.17 (s, 1 H) 9.02 (s, 2 H) 7.79 (d, 1 H) 7.59-7.70 (m, 3 H) 7.49-7.59 (m, 2 H) 7.35-7.50 (m, 2 H) 7.26 (dd, 1 H) 7.17 (d, 1 H) 6.64 (br. s., 2 H) 3.87 (s, 3 H); MS (ES+) m/z 436 [M+1]$^+$.

Example 44

4-Fluoro-1-(5-methoxy-4,6-dimethylpyridin-2-yl)-1-(3-(pyrimidin-5-yl)phenyl)-1H-isoindol-3-amine

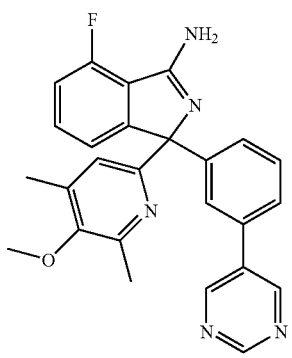

1-(3-Bromophenyl)-4-fluoro-1-(5-methoxy-4,6-dimethylpyridin-2-yl)-1H-isoindol-3-amine (272 mg, 0.62 mmol), pyrimidin-5-ylboronic acid (92 mg, 0.74 mmol), cesium carbonate (604 mg, 1.85 mmol) and dichloro[1,1'-bis (diphenylphosphino)ferrocene]palladium (II) dichloromethane adduct (50.4 mg, 0.06 mmol) were dissolved in DME:EtOH:water (6:3:1) (5 mL) and irradiated in a microwave oven for 20 min at 150° C. EtOAc, water and brine were added and the organic phase was collected, dried (Na$_2$SO$_4$) and filtered. The solvent was removed under reduced pressure and the residue was purified by preparative HPLC to afford 45 mg (17%) of the title compound.

$^1$H NMR (600 MHz, DMSO-d$_6$) δ ppm 9.17 (s, 1 H) 8.96 (s, 2 H) 7.96 (d, 1 H) 7.66-7.75 (m, 1 H) 7.60 (d, 1 H) 7.46-7.56 (m, 2 H) 7.36-7.45 (m, 2 H) 7.06-7.30 (m, 1 H) 6.55 (br. s., 2 H) 3.64 (s, 3 H) 2.39 (s, 3 H) 2.20 (s, 3 H); MS (ES+) m/z 440 (M+H)$^+$.

Example 45

1-(2,6-Dimethylpyrimidin-4-yl)-4-fluoro-1-(3-(pyrimidin-5-yl)phenyl)-1H-isoindol-3-amine

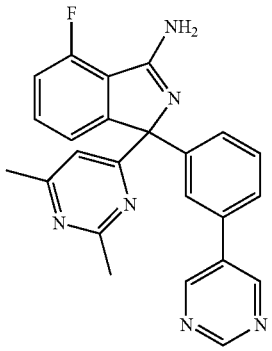

1-(3-Bromophenyl)-1-(2,6-dimethylpyrimidin-4-yl)-4-fluoro-1H-isoindol-3-amine (300 mg, 0.73 mmol), pyrimidin-5-ylboronic acid (108 mg, 0.88 mmol), cesium carbonate (713 mg, 2.19 mmol) and dichloro[1,1'-bis(diphenylphosphino)ferrocene]palladium (II) dichloromethane adduct (59.6 mg, 0.07 mmol) were dissolved in DME:EtOH:water (6:3:1) (5 mL) and heated in a microwave oven for 20 min at 150° C. EtOAc, water and brine were added and the organic phase was collected, dried and filtered. The solvent was removed under reduced pressure and the residue was purified by preparative HPLC to afford 49 mg (15%) of the title compound.

$^1$H NMR (600 MHz, DMSO-d$_6$) δ ppm 9.17 (s, 1 H) 8.97 (s, 2 H) 7.94 (d, 1 H) 7.70 (t, 1 H) 7.63 (dt, 1 H) 7.46-7.60 (m, 2 H) 7.44 (t, 1 H) 7.39 (s, 1 H) 7.14-7.30 (m, 1 H) 6.61 (br. s., 2 H) 2.54 (s, 3 H) 2.38 (s, 3 H); MS (ES+) m/z 411 [M+H]$^+$.

Example 46

1-(3,4-Difluoro-5-methoxyphenyl)-4-fluoro-1-(3-(pyrimidin-5-yl)phenyl)-1H-isoindol-3-amine

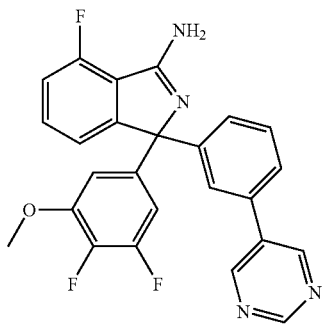

The title compound was synthesized as described for Example 45 in 14% yield starting from 1-(3-Bromophenyl)-1-(3,4-difluoro-5-methoxyphenyl)-4-fluoro-1H-isoindol-3-amine (714 mg, 1.60 mmol) and pyrimidine-5-boronic acid (237 mg, 1.92 mmol).

$^1$H NMR (600 MHz, DMSO-d$_6$) δ ppm 9.17 (s, 1 H) 9.01 (s, 2 H) 7.82 (d, 1 H) 7.66 (dt, 1 H) 7.57-7.62 (m, 1 H) 7.54 (d, 1 H) 7.37-7.50 (m, 2 H) 7.26 (t, 1 H) 6.84-7.04 (m, 2 H) 6.60 (br. s., 2 H) 3.77 (s, 3 H); MS (ES+) m/z 447 (M+H)$^+$ Example 47

2-(5-(3-Amino-4-fluoro-1-(3-(pyrimidin-5-yl)phenyl)-1H-isoindol-1-yl)-2-methoxy-3-methylphenyl)acetonitrile

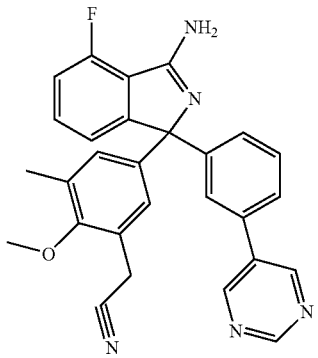

To a solution of 1-(3-(bromomethyl)-4-methoxy-5-methylphenyl)-4-fluoro-1-(3-(pyrimidin-5-yl)phenyl)-1H-isoindol-3-amine (185 mg, 0.36 mmol) in MeCN (5 mL) was added potassium cyanide (69.8 mg, 1.07 mmol) and the reaction mixture was stirred at rt over night. The mixture was filtered and the filtrate was concentrated in vacuo and purified by preparative HPLC to give 23 mg (12%) of the title compound.

$^1$H NMR (600 MHz, DMSO-d$_6$) δ ppm 9.17 (s, 1 H) 9.00 (s, 2 H) 7.70 (d, 1 H) 7.58-7.69 (m, 2 H) 7.48-7.59 (m, 1 H) 7.39-7.50 (m, 2 H) 7.19-7.30 (m, 2 H) 7.14 (d, 1 H) 3.87 (s, 2 H) 3.67 (s, 3 H) 2.18 (s, 3 H); MS (ES+) m/z 464 [M+H]$^+$.

Example 48

4-Fluoro-1-(4-fluoro-3-methoxyphenyl)-1-(3-(pyrimidin-5-yl)phenyl)-1H-isoindol-3-amine

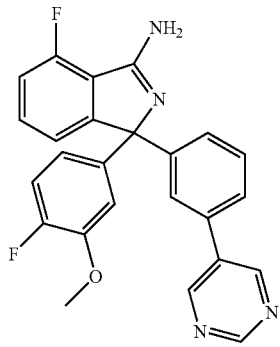

The title compound was synthesized as described for Example 45 in 20% yield starting from 1-(3-bromophenyl)-4-fluoro-1-(4-fluoro-3-methoxyphenyl)-1H-isoindol-3-amine (210 mg, 0.49 mmol) and pyrimidine-5-boronic acid (72.7 mg, 0.59 mmol).

$^1$H NMR (500 MHz, DMSO-d$_6$) δ ppm 3.70 (s, 3 H) 6.58 (br. s., 2 H) 6.84-6.93 (m, 1 H) 7.02-7.15 (m, 2 H) 7.24 (t, 1 H) 7.39-7.47 (m, 2 H) 7.48-7.55 (m, 1 H) 7.58-7.60 (m, 1 H) 7.65 (dt, 1 H) 7.73 (d, 1 H) 9.00 (s, 2 H) 9.17 (s, 1 H); MS (ES+) m/z 429 (M+H)$^+$ Example 49

4-Fluoro-1-(6-methoxy-5-(trifluoromethyl)pyridin-3-yl)-1-(3-(pyrimidin-5-yl)phenyl)-1H-isoindol-3-amine

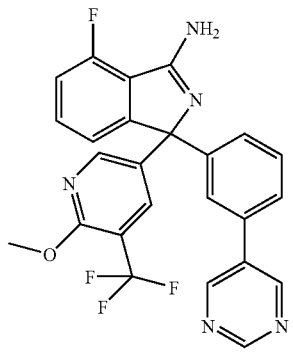

The title compound was synthesized as described for Example 1 in 79% yield, starting from 1-(3-bromophenyl)-4-fluoro-1-(6-methoxy-5-(trifluoromethyl)pyridin-3-yl)-1H-isoindol-3-amine (680 mg, 1.42 mmol), pyrimidin-5-yl-boronic acid (211 mg, 1.70 mmol). $^1$H NMR (400 MHz, DMSO-d$_6$) δ ppm 9.18 (s, 1 H) 9.05 (s, 2 H) 8.41 (d, 1 H) 7.91 (d, 1 H) 7.87 (d, 1 H) 7.66-7.72 (m, 2 H) 7.56 (td, 1 H) 7.44-7.52 (m, 2 H) 7.28 (dd, 1 H) 6.72 (br. s., 2 H) 3.94 (s, 3 H); MS (ES+) m/z 480 [M+1]$^+$.

Example 50

4-(3-Amino-4-fluoro-1-(2-(trifluoromethyl)pyridin-4-yl)-1H-isoindol-1-yl)-2-(pyrazin-2-yl)phenol

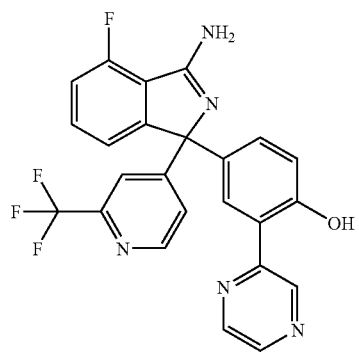

To a solution of 4-fluoro-1-(4-methoxy-3-(pyrazin-2-yl) phenyl)-1-(2-(trifluoromethyl) pyridin-4-yl)-1H-isoindol-3-amine (0.65 g, 1.36 mmol) in DCM (12.5 ml), boron tribromide (0.718 ml, 4.20 mmol) was added dropwise at 0° C. The mixture was stirred at 0° C. for 1 hour and then allowed to reach room temperature. Water (5 ml) was added and the pH was adjusted to approx 8 with aqeuous conc. $NH_3$. The organic phase was separated and aqueous phase was extracted with DCM (20 mL). The combined organic phases were passed through a phase separator (Sorbent) and concentrated under reduced pressure. The residue was purified twice by preparative chromatography to give the title compound (210 mg, 32%).

$^1$H NMR (600 MHz, DMSO-$d_6$) δ ppm 9.23 (dd, 1 H) 8.68 (d, 1 H) 8.65 (dd, 1 H) 8.54 (d, 1 H) 7.85 (d, 1 H) 7.69-7.72 (m, 2 H) 7.65 (dt, 1 H) 7.54-7.59 (m, 1 H) 7.25-7.32 (m, 2 H) 6.96 (d, 1 H); MS (ES+) m/z 466 [M+1]$^+$.

Example 51

4-Fluoro-1-(4-methoxy-3-(pyrimidin-5-yl)phenyl)-1-(2-(trifluoromethyl)pyridin-4-yl)-1H-isoindol-3-amine

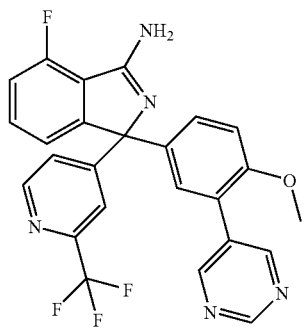

1-(3-Bromo-4-methoxyphenyl)-4-fluoro-1-(2-(trifluoromethyl)pyridin-4-yl)-1H-isoindol-3-amine (1.5 g, 3.12 mmol), pyrimidin-5-ylboronic acid (0.542 g, 4.37 mmol), [1,1'-bis (diphenylphosphino)ferrocene]palladium(II) chloride (0.128 g, 0.16 mmol) and aqueous potassium carbonate (2M, 4.69 mL, 9.37 mmol) were dissolved in DMF (14 mL). The resulting mixture was heated to 150° C. for 20 mins by microwaves. Methanol (20 mL) was added and the mixture concentrated in vacuo. Dichloromethane (40 mL), water (20 mL) and brine (5 mL) were added and the organic phase separated and evaporated directly on silica. The crude product was purified by gradient column chromatography (40 g silica column eluted with 0-10% [0.1M ammonia in methanol] in dichloromethane). The desired fractions were combined and evaporated to give 648 mg (43%) of the title compound.

$^1$H-NMR (600 MHz, CDCl$_3$) δ ppm 9.15 (s, 1 H) 8.83 (s, 2 H) 8.67 (d, 1 H) 7.69 (d, 1 H) 7.50-7.56 (m, 2 H) 7.37 (d, 1 H) 7.31 (dd, 1 H) 7.21 (d, 1 H) 7.18 (t, 1 H) 6.99 (d, 1 H) 3.85 (s, 3 H); MS (ES+) m/z 480 [M+1]$^+$ Example 52

1-(2-Cyclopropylpyridin-4-yl)-4-fluoro-1-(2-(pyrimidin-5-yl)pyridin-4-yl)-1H-isoindol-3-amine

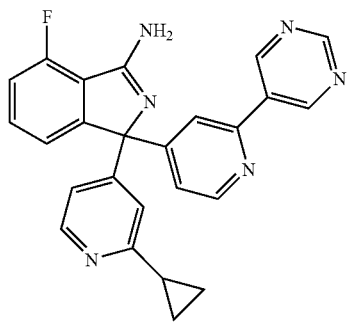

1-(2-Bromopyridin-4-yl)-1-(2-cyclopropylpyridin-4-yl)-4-fluoro-1H-isoindol-3-amine (92 mg, 0.22 mmol), 5-pyrimidinylboronic acid (35.0 mg, 0.28 mmol), [1,1'-bis(diphenylphosphino)ferrocene]palladium(II) chloride (8.87 mg, 10.87 μmol), cesium carbonate (0.052 mL, 0.65 mmol) and DME:EtOH:water (6:3:1) (3.00 mL) were put in a microwave vial and heated at 150° C. in a microwave reactor for 20 min. The mixture was filtered through a syringe filter and purified by prep-HPLC. The desired fractions were pooled and concentrated in vacuo. The residue was redissolved in acetonitrile and water was added. The mixture was freeze dried to give the title compound (46.9 mg, 47%). $^1$H NMR (400 MHz, DMSO-$d_6$) δ ppm 9.33 (s, 2 H) 9.24 (s, 1 H) 8.67 (d, 1 H) 8.29 (d, 1 H) 7.96 (d, 1 H) 7.87 (d, 1 H) 7.58 (td, 1 H) 7.46 (dd, 1 H) 7.31 (dd, 1 H) 7.21 (d, 1 H) 7.03 (dd, 1 H) 6.79 (br. s., 2 H) 1.96-2.07 (m, 1 H) 0.80-0.96 (m, 4 H); MS (ES+) m/z 423 [M+1]$^+$.

Example 53

3-(5-Difluoromethoxy-4,6-dimethyl-pyridin-2-yl)-7-fluoro-3-(5'-fluoro-[2,3']bipyridinyl-4-yl)-3H-isoindol-1-ylamine

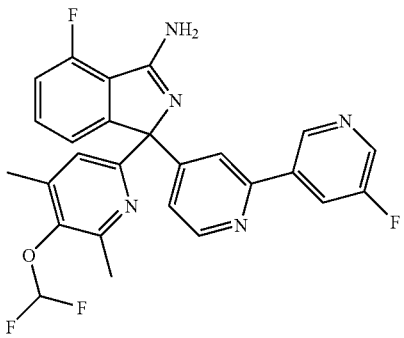

A mixture of 3-(2-chloro-pyridin-4-yl)-3-(5-difluoromethoxy-4,6-dimethyl-pyridin-2-yl)-7-fluoro-3H-isoindol-1-ylamine 1 (0.14 g, 0.32 mmol), 5-fluoropyridine-3- boronic acid (0.068 g, 0.485 mmol), Pd(PPh$_3$)$_4$ (0.065 g, 0.056 mmol), aqueous Na$_2$CO$_3$ (2M, 1 mL, 2 mmol) in DME (4 mL) was degassed for 15 minutes using nitrogen and then heated in a sealed tube at 90° C. for 16 hours. The reaction mixture was cooled to room temperature, diluted with EtOAc (20 mL) and washed with saturated NaHCO$_3$ solution (10 mL) and H$_2$O (20 mL), dried over Na$_2$SO$_4$, filtered and concentrated under reduced pressure. The residue was purified by preparative HPLC to afford the title compound (22 mg, 14%).
$^1$H NMR (400 MHz, CDCl$_3$) δ ppm 8.92 (br. s., 1 H) 8.61 (d, 1 H) 8.48 (br. s., 1 H) 8.00 (d, 2 H) 7.85 (s, 1 H) 7.54-7.61 (m, 1 H) 7.51 (s, 1 H) 7.40 (d, 1 H) 7.16 (t, 1 H) 6.36 (s, 1 H) 2.51 (s, 3 H) 2.30 (s, 3 H).
MS (ES+) m/z 494.18 [M+1]$^+$.

Example 54

5-(3-Amino-4-fluoro-1-(3-(pyrimidin-5-yl)phenyl)-1H-isoindol-1-yl)-2-methoxy-3-methylbenzonitrile

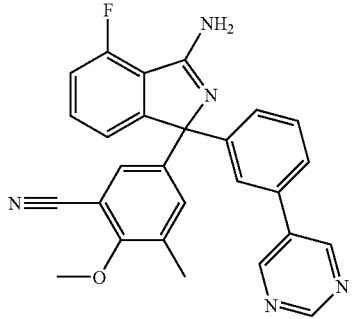

The title compound was synthesized as described for Example 1 in 63% yield, starting from 5-(3-amino-1-(3-bromophenyl)-4-fluoro-1H-isoindol-1-yl)-2-methoxy-3-methylbenzonitrile (88 mg, 0.20 mmol) and pyrimidin-5-ylboronic acid (36.3 mg, 0.29 mmol).
$^1$H NMR (500 MHz, DMSO-d$_6$) d ppm 9.17 (s, 1 H) 9.03 (s, 2 H) 7.84 (d, 1 H) 7.61-7.68 (m, 2 H) 7.52-7.58 (m, 2 H) 7.43-7.49 (m, 3 H) 7.23-7.29 (m, 1 H) 3.86 (s, 3 H) 2.20 (s, 3 H); MS (ES+) m/z 450 [M+1]$^+$.

Example 55

6-Chloro-4-fluoro-1-(3-(pyrimidin-5-yl)phenyl)-1-(2-(trifluoromethyl)pyridin-4-yl)-1H-isoindol-3-amine

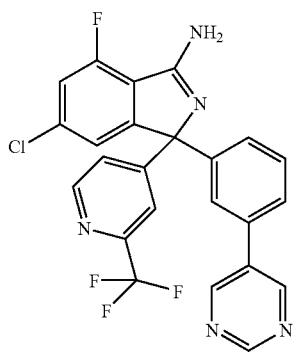

The title compound was synthesized as described for Example 1 in 18% yield, starting from 3-(3-amino-6-chloro-4-fluoro-1-(2-(trifluoromethyl)pyridin-4-yl)-1H-isoindol-1-yl) phenyl trifluoromethanesulfonate (66.5 mg, 0.12 mmol) and 5-pyrimidinylboronic acid (17.84 mg, 0.14 mmol).
$^1$H NMR (500 MHz, DMSO-d$_6$) δ ppm 9.18 (s, 1 H) 9.07 (s, 2 H) 8.71 (d, 1 H) 8.10 (d, 1 H) 7.70-7.75 (m, 3 H) 7.66-7.70 (m, 1 H) 7.58 (dd, 1 H) 7.45-7.53 (m, 2 H) 6.88 (br. s., 2 H); MS (ES+) m/z 484, 486 [M+1]$^+$.

Example 56

6-Chloro-4-fluoro-1-(2-methylpyridin-4-yl)-1-(3-(pyrimidin-5-yl)phenyl)-1H-isoindol-3-amine

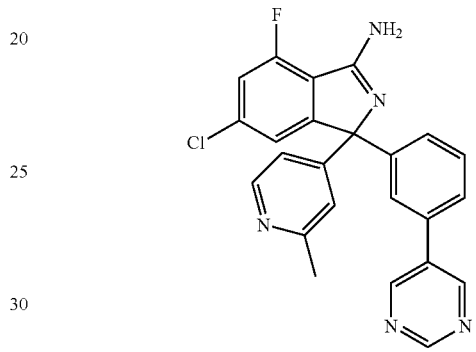

1-(3-Bromophenyl)-6-chloro-4-fluoro-1-(2-methylpyridin-4-yl)-1H-isoindol-3-amine (1 g, 2.32 mmol), pyrimidine-5-boronic acid (0.316 g, 2.55 mmol) and [1,1'-bis (diphenylphosphino)ferrocene]palladium(II) chloride (0.096 g, 0.12 mmol) were dissolved in DMF (10 mL) and heated to 90° C. Then aqueous potassium carbonate (3.48 mL, 6.97 mmol) was added and the resulting mixture was stirred at 120° C. for 2 h. When cooled to rt the mixture was diluted with water (50 mL) and extracted with DCM (3×50 mL). The combined organics were washed with water (75 mL), passed through a phase separator, concentrated and purified on a silica gel column eluted with 0-10% 0.1M NH$_3$ in MeOH in DCM to afford 310 mg (31% yield) of the title compound.
$^1$H NMR (500 MHz, DMSO-d$_6$) δ ppm 9.18 (s, 1 H) 9.03 (s, 2 H) 8.34 (d, 1 H) 7.96 (d, 1 H) 7.66-7.72 (m, 1 H) 7.64 (s, 1 H) 7.53 (dd, 1 H) 7.43-7.51 (m, 2 H) 7.18 (s, 1 H) 7.12 (dd, 1 H) 6.70 (br. s., 2 H) 2.39-2.42 (m, 3 H); MS (ES+) m/z 430, 432 [M+H]$^+$.

Assays

The level of activity of the compounds was tested using the following methods:

The level of activity of the compounds was tested using the following methods:

TR-FRET Assay

The β-secretase enzyme used in the TR-FRET is prepared as follows:

The cDNA for the soluble part of the human β-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in Tris buffer, pH 9.2 and had a purity of 95%.

The enzyme (truncated form) was diluted to 6 μg/mL (stock 1.3 mg/mL) and the substrate (Europium) CEVNLDAEFK(Qsy7) to 200 nM (stock 120 μM) in reaction buffer (NaAcetate, chaps, triton x-100, EDTA pH4.5). The robotic systems Biomek FX and Velocity 11 were used for all liquid handling and the enzyme and substrate solutions were kept on ice until they were placed in the robotic system. Enzyme (9 μl) was added to the plate then 1 μl of compound in dimethylsulphoxide was added, mixed and pre-incubated for 10 minutes. Substrate (10 μl) was then added, mixed and the reaction proceeded for 15 minutes at room temperature. The reaction was stopped with the addition of Stop solution (7 μl, NaAcetate, pH 9). The fluorescence of the product was measured on a Victor II plate reader with an excitation wavelength of 340 nm and an emission wavelength of 615 nm. The assay was performed in a Costar 384 well round bottom, low volume, non-binding surface plate (Corning #3676). The final concentration of the enzyme was 2.7 μg/ml; the final concentration of substrate was 100 nM (Km of ~250 nM). The dimethylsulphoxide control, instead of test compound, defined the 100% activity level and 0% activity was defined by wells lacking enzyme (replaced with reaction buffer). A control inhibitor was also used in dose response assays and had an IC50 of ~575 nM.

sAPPβ Release Assay

SH-SY5Y cells were cultured in DMEM/F-12 with Glutamax, 10% FCS and 1% non-essential aminoacids and cryopreserved and stored at −140° C. at a concentration of 7.5×106 cells per vial. Thaw cells and seed at a conc. of 1.5×105/ml in DMEM/F-12 with Glutamax, 10% FCS and 1% non-essential aminoacids to a 96-well tissue culture treated plate, 100 μl cell susp/well. The cell plates were then incubated for 7 hours at 37° C., 5% CO2. The cell medium was removed, followed by addition of 90 μl compound diluted in DMEM/F-12 with Glutamax, 10% FCS, 1% non-essential aminoacids and 1% PeSt to a final conc. of 1% DMSO. The compounds were incubated with the cells for 16 h (over night) at 37° C., 5% CO2. Meso Scale Discovery (MSD) plates were used for the detection of sAPPβ release. MSD sAPPβ plates were blocked in 3% BSA in Tris wash buffer (150 μl/well) for 1 hour in RT and washed 4 times in Tris wash buffer (150 μl/well). 50 μl of medium was transferred to the pre-blocked and washed MSD sAPPβ microplates, and the cell plates were further used in an ATP assay to measure cytotoxicity. The MSD plates were incubated with shaking in RT for 1 hour followed by washing 4 times. 25 μl detection is antibody was added (1 nM) per well followed by incubation with shaking in RT for 1 h and washing 4 times. 150 μl Read Buffer was added per well and the plates were read in a SECTOR Imager.

ATP Assay

As indicated in the sAPPβ release assay, after transferring 50 μL medium from the cell plates for sAPPβ detection, the plates were used to analyse cytotoxicity using the ViaLight™ Plus cell proliferation/cytotoxicity kit from Cambrex BioScience that measures total cellular ATP. The assay was performed according to the manufacture's protocol. Briefly, 25 μL cell lysis reagent was added per well. The plates were incubated at room temperature for 10 min. Two min after addition of 50 μL reconstituted ViaLight™Plus ATP reagent, the luminescence was measured in a Wallac Victor2 1420 multilabel counter.

Results

Typical $IC_{50}$ values for the compounds of the present invention are in the range of about 0.1 to about 30,000 nM. Biological data on exemplified final compounds is given below in

TABLE I

| Example No. | $IC_{50}$ in TR-FRET assay |
| --- | --- |
| 1 | 1600 |
| 2 | 27000 |
| 3 | 1800 |
| 4 | 1600 |
| 5 | 1700 |
| 6 | 1100 |
| 7 | 2000 |
| 8 | 12000 |
| 9 | 75 |
| 10 | 160 |
| 11 Isomer 1 | 100 |
| 11 Isomer 2 | 21000 |
| 12 | 200 |
| 13 Isomer 1 | NV |
| 13 Isomer 2 | 100 |
| 14 | 95 |
| 15 | 140 |
| 16 | 320 |
| 17 | 110 |
| 18 | 3400 |
| 19 | 4100 |
| 20 | 240 |
| 21 | 1100 |
| 22 | 870 |
| 23 | 250 |
| 24 | 280 |
| 25 | 370 |
| 26 | 460 |
| 27 | 400 |
| 28 | 470 |
| 29 | 200 |
| 30 | 320 |
| 31 | 86 |
| 32 | 90 |
| 33 | 730 |
| 34 | 81 |
| 35 | 35 |
| 36 | 490 |
| 37 | 87 |
| 38 | 430 |
| 39 | 1100 |
| 40 | 43 |
| 41 Isomer 1 | 38 |
| 41 Isomer 2 | 14000 |
| 42 | 310 |
| 43 | 560 |
| 44 | 79 |
| 45 | 270 |
| 46 | 690 |
| 47 | 83 |
| 48 | 350 |
| 49 | 600 |
| 50 | 420 |
| 51 | 5600 |
| 52 | 690 |
| 53 | 910 |
| 54 | 42 |
| 55 | 150 |
| 56 | 230 |

The invention claimed is:
1. A compound or a pharmaceutically acceptable salt thereof, wherein the compound corresponds to:
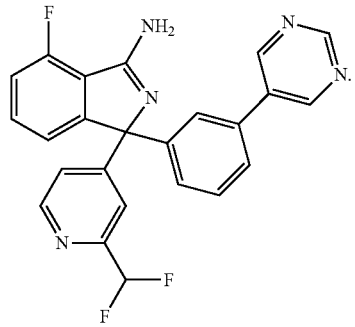
2. A compound or a pharmaceutically acceptable salt thereof according to claim 1, wherein the compound corresponds to:
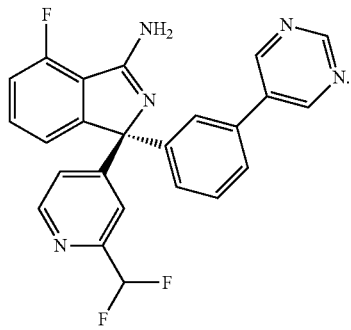
* * * * *